United States Patent [19]

Nakari et al.

[11] Patent Number: 5,989,870
[45] Date of Patent: Nov. 23, 1999

[54] METHOD FOR CLONING ACTIVE PROMOTERS

[75] Inventors: Tiina Hannele Nakari; Maija-Leena Onnela; Marja Hannele Ilmén; Merja Elisa Penttilä, all of Helsinki, Finland

[73] Assignee: Röhm Enzyme Finland Oy, Rajamäki, Finland

[21] Appl. No.: 08/389,564

[22] Filed: Feb. 16, 1995

Related U.S. Application Data

[63] Continuation of application No. 07/932,485, Aug. 19, 1992, abandoned, which is a continuation-in-part of application No. 07/496,155, Mar. 19, 1990, which is a continuation of application No. 07/044,077, Apr. 29, 1987, abandoned.

[30] Foreign Application Priority Data

Apr. 30, 1986 [GB] United Kingdom .................. 8610600

[51] Int. Cl.$^6$ .............................. C12N 15/00; C12N 1/14
[52] U.S. Cl. ..................... 435/91.1; 435/91.41; 435/911; 435/913; 435/925; 435/929; 435/931; 435/945
[58] Field of Search ............................. 435/172.3, 91.41, 435/911, 913, 925, 929, 931, 945, 91.1

[56] References Cited

U.S. PATENT DOCUMENTS

| | | | |
|---|---|---|---|
| 4,725,535 | 2/1988 | Sonenshein et al. | 435/6 |
| 5,108,918 | 4/1992 | Groenen et al. | 435/172.3 |
| 5,674,707 | 10/1997 | Hintz et al. | 435/69.1 |
| 5,710,021 | 1/1998 | Hintz et al. | 435/69.1 |

FOREIGN PATENT DOCUMENTS

| | | |
|---|---|---|
| 0 137 280 A1 | 4/1985 | European Pat. Off. . |
| 0 244 598 A1 | 11/1987 | European Pat. Off. . |
| 0 306 107 A3 | 3/1989 | European Pat. Off. . |
| 0 459 643 A1 | 12/1991 | European Pat. Off. . |
| WO 92/00379 | 1/1992 | WIPO . |
| WO 90/02172 | 3/1992 | WIPO . |

OTHER PUBLICATIONS

Teeri, T. et al., "The Molecular Cloning of the Major Cellulase Gene from *Trichoderma reesei*," *Bio/Technol.*:696–699 (Oct. 1983).

Harkki, A. et al., "A Novel Fungal Expression System: Secretion Of Active Calf Chymosin From The Filamentous Fungus *Trichoderma reesei*," *Bio/Technol.* 7:596–603 (Jun. 1989).

Judelson, H.W. et al., "Highly Abundant and Stage–Specific mRNAs in the Obligate Pathogen *Bremia lactucae*," *Molecular Plant–Microbe Interactions* 3(4):225–232 (1990).

Turgeon, B.G. et al., "Development of a Fungal Transformation System Based on Selection of Sequences with Promoter Activity," *Molec. and Cell. Biol.* 7(9):3297–3305 (1987).

Curie, C. et al., "Cis and trans–acting elements involved in the activation of *Arabidopsis thaliana* A1 gene encoding the translation elongation factor EF–1α," *Nucl. Acids Res.* 19(6):13–5–1310 (1991).

Kim, D.W. et al., "Use of the human elongation factor 1α promoter as a versatile and efficient expression system," *Gene* 91:217–223 (1990).

Miyajima, A. et al., "Coordination of Levels of Elongation Factors Tu, Ts, and G, and Ribosomal Protein S1 in *Escherichia coli*," *J. Biochem.* 83:453–462 (1978).

Thiele, D. et al., "Elongation Factor 1α from *Saccharomyces cerevisiae*: Rapid Large–Scale Purification And Molecular Characterization," *J. Biol. Chem.* 260 (5):3084–3089 (1985).

Uetsuki, T. et al., "Isolation and Characterization of the Human Chromosomal Gene for Polypeptide Chain Elongation Factor–1α," *J. Biol. Chem.* 10:5791–5798 (1989).

Schirmaier, F. et al., "Identification of two genes coding for the translation elongation factor EF–1α of *S. cerevisiae*," *EMBO J.* 3(13):3311–3315 (1984).

Liboz, Thierry et al., "The four members of the gene family encoding the *Arabidopsis thaliana* translation elongator factor EF–1α are actively transcribed," *Plant Mol. Biol.* 14:107–110 (1989).

Auer, J. et al., "Organisation and Nucleotide Sequence of a Gene Cluster Comprising the Translation Elongation Factor 1α from *Sulfolobus acidocaldarius*," *System. Appl. Microbiol.* 14(1):14–22 (1990).

Ishiura, M. et al., "Simplified cosmid vectors for gene transfer to cultured mammalian cells: isolation of the gene for elongation factor 2 from the mouse," *Gene* 85:427–433 (1989).

Penttilä, M.E. et al., "Cloning of *Aspergillus niger* genes in yeast. Expression of the gene coding Aspergillus β–glucosidase," *Mol. Gen. Genet.* 194(3):494–499 (1984).

von Melchner, H. et al., "Isolation of cellular promoters by using a retrovirus promoter trap," *Proc. Natl. Acad. Sci. USA* 87:3733–3737 (1990).

Neve et al., "Eukaryotic DNA fragments which act as promoters for a plasmid gene," *Nature* 277: 324–325 (1979).

(List continued on next page.)

*Primary Examiner*—Elizabeth F. McElwain
*Attorney, Agent, or Firm*—Sterne, Kessler, Goldstein & Fox P.L.L.C.

[57] ABSTRACT

A method is described for the identification and cloning of promoters that express under a defined environmental condition, such as growth in glucose medium. Using this method, five Trichodermal promoters capable of the high expression of operably linked coding sequences are identified, one of which is the promoter for *T. reesei tef*1. Also provided are altered cbh1 promoters, altered so that glucose no longer represses expression from such promoter. The invention further provides vectors and hosts that utilize such promoters, and unique fungal enzyme compositions from such hosts.

5 Claims, 45 Drawing Sheets

OTHER PUBLICATIONS

Soldati, L. et al., "Effective gene expression in *Pseudomonas aeruginosa* under the control of the *Escherichia coli* consensus promoter," *FEMS Microbiol. Letts.* 42:163–167 (1987).

An, G. et al., "Plasmid Vehicles for Direct Cloning of *Escherichia coli* Promoters," *J. Bacteriol.* 140(2):400–407 (1979).

Band, L. et al., "Construction of a vector for cloning promoters in *Bacillus subtilis*," *Gene* 26 2(3):313–315 (1983).

Achen, M.G. et al., "Construction of plasmid vectors for the detection of streptococcal promoters," *Gene* 45 (1):45–49 (1986).

Goodey, A.R. et al., "The selection of promoters for the expression of heterologous genes in the yeast *Saccharomyces cerevisiae*," *Mol. Gen. Genet.* 204:505–511 (1986).

Pater, M.M. et al., "Thymidine Kinase of Herpes Virus as a Vehicle for the Isolation and Characterization of Unknown Mammalian Promoters and Enhancers," *J. Mol. Appl. Genet.* 2(4):363–371 (1984).

Slos, P. et al., "Isolation and Characterization of Chromosomal Promoters of *Streptococcus salivarius* subsp. *thermophilus*," *Appl. Environ. Microbiol.* 57(5):1333–1339 (1991).

Santangelo, G.M. et al., "Properties of Promoters Cloned Randomly from the *Saccharomyces cerevisiae* Genome," *Molec. and Cell. Biol.* 8(10):4217–4224 (1988).

Savochkina, L.P. et al., "Stability of Cloned Promoter–Containing Fragments," *Mol. Gen. Genet.* 189:142–147 (1983).

Ogawa, H. et al., "Molecular cloning of promoter–containing fragments from *Bacillus stearothermophilus* and their expression in *Escherichia coli* and *Bacillus subtilis*," *FEMS Microbiol. Letts* 24 (2–3):169–172 (1984).

Gatignol, A. et al., "Cloning of *Saccharomyces cerevisiae* promoters using a probe vector based on phleomycin resistance," *Gene* 91:35–41 (1990).

Goldfarb, D.S. et al., "Expression Probe Plasmids To Isolate And Analyze *Bacillus Subtillus* Regulatory Elements," *Proc. Int. Symp. Genet. Ind. Microorganisms,* pp. 120–124 (1982).

Kubota, M. et al., "Random screening of promoters from *Escherichia coli* and classification based on the promoter strength," *Jpn. J. Genet.* 66:399–409 (1991).

Flick, J.S. et al., "Two Systems of Glucose Represseion of the GAL1 Promoter in *Saccharomyces cerevisiae*," *Mol. and Cell. Biol.* 10(9):4757–4769 (1990).

Shoemaker, S.P. et al., "Cellulases: Diversity Amongst Improved Trichoderma Strains," In: *Trends In The biology Of Fermentations For Fuels And Chemicals,* Hollaender, Alexander (ed.), Plenum Press, New York, pp. 89–109 (1981).

Montenecourt, B.S. et al., "Preparation of Mutants of *Trichoderma reesei* with Enhanced Cellulase Production," *Appl. and Environ. Microbiol.* 34(6):777–782 (1977).

Takashima, S. et al., "Analysis of Cre1 binding sites in the *Trichoderma resei* cbhl upstream region," *FEMS Microbiol. Letters* 145:361–366 (1996).

Margret, D. and Lauquin, G.J.M. 1986. The Yeast SRP Gene: Positive Modulation by Glucose of its Transcriptional Expression, Biochemical and Biophysical Research Communications, 138(1):297–303.

Nakari et. al., Proceeding of the Second Tricel Symposium on *Trichoderma reesei* Cellulases and Other Hydrolases, Espoo, Finland, ed by P. Suominen et. al. Foundation for Biotechnical and Industrial Fermentation Research 8(1993):239–246.

Penttkä et al, 1987, Gene 61:155–164.

```
      10         20         30         40         50         60
       |          |          |          |          |          |
   1 CGCCGTGACG ACAGAAACGG AGCCCGCGAG TTTGGATACG CCGCTGAAAT GGGGCTTGAC
  61 GGTGAAGGAG AAGCCGAGCG CGGTGCCAGA GGACAAGATG GATGTAGAGC CAGGCGACGA
 121 CGACCAAACG CAACCATCAA ATCAATCAGA TGGCAATGAC GCACCACCGC CCCAGCAGCG
 181 CGAACCGCCG ACGAAGAAGC CATGGACGCG CTCCTCGGCA AGACGCCCAA GGAACAGAAA
 241 AAAGTAATCT CCGCACCCGT ATCAGAAGAC GACGCCTACC GCCGCGACGT CGAAGCCTCC
 301 GGCGCGGTGT CCACGCTCCA GGATTACGAA GACATGCCCG TCGAGGAGTT TGGCGCCGCC
 361 CTCCTCCNNN GCATGGGCTG GAACGGGGAA GCCCGCGGCC CGCCGGTCAA GCAGGTCAAG
 421 AGGCGGCAGA ACAGGCTCGG CCTCGGCGCC AAGGAGCTCA AGGAGGAAGA GGACCTCGGC
 481 GGGTGGAACC AGAACGGCAA GAAAAAGTCG AGGCCSCGCG GCTGAGCGAG TATCGGAGGG
 541 AGGAGAGCAA GCGCAAGGAA GGCCGGGGGC ATGAGGACAG CTATAAACGA GAGAGGGAGC
 601 GCGAACGGAT CGCGAGAGGG ATCACTACAG GGAGCGAGAC CGGGACAGGG ATCGCGATTA
 661 TAGGGATCGG GATAGGGATA GACATCGGGA CCACGATAGG CACAGGGACC GACATCGCGA
 721 CTCTGACCGG CACCATCGAC GATGAAGGAG CTTTTGCATT CTTCTCTTCG TCAACCACTT
 781 TTGAGACTAA CATTAACCAT GCCGTTTTCT TGAAAAGCTT GTACTCATCA TGATGTTTTT
 841 AAGCAAATAG GCGACAGGCG TACAGACACC TTAATATCAC ATAGAGGCAC GGCACACATA
 901 CGTCTTGGAG AAGACACGTA CTTACGAATG ATGGGAGAAT TACCTACTCT GACTTGTGTA
 961 AATTAGAATA TCAATGACAC TATGTATATT CAGTCGAGCT GCGAATGGTC ACACATTGTC
1021 TGATCTGCGA ATTTGTATGT GCTGCCTCTC CCTCTGACCT TCTGGTCTGG TGATACCATC
1081 CTCCCTCAGT TTGGATCATC GCCTTATTCT TCTTCCCTCT TCTGCATCTG CTTCCTGCTC
1141 GTTTGAGGAA CATCGCCAGC TGACTCTGCT TGCCTCGCAG CGATCTAGTC AAGAACAACA
1201 CNAGCTCTCA CGCTACATCA CACAAACCGT CAAAATGGGT AAGGAGGACA AGACTCACAT
1261 CAACGTGGTC GTCATCGTAC GTATTTTCCG ATCCCTCATC GGCNGTCATC TGNCCAGTCT
1321 GATTCCAAGA ATCACCGTGC TAACCATATA CCATCTAGGG GTGCGTATTC CATCAATCAT
1381 CTTGAGCCAG ATCGACCGAA CATACGATAC TGACTTTGCT ACGACAGCCA CGTCGACTCC
```

FIG.1B

```
1441 GGCAAGTCTA CCACCGTGAG TAAACACCCA TTCCACTCCA CGACCGCAAG CTCCATCTTG
1501 CGCGTGGCGT CTCTGCGATG AACATCCGAA ACTGACGTTC TGTTACAGAC TGGTCACTTG
1561 ATCTACCAGT GCGGTGGTAT CGACAAGCGT ACCATTGAGA AGTTCGAGAA GGTAAGCTTC
1621 GTTCCTTAAA TCTCCAGACG CGAGCCCAAT CTTTGCCCAT CTGCCCAGCA TCTGGCGAAC
1681 GAATGCTGTG CCGACACGAT TTTTTTTTTC ATCACCCCGC TTTCTCCTAC CCCTCCTTCG
1741 AGCGACGCAA ATTTTTTTTG CTGCCTTACG AGTTTTAGTG GGGTCGCACC TCACAACCCC
1801 ACTACTGCTC TCTGGCCGCT CCCCAGTCAC CCAACGTCAT CAACGCAGCA GTTTTCAATC
1861 AGCGATGCTA ACCATATTCC CTCGAACAGG AAGCCGCCGA ACTCGGCAAG GGTTCCTTCA
1921 AGTACGCGTG GGTTCTTGAC AAGCTCAAGG CCGAGCGTGA GCGTGGTATC ACCATCGACA
1981 TTGCCCTCTG GAAGTTCGAG ACTCCCAAGT ACTATGTCAC CGTCATTGGT ATGTTGGCAG
2041 CCATCACCTC ACTGCGTCGT TGACACATCA AACTAACAAT GCCCTCACAG ACGCTCCCGG
2101 CCACCGTGAC TTCATCAAGA ACATGATCAC TGGTACTTCC CAGGCCGACT GCGCTATCCT
2161 CATCATCGCT GCCGGTACTG GTGAGTTCGA GGCTGGTATC TCCAAGGATG GCCAGACCCG
2221 TGAGCACGCT CTGCTCGCCT ACACCCTGGG TGTCAAGCAG CTCATCGTCG CCATCAACAA
2281 GATGGACACT GCCAACTGGG CCGAGGCTCG TTACCAGGAA ATCATCAAGG AGACTTCCAA
2341 CTTCATCAAG AAGGTCGGCT TCAACCCCAA GGCCGTTGCT TTCGTCCCCA TCTCCGGCTT
2401 CAACGGTGAC AACATGCTCA CCCCCTCCAC CAACTGCCCC TGGTACAAGG CTGGGAGAA
2461 GGAGACCAAG GCTGGCAAGT TCACCGGCAA GACCCTCCTT GAGGCCATCG ACTCCATCGA
2521 GCCCCCCAAG CGTCCCACGG ACAAGCCCCT GCGTCTTCCC CTCCAGGACG TCTACAAGAT
2581 CGGTGGTATC GGAACAGTTC CCGTCGGCCG TATCGAGACT GGTGTCCTCA AGCCCGGTAT
2641 GGTCGTTACC TTCGCTCCCT CCAACGTCAC CACTGAAGTC AAGTCCGTCG AGATGCACCA
2701 CGAGCAGCTC GCTGAGGGCC AGCCTGGTGA CAACGTTGGT TTCAACGTGA AGAACGTTTC
2761 CGTCAAGGAA ATCCGCCGTG GCAACGTTGC CGGTGACTCC AAGAACGACC CCCCCATGGG
```

FIG.1C

2821 CGCCGCTTCT TTCACCGCCC AGGTCATCGT CATGAACCAC CCCGGCCAGG TCGGTGCCGG
2881 CTACGCCCCC GTCCTCGACT GCCACACTGC CCACATTGCC TGCAAGTTCG CCGAGCTCCT
2941 CGAGAAGATC GACCGCCGTA CCGGTAAGGC TACCGAGTCT GCCCCCAAGT TCATCAAGTC
3001 TGGTGACTCC GCCATCGTCA AGATGATCCC CTCCAAGCCC ATGTGCGTTG AGGCTTTCAC
3061 CGACTACCCT CCCCTGGGTC GTTTCGCCGT CCGTGACATG CGCCAGACCG TCGCTGTCGG
3121 TGTCATCAAG GCCGTCGAGA AGTCCTCTGC CGCCGCCGCN AAGGTCACCA AGTCCGCTGC
3181 CAAGGCCGCC AAGAAATAAG CGATACCCAT CATCAACACC TGATGTTCTG GGGTCCCTCG
3241 TGAGGTTTCT CCAGGTGGGC ACCACCATGC GCTCACTTCT ACGACGAAAC GATCAATGTT
3301 GCTATGCATG AGSACTCGAC TATGAATCGA GGCACGGTTA ATTGAGAGGC TGGGAATAAG
3361 GGTTCCATCA GAACTTCTCT GGGAATGCAA AACAAAAGGG AACAAAAAAA CTAGATAGAA
3421 GTGAATTCAT GACTTCGACA ACCAAAAAAA AAAAAAAAA A

FIG.1D

```
     10         20         30         40         50         60
      |          |          |          |          |          |
   1 GCCAGTGGCG ATAAGTCGTG TCTTCCGGGT TGGACTCAAG ACGATAGTTA CCGGATAAGG
  61 CGCAGCGGTC GGGCTGAACG GGGGGTTCGT GCACACAGCC CAGCTTGGAG CGAACGACCT
 121 ACACCGAACT GAGATACCTA CAGCGTGAGC TATGAGAAAG CGCCACGCTT CCCGAAGGGA
 181 GAAAGGCGGA CAGGTATCCG GTAAGCGGCA GGGTCGGAAC AGGAGAGAGA AAGAGGGANN
 241 TTCCAGGGGG AAACGCCTGG TATCTTTATA GTCCTGTTGG GTTTCGCCAC CTCTGACTTG
 301 AGCGTCGATT TTTGTGATGC TCGTCAGGGG GNGGAGCCTA TGGAAAAACG CCAGCAACGC
 361 GGCCTTTTTA CGGTTCCTGG CCTTTTGCTG GCCTTTTGCT CACATGTTCT TTCCTGCGTT
 421 ATCCCCTGAT TCTGTGGATA ACCGTATTAC CGCCTTTGAG TGAGCTGATA CCGCTCGCCG
 481 CAGCCGAACG ACCGAGCGCA GCGAGTCAGT GAGCGAGGAA GCGGAAGAGC GCCCAATACG
 541 CAAACCGCCT CTCCCCGCGC GTTGGCCGAT TCATTAATGC AGGTTAACCT GGCTTATCGA
 601 AATTAATACG ACTCACTATA GGGAGACCGG CCTCGAGCAG CTGAAGCTTG CATGCCTGCA
 661 GGTCGACTCT AGAGGATCCC CGGGTACCGA GCTCGAATTC GGTCTGAAGG ACGTGGAATG
 721 ATGGACTTAA TGACAAGAGT TGCCTGGCTA TTGAGCTCTG GTACATGGAT CTCGAACTGA
 781 GAGCGTACAA GTTACATGTA GTAAATCTAG TAGATCTCGC TGAAAGCCCT CTTTCCCGGT
 841 AGAAACACCA CCAGCGTCCC GTAGGACAAG ATCCTGTCGA TCTGAGCACA TGAATTGCTT
 901 CCCTGGATCT GGCGCTGCAT CTGTTTCCCC AGACAATGAT GGTAGCAGCG CATGGAAGAA
 961 CCCGGTTGTT CGGAATGTCC TTGTGCTAAC AGTGGCATGA TTTTACGTTG CGGCTCATCT
1021 CGCCTTGGCA CCGGACCTCA GCAAATCTTG TCACAACAGC AATCTCAAAC AGCCTCATGG
1081 TTCCCAGATT CCCTGATTCA GAACTCTAGA GCGGCAGATG TCAAACGATT CTGACCTAGT
1141 ACCTTGAGCA TCCCTTTCGG ATCCGGCCCA TGTTCTGCCT GCCCTTCTGA GCACAGCAAA
1201 CAGCCCAAAA GGCGCCGGCC GATTCCTTTC CCGGGATGCT CCGGAGTGGC ACCACCTCCC
1261 AAAACAAGCA ACCTTGAACC CCCCCCCCAA ATCAACTGAA GCGCTCTTCG CCTAACCAGC
1321 ATAAGCCCCC CCCAGGATCG TTAGGCCAAG TGGTAGGGCC AGCCAATTAG CGAGNGGCCA
1381 TTTGGAGGTC ATGGGCGCAG AATGTCCTGA CAGTGGTATG ATATTGACTG CCCGGTGTGT
1441 GTGGCATCTG GCCATAATCG CAGGCTGAGG CGAGGAAGTC TCGTGAGGAT GTCCCGACTT
1501 TGACATCATG AGGGAGTGAG AAACTGAAGA GAAGGAAAGC TTCGAAGGTT CGATAAGGGA
1565 TGATTTGCAT GGCGGGCGAC AGGATGCGAT GGCTCGTTGG GATACATAAT GCTTGGGTTG
1621 GAAGCGATTC CAGGTCGTCT TTTTTTGGTT CATCATCACA GCATCAACAA GCAACGATAC
1681 AAGCAATCCA CTGAGGATTA CCTCTCAACT CAACCACTTT CCAAACCATC TCAACTCCCT
1741 AAGATTCTTT CAGTGTATTA TCACTAGGAT TTTTCCCAAG CCGGCTTCAA AACACACAGA
1801 TAAACCACCA ACTCTACAAC CAAAGACTTT TTGATCAATC CAACAACTTC TCTCAACATG
1861 TCTGCTGCAA CCGTCACCCG CACTGCAACC GCCGCTGTTC GCAGACCCGG CTTCTTCATG
1921 CAAGTCCGAC GGATGGGACG CTCATTCGAG CACCAGCCCT TTGAGCGACT CTCCGCCACC
1981 ATGAAGCCTG CACGACCCGA CTATGCTAAG CAAGTCGTCT GGACGGCTGG CAAGTTTGTC
2041 ACTTATGTTC CTCTTTTCGG CGCCATGCTT ACCTGGCCTG CGCTCGCCAA STGGGCTCTG
2101 GACGGACACA TCGGACGGTG GTAAAAGATC AGACTCTTGT CGAGGCAACG GGGAATAGAC
2161 AGGACAGCAA AAAAGATATC TCCGGATAGA AGTGTCCATC TTTCGACTTG TATATATATA
2221 TATGCTATAC TCTGGGGGCG TTTGGATGGA CTTTGGGCAC GAAGCATACT TTGGCGCAAC
2281 GCAGATACTT TAATCTGATT CCTTTTGTTA ATTCAAAAAA AAAAAAAAAA AAAAAA
```

FIG.3B

```
        10         20         30         40         50         60
        |          |          |          |          |          |
   1 TTTGTATGGC TGGATCTCGA AAGGCCCTTG TCATCGCCAA GCGTGGCTAA TATCGAATGA
  61 GGGACACCGA CTTGCATATC TCCTGATCAT TCAAACGACA AGTGTGAGGT AGGCAATCCT
 121 CGTATCCCAT TGCTGGGCTG AAAGCTTCAC ACGTATCGCA TAAGCGTCTC CAACCAGTGC
 181 TTAGGTGACC CTTAAGGATA CTTACAGTAA GACTGTATTA AGTCAGTCAC TCTTTCACTC
 241 GGGCTTTGAA TACGATCCTC AATACTCCCG ATAACAGTAA GAGGATGATA CAGCCTGCAG
 301 TTGGCAAATG TAAGCGTAAT TAAACTCAGC TGAACGGCCC TTGTTGAAAG TCTCTCTCGA
 361 TCAAAGCAAA GCTATCCACA GACAAGGGTT AAGCAGGCTC ACTCTTCCTA CGCCTTGGAT
 421 ATGCAGCTTG GCCAGCATCG CGCATGGCCA ATGATGCACC CTTCACGGCC CAACGGATCT
 481 CCCGTTAAAC TCCCCTGTAA CTTGGCATCA CTCATCTGTG ATCCCAACAG ACTGAGTTGG
 541 GGGCTGCGGC TGGCGGATGT CGGAGCAAAG GATCACTTCA AGAGCCCAGA TCCGGTTGGT
 601 CCATTGCCAA TGGATCTAGA TTCGGCACCT TGATCTCGAT CACTGACACA TGGTGAGTTG
 661 CCCGGACGCA CCACAAGTCC CCCTGTGTCA TTGAGTCCCC ATATGCGTCT TCTCAGCGTG
 721 CAACTCTGAG ACGGATTAGT CCTCACGATG AAATTAACTT CCAGCTTAAG TTCGTAGCCT
 781 TGAATGAGTG AAGAAATTTC AAAAACAAAC TGAGTAGAGG TCTTGAGCAG CTGGGGTGGT
 841 ACGCCCCTCC TCGACTCTTG GGACATCGTA CGGCAGAGAA TCAACGGATT CACACCTTTG
 901 GGTCGAGATG AGCTGATCTC GACAGATACG TGCTTCACCA CAGCTGCAGC TACCTTTGCC
 961 CAACCATTGC GTTCCAGGAT CTTGATCTAC ATCACCGCAG CACCCGAGCC AGGACGGAGA
1021 GAACAATCCG GCCACAGAGC AGCACCGCCT TCCAACTCTG CTCCTGGCAA CGTCACACAA
1081 CCTGATATTA GATATCCACC TGGGTGATTG CCATTGCAGA GAGGTGGCAG TTGGTGATAC
1141 CGACTGGCCA TGCAAGACGC GGCCGGGCTA GCTGAAATGT CCCCGAGAGG ACAATTGGGA
1201 GCGTCTATGA CGGCGTGGAG ACGACGGGAA AGGACTCAGC CGTCATGTTG TGTTGCCAAT
1261 TTGAGATTGT TGACCGGGAA AGGGGGGACG AAGAGGATGG CTGGGTGAGG TGGTATTGGG
1321 AGGATGCATC ATTCGACTCA GTGAGCGATG TAGAGCTCCA AGAATATAAA TATCCCTTCT
1381 CTGTCTTCTC AAAATCTCCT TCCATCTTGT CCTTCATCAG CACCAGAGCC AGCCTGAACA
1441 CCTCCAGTCA ACTTCCCTTA CCAGTACATC TGAATCAACA TCCATTCTTT GAAATCTCAC
1501 CACAACCACC ATCTTCTTCA AAATGAAGTT CTTCGCCATC GCCGCTCTCT TTGCCGCCGC
1561 TGCCGTTGCC CAGCCTCTCG AGGACCGCAG CAACGGCAAC GGCAATGTTT GCCCTCCCGG
1621 CCTCTTCAGC AACCCCCAGT GCTGTGCCAC CCAAGTCCTT GGCCTCATCG GCCTTGACTG
1681 CAAAGTCCGT AAGTTGAGCC ATAACATAAG AATCCTCTTG ACGGAAATAT GCCTTCTCAC
1741 TCCTTTACCC CTGAACAGCC TCCCAGAACG TTTACGACGG CACCGACTTC CGCAACGTCT
1801 GCGCCAAAAC CGGCGCCCAG CCTCTCTGCT GCGTGGCCCC CGTTGTAAGT TGATGCCCCA
1861 GCTCAAGCTC CAGTCTTTGG CAAACCCATT CTGACACCCA GACTGCAGGC CGGCCAGGCT
```

FIG.4B

```
1921  CTTCTGTGCC AGACCGCCGT CGGTGCTTGA GATGCCCGCC CGGGGTCAAG GTGTGCCCGT
1981  GAGAAAGCCC ACAAAGTGTT GATGAGGACC ATTTCCGGTA CTGGGAAAGT TGGCTCCACG
2041  TGTTTGGGCA GGTTTGGGCA AGTTGTGTAG ATATTCCATT CGTACGCCAT TCTTATTCTC
2101  CAATATTTCA GTACACTTTT CTTCATAAAT CAAAAAGACT GCTATTCTCT TTGTGACATG
2161  CCGGAAGGGA ACAATTGCTC TTGGTCTCTG TTATTTGCAA GTAGGAGTGG GAGATTCGCC
2221  TTAGAGAAAG TAGAGAAGCT GTGCTTGACC GTGGTGTGAC TCGACGAGGA TGGACTGAGA
2281  GTGTTAGGAT TAGGTCGAAC GTTGAAGTGT ATACAGGATC GTCTGGCAAC CCACGGATCC
2341  TATGACTTGA TGCAATGGTG AAGATGAATG ACAGTGTAAG AGGAAAAGGA AATGTCCGCC
2401  TTCAGCTGAT ATCCACGCCA ATGATACAGC GATATACCTC CAATATCTGT GGGAACGAGA
2461  CATGACATAT TTGTGGGAAC AACTTCAAAC AGCGAGCCAA GACCTCAATA TGCACATCCA
2521  AAGCCAAACA TTGGCAAGAC GAGAGACAGT CACATTGTCG TCGAAAGATG GCATCGTACC
2581  CAAATCATCA GCTCTCATTA TCGCCTAAAC CACAGATTGT TTGCCGTCCC CCAACTCCAA
2641  AACGTTACTA CAAAAGACAT GGGCGAATGC AAAGACCTGA AGCAAACCC TTTTTGCGAC
2701  TCAATTCCCT CCTTTGTCCT CGGAATGATG ATCCTTCACC AAGTAAAAGA AAAAGAAGAT
2761  TGAGATAATA CATGAAAAGC ACAACGGAAA CGAAAGAACC AGGAAAAGAA TAAATCTATC
2821  ACGCACCTTG TCCCCACACT AAAACCAACA GGGGGGGTAA AATGAAAT
```

FIG.4C

```
              10         20         30         40         50         60
              |          |          |          |          |          |
   1 AAAAAGCTAG AACGAGACGA TTCCGGCCCG GCAAACCAGG CCGAGTGACG GGAGCATTTC
  61 CATGATTTCA CTCGGCAAAC TCTGGCTACA ATTTTCAGGC GGCGAGTTCC GATACAAGGG
 121 AAATCTATTA CCCACAGACG AACGGGAATC GGTGATGAGT GGTTTCTTGT AAGTCAACAT
 181 TGAGCTAGAT AATTCCGGGC GAGATCAAGA TGCCATACTT TGATTGATGA AAAATCAATG
 241 TCAGGCGTAA GTCTCTTCAA GCTCGCCCAG TCCTCTGTAT GTAACAGCAA TCGCAATTCC
 301 GAAATGTGCC GAGCCAATGG AACATGCGTG TCTTTCTCTT TTCACACACA TCCAGTTCGA
 361 GAGTCTTCTC TTCATCGTTT CATCGAATCC CTTCCCCTCC AGCTATTCAC CAGCCGAGC
 421 CCTTCAGCGC ACCAGCGTAT GTATGTACCC TCGGCTAAGA CGCAACAGAA GCATCATCAA
 481 TATACCTGAT GTACTACTAT CTACTATGAA GCCCAAAAAC CCCTTCGCAG CCCAAATGTA
 541 ACCCAAGCAA CGAATCCCCA ATAAGAGACA ATCCTCAGTG ACCCCAGAA GAGCACAGAA
 601 TCGAGCTGGT CCTGGTGGGT CGCATTGAGA CCGGTGGAGA TGCGTTCGAT TCGACTGCCG
 661 GAGCTCCCGG GAAGCCGGCA GATGGTCCCA TGCGATGCCC TGCACCGTTT TTGTGAATCG
 721 TCGGCATCGC GAGAAGTGGC CTGCTATGAC GTCGCTTGCA GCTTGGCCGC TCTGTTCGAA
 781 GTTTTTCGAT GTTTTTCTTC ATGCGGGAGA AAGAAAACAT CAGATGACAT GATTATCCGA
 841 ATGGATGGCG GGAGTTATCG TGGTGACGGC TGCTTCATGA GATGAGTATA AATGAGCTTG
 901 TTCGCTCAGC GTGTCATGGA TCTTGTCCAG CTCCAAAGCA TCGGCTTCAG CATCCATCCG
 961 CTTGAACAGA CAGGCACCAG CTTGAATCAG AAGCATACCC TTGATTTGAT ACTCTCTTGG
1021 GAAAAAACAC CACCATCTGT GTAATACTTT GATACCCCCA AAGCTCAAAC GACCGCTTGT
1081 ACATACAATA ACACCGCCAC AATGTTCGCC AACTTGACGC ACGCTACCCT GCGATTCATC
1141 GCCTTCTTCA ACCACCTGAT GATCCTGGCC TCATCAGCCA TCGTCACCGG CCTCGTATCC
1201 TGGTTCCTCG ACAAGTACGA CTACCGCGGC GTGAACATTG TCTACCAGGA AGTCATCGTA
1261 TGTCCTCCCA AGCACCACAT CAAACACACC CCATACCTTG GCTCTCCTCA GCTCCGTCGA
1321 AGCACATAAT ACTAACGCAT GCAACAACTA GGCCACCATA ACTCTGGGCT TCTGGCTCGT
1381 TGGTGCCGTC TTGCCCCTCG TTGGCAGATA CCGCGGCCAC CTGGCCCCTC TCAACCTCAT
```

FIG.5B

1441 CTTCTCCTAC CTCTGGCTCA CCTCTTTCAT CTTCTCCGCG CAGGACTGGA GCAGCGACAA
1501 GTGCAGCTTC GGCCAGCCTG GCGAGGGCCA CTGCAGCCGC AAGAAGGCCA TTGAATCCTT
1561 CAACTTTATC GCATTGTAAG TGCCTACAAG TAATTTGCTA TGTATATGGG AGAGAGAGAG
1621 AAGAAGAAGA ATATGGCTCT AACATGGCAT CTCTACAGCT TCTTCCTCCT CTGCAACACC
1681 CTGGTTGAGA TGCTCCTGCT CCGCGCCGAG TATGCTACCC CCGTTGCTGC TGCTCACAAC
1741 AAGGAGATTT CTGCCGGCCG CCCCTCTGAC AACTCTGTCT AAATAACAAT AGACATGCAT
1801 AGATGAACGG AGACCACTTC TACTTTCTTT GCGAGTTCCT GATCCGTTGA CCTGCAGGTC
1861 GACBBBBBCC GCGCTCGCAT GGTTCATCTG CTACAACAAC ACAATGACAA TCCGAACCAG
1921 TCAATAAACC TCGACAACAC GACGAGTACT TTTGCGGATA GAAAGATACC CATTACACAG
1981 GAGATCAAAT GGGGAAATTG GAAGTGTATG GATGGACGCC CGTGTATAAT GAGGTTGTGA
2041 ACGGGATGGG AGGCAATGAA TAATGGATAA TGAGGTAATG GATAGATTCG GTCGTTTTGA
2101 TACCACAGCT GCACTCTGCT CTACGTCTGT CATTAATGAT ACATACAAAT GATACCTTAT
2161 ACGCTAAAAA AAAAA

FIG.5C

```
         10         20         30         40         50         60
         |          |          |          |          |          |
   1 TCTAGAATCT CTTCGAGATG GCCGAGAAAG GCTTGTTTTT CTCTCCTTCT TCAAACTGGC
  61 CACTGTTTGT TTTCAAACTT GGGGTTTCGT GGGGCTTTTG GGGGCATGTC TGCCAGGTCT
 121 CCCGTAGGCT GGACAGCCAA AGCCTCACTA CAAACAGGCA GTTGTCAATA GATTGATGTC
 181 TGAGATGGAT GGTTTTATGT TTGGGGGAGG TCATGTATGT ATTTATCTAT ATTTGCAAAG
 241 ATGATCCATG AGTCAGACTT GCACAGGTTT CTCGTGCGCT GGATAAATCT TGTTGGAGTG
 301 CGGGTGAGGT GGTGGATGGC ATTCAACCCA CAGCAACACT TGCCCAGGGG GATGTACTGC
 361 AGCGATTTGT TTCCCTTCGA GTATTAGATG ATGATGCCGA ACAGACAAAT TTGAGCCTCG
 421 CTGCTCTCGG ATGTCGGGTT TCTCTTGTGT GCCGGTGATG TGTGATGGCC TGGCCCGCAA
 481 AGAGAGCGAA AAACATGCTC AAAATGTAGC ACACGGCGAC TTCTCGGACA CTTGCGTACC
 541 TTGAGAGACA AGCAGACTAC AGGGATGACG AGTAATACGA CAGAGCGATA CGACACAGCT
 601 ATACGACACA GCTAAGAAAA TAAAGGTATT AGTACTACTA ATTGATTACC TACTACCTAG
 661 ATATATACTA TACCTTATAT TTTATATGTG TGTGTGTGTG TATGTATATG CCTTACCTTA
 721 TGCTTCGCAA AGAAGAGAAA CTAAAACGCC TCCTGGCTAC CTACCTACCT CTACCTTGTA
 781 AGAGATGGAA TAATGTGGCC GCGCGTAAAG TAGGTACTGG ATATACAGGT CCTGAACATG
 841 GCCCTGAATC CTGCCAGGCA GCCACCTCAC CCCTTCCGCA GGTATTTATG TAGCCCACAG
 901 CTCCTCCAGA GACGATGCCG AGATGCCTCA TGCAGTCTAC CTACAAAGCC AGCAGTTTCA
 961 CGCTTGACTC TCACTCTTGA TTGAATTCCC TCCCTCCCAT AATACCAATT GGCGTTCAAC
1021 GATTGCCAGC AGAATGGCCG CCCAACACGA CGTCGAGGCC ATGGCAAAGT CCATGTCCGA
1081 CTTTTTCAAG GACACGGCCC AAAAGCAGGA CTCGACCAAG CATGACTTTG TCCAAGCCTC
1141 GCACGGCATC ATGAGGGCCA TTGTCGAGCC GCTCGTCACC CAGATGGGCT TCCGCGAGAC
1201 CCTCACCGAG CCCGTCGTCT TGCTCGACAG CGCGTGCGGA GCGGGCGTGC TGACGCAGGA
1261 GGTGCAGGCG GCGCTGCCAA AGGAGCTTCT GGAGAGGAGC TCGTTTACGT GTGCGGACAA
1321 TGCCGAGGGC TTGGTGGACG TGGTGAAGAG GAGGATTGAT GAGGAGAAGT GGGTGAATGC
1381 AGAGGCCAAG GTCCTTGATG CCCTGGTGAG TATATACATA TATATCTATA TCTATATAGA
1441 TATATATATG CCTTTGACTC CCCCCTTTAC ATGTCCTACG GCTGCTGATT GATTGATTGA
```

FIG.6B

1501 TGTGGTGATG GTGATGTCCC AGAACACGGG GCTCCCAGAC AACTCCTTCA CCCATGTGGG
1561 CATTGCCCTG GCACTGCACA TCATCCCCGA TCCAGATGCC GTCGTCAAAG GTAAACAATC
1621 ACCAGCGTCA CTGCAAAGAG AGATTACGGG ATATCATATA CTGAAACCAA AGCCCAGACT
1681 GCATCAGAAT GCTCAAGCCA GGCGGCATCT TTGGCGCATC GACATGGCCC AAGGCCAGCG
1741 CCGACATGTT CTGGATCGCC GACATGCGCA CCGCCCTGCA GTCGCTCCCC TTTGACGCGC
1801 CGCTGCCAGA CCCGTTCCCC ATGCAGCTGC ACACCTCGGG CCACTGGGAC GACGCCGCCT
1861 GGGTCGAGAA GCATCTCGTC GAGGATCTGG GGCTGGCCAA CGTCTGTGTG AGGGAGCCGG
1921 CGGGCGAGTA CAGCTTTGCG AGCGCGGACG AGTTCATGGC GACGTTTCAG ATGATGCTGC
1981 CGTGGATTAT GAAGACGTTT TGGAGCGAGG AGGTGAGGGA GAAGCATTCG GTCGACGAGG
2041 TCAAGGAGTT GGTGAAGAGG CATCTGGAGG ACAAGTATGG GGGGAAGGGA TGGACCATTA
2101 AGTGGCGGGT GATTACCATG ACTGCGACTG CGAGCAAGTG AGGGAGGGCA TCTGCTCATG
2161 ATTATGTGAC AGCGAGCCAG TAGAGAGCCA TATTGTTGTC TTCAGAATGT GAGGACCGTG
2221 ATGGTTGGTG TTTGTTGGAG TGATAACTCG TGGGTGTTGC TATTTGCATG TGAGACGATG
2281 AACCATGCGC ACCAGCCACA ATCACTGTCC CCCACCTTAC CTACCAACTT CAAGTTACCA
2341 CCTTACCTTT ACCTGATCTA GCACTGTGGC GCAGCTTGGT TTGACTGCTA GGTACCTACC
2401 TAGTAGTAAT CAGGTACATT CTTCATCCCT GTGTCCTGGT GTCGCAGTTG CAGCTTGTCT
2461 TATCGCTGTG GCCACGCATC GAGTGGCAGC ATCTTCAACT TCAAGTCCCG TCGGTCGCAC
2521 TCTGGCCACG TCGCAGATGG ATCGCAGCGG GATCTGAACC GCTCGCTCGG CAACTGATAC
2581 CAAGTCAACA AACACACGAG ACGACGGGAC GCTGATATAA NNNNGAGGAG GGTAAGAGAA
2641 CTCTACGAGG GGCGGAAACT TGGTCCGACA ATTTCCCTCC CATCTTCACC CTCGACTCGA
2701 ACTCGAACTC GATAGCCGCA CCCTCGACCG ATTGCCC

FIG.6C

```
CCCCCCTATC TTAGTCCTTC TTGTTGTCCC AAAATGGCGC CCTCAGTTAC ACTGCCGTTG
ACCACGGCCA TCCTGGCCAT TGCCCGGCTC GTCGCCGCCC AGCAACCGGG TACCAGCACC
CCCGAGGTCC ATCCCAAGTT GACAACCTAC AAGTGTACAA AGTCCGGGGG GTGCGTGGCC
CAGGACACCT CGGTGGTCCT TGACTGGAAC TACCGCTGGA TGCACGACGC AAACTACAAC
TCGTGCACCG TCAACGGCGG CGTCAACACC ACGCTCTGCC CTGACGAGGC GACCTGTGGC
AAGAACTGCT TCATCGAGGG CGTCGACTAC GCCGCCTCGG GCGTCACGAC CTCGGGCAGC
AGCCTCACCA TGAACCAGTA CATGCCCAGC AGCTCTGGCG GCTACAGCAG CGTCTCTCCT
CGGCTGTATC TCCTGGACTC TGACGGTGAG TACGTGATGC TGAAGCTCAA CGGCCAGGAG
CTGAGCTTCG ACGTCGACCT CTCTGCTCTG CCGTGTGGAG AGAACGGCTC GCTCTACCTG
TCTCAGATGG ACGAGAACGG GGGCGCCAAC CAGTATAACA CGGCCGGTGC CAACTACGGG
AGCGGCTACT GCGATGCTCA GTGCCCCGTC CAGACATGGA GGAACGGCAC CCTCAACACT
AGCCACCAGG GCTTCTGCTG CAACGAGATG GATATCCTGG AGGGCAACTC GAGGGCGAAT
GCCTTGACCC CTCACTCTTG CACGGCCACG GCCTGCGACT CTGCCGGTTG CGGCTTCAAC
CCCTATGGCA GCGGCTACAA AAGCTACTAC GGCCCCGGAG ATACCGTTGA CACCTCCAAG
ACCTTCACCA TCATCACCCA GTTCAACACG GACAACGGCT CGCCCTCGGG CAACCTTGTG
AGCATCACCC GCAAGTACCA GCAAAACGGC GTCGACATCC CCAGCGCCCA GCCCGGCGGC
GACACCATCT CGTCCTGCCC GTCCGCCTCA GCCTACGGCG GCCTCGCCAC CATGGGCAAG
GCCCTGAGCA GCGGCATGGT GCTCGTGTTC AGCATTTGGA ACGACAACAG CCAGTACATG
AACTGGCTCG ACAGCGGCAA CGCCGGCCCC TGCAGCAGCA CCGAGGGCAA CCCATCCAAC
ATCCTGGCCA ACAACCCCAA CACGCACGTC GTCTTCTCCA ACATCCGCTG GGGAGACATT
GGGTCTACTA CGAACTCGAC TGCGCCCCG CCCCCGCCTG CGTCCAGCAC GACGTTTTCG
ACTACACGGA GGAGCTCGAC GACTTCGAGC AGCCCGAGCT GCACGCAGAC TCACTGGGGG
CAGTGCGGTG GCATTGGGTA CAGCGGGTGC AAGACGTGCA CGTCGGGCAC TACGTGCCAG
TATAGCAACG ACTACTACTC GCAATGCCTT TAGAGCGTTG ACTTGCCTCT GGTCTGTCCA
GACGGGGGCA CGATAGAATG CGGGCACGCA GGGAGCTCGT AGACATTGGG CTTAATATAT
AAGACATGCT ATGTTGTATC TACATTAGCA AATGACAAAC AAATGAAAAA GAACTTATCA
AGCAAAAAAA AAAAAAAAAA AAAAAAAA
```

FIG.7B

```
GGACCTACCC AGTCTCACTA CGGCCAGTGC GGCGGTATTG GCTACAGCGG CCCCACGGTC
TGCGCCAGCG GCACAACTTG CCAGGTCCTG AACCCTTACT ACTCTCAGTG CCTGTAAAGC
TCCGTGCGAA AGCCTGACGC ACCGGTAGAT TCTTGGTGAG CCCGTATCAT GACGGCGGCG
GGAGCTACAT GGCCCCGGGT GATTTATTTT TTTTGTATCT ACTTCTGACC CTTTTCAAAT
ATACGGTCAA CTCATCTTTC ACTGGAGATG CGGCCTGCTT GGTATTGCGA TGTTGTCAGC
TTGGCAAATT GTGGCTTTCG AAAACACAAA ACGATTCCTT AGTAGCCATG CATTTTAAGA
TAACGGAATA GAAGAAAGAG GAAATTAAAA AAAAAAAAAA AACAAACATC CCGTTCATAA
CCCGTAGAAT CGCCGCTCTT CGTGTATCCC AGTACCACGT CAAAGGTATT CATGATCGTT
CAATGTTGAT ATTGTTCCGC CAGTATGGCT CCACCCCCAT CTCCGCGAAT CTCCTCTTCT
CGAACGCGGT AGTGGCTGCT GCCAATTGGT AATGACCATA GGGAGACAAA CAGCATAATA
GCAACAGTGG AAATTAGTGG CGCAATAATT GAGAACACAG TGAGACCATA GCTGGCGGCC
TGGAAAGCAC TGTTGGAGAC CAACTTGTCC GTTGCGAGGC CAACTTGCAT TGCTGTCAAG
ACGATGACAA CGTAGCCGAG GACCC
```

FIG.7C

```
        EcoRI  10         20         30         40         50         60
        GAATTCTCAC GGTGAATGTA GGCCTTTTGT AGGGTAGGAA TTGTCACTCA AGCACCCCCA    60

ACCTCCATTA CGCCTCCCCC ATAGAGTTCC CAATCAGTGA GTCATGGCAC TGTTCTCAAA   120

TAGATTGGGG AGAAGTTGAC TTCCGCCCAG AGCTGAAGGT CGCACAACCG CATGATATAG   180

GGTCGGCAAC GGCAAAAAAG CACGTGGCTC ACCGAAAAGC AAGATGTTTG CGATCTAACA   240

TCCAGGAACC TGGATACATC CATCATCACG CACGACCACT TTGATCTGCT GGTAAACTCG   300

TATTCGCCCT AAACCGAAGT GCGTGGTAAA TCTACACGTG GGCCCCTTTC GGTATACTGC   360

GTGTGTCTTC TCTAGGTGCA TTCTTTCCTT CCTCTAGTGT TGAATTGTTT GTGTTGGGAG   420

TCCGAGCTGT AACTACCTCT GAATCTCTGG AGAATGGTGG ACTAACGACT ACCGTGCACC   480

TGCATCATGT ATATAATAGT GATCCTGAGA AGGGGGGTTT GGAGCAATGT GGGACTTTGA   540

TGGTCATCAA ACAAAGAACG AAGACGCCTC TTTTGCAAAG TTTTGTTTCG GCTACGGTGA   600

AGAACTGGAT ACTTGTTGTG TCTTCTGTGT ATTTTGTGG CAACAAGAGG CCAGAGACAA    660
                                                    -1505          XbaI
        TCTATTCAAA CACCAAGCTT GCTCTTTTGA GCTACAAGAA CCTGTGGGGT ATATATCTAG   720

AGTTGTGAAG TCGGTAATCC CGCTGTATAG TAATACGAGT CGCATCTAAA TACTCCGAAG   780

CTGCTGCGAA CCCGGAGAAT CGAGATGTGC TGGAAAGCTT CTAGCGAGCG GCTAAATTAG   840

CATGAAAGGC TATGAGAAAT TCTGGAGACG GCTTGTTGAA TCATGGCGTT CCATTCTTCG   900

ACAAGCAAAG CGTTCCGTCG CAGTAGCAGG CACTCATTCC CGAAAAAACT CGGAGATTCC   960

TAAGTAGCGA TGGAACCGGA ATAATATAAT AGGCAATACA TTGAGTTGCC TCGACGGTTG  1020

CAATGCAGGG GTACTGAGCT TGGACATAAC TGTTCCGTAC CCCACCTCTT CTCAACCTTT  1080

GGCGTTTCCC TGATTCAGCG TACCCGTACA AGTCGTAATC ACTATTAACC CAGACTGACC  1140

GGACGTGTTT TGCCCTTCAT TTGGAGAAAT AATGTCATTG CGATGTGTAA TTTGCCTGCT  1200
                 -1001
        TGACCGACTG GGGCTGTTCG AAGCCCGAAT GTAGGATTGT TATCCGAACT CTGCTCGTAG  1260
```

FIG.13B

```
AGGCATGTTG TGAATCTGTG TCGGGCAGGA CACGCCTCGA AGGTTCACGG CAAGGGAAAC    1320

CACCGATAGC AGTGTCTAGT AGCAACCTGT AAAGCCGCAA TGCAGCATCA CTGGAAAATA    1380

CAAACCAATG GCTAAAAGTA CATAAGTTAA TGCCTAAAGA AGTCATATAC CAGCGGCTAA    1440
                                                -720
                                                  |
TAATTGTACA ATCAAGTGGC TAAACGTACC GTAATTTGCC AACGCGTTGT GGGGTTGCAG    1500

AAGCAACGGC AAAGCCCACT TCCCACGTTT GTTTCTTCAC TCAGTCCAAT CTCAGCTGGT    1560

GATCCCCCAA TTGGGTCGCT TGTTTGTTCC GGTGAAGTGA AAGAAGACAG AGGTAAGAAT    1620

GTCTGACTCG GAGCGTTTTG CATACAACCA AGGGCAGTGA TGGAAGACAG TGAAATGTTG    1680

ACATTCAAGG AGTATTTAGC CAGGGATGCT TGAGTGTATC GTGTAAGGAG GTTTGTCTGC    1740

CGATACGACG AATACTGTAT AGTCACTTCT GATGAAGTGG TCCATATTGA AATGTAAGTC    1800

GGCACTGAAC AGGCAAAAGA TTGAGTTGAA ACTGCCTAAG ATCTCGGGCC CTCGGGCTTC    1860

GGCTTTGGGT GTACATGTTT GTGCTCCGGG CAAATGCAAA GTGTGGTAGG ATCGACACAC    1920

TGCTGCCTTT ACCAAGCAGC TGAGGGTATG TGATAGGCAA ATGTTCAGGG GCCACTGCAT    1980

GGTTTCGAAT AGAAAGAGAA GCTTAGCCAA GAACAATAGC CGATAAAGAT AGCCTCATTA    2040

AACGAAATGA GCTAGTAGGC AAAGTCAGCG AATGTGTATA TATAAAGGTT CGAGGTCCGT    2100

GCCTCCCTCA TGCTCTCCCC ATCTACTCAT CAACTCAGAT CCTCCAGGAG ACTTGTACAC    2160

CATCTTTTGA GGCACAGAAA CCCAATAGTC AACCGCGGAC TGCGCATAT G             2211
                                    KspI
```

FIG.13C

```
GGCGGTATTG GCTACAGCGG CCCCACGGTC TGCGCCAGCG GCACAACTTG CCAGGTCCTG      60

AACCCTTACT ACTCTCAGTG CCTGTAAAGC TCCGTGCGAA AGCCTGACGC ACCGGTAGAT     120

TCTTGGTGAG CCCGTATCAT GACGGCGGCG GGAGCTACAT GGCCCCGGGT GATTTATTTT    180

TTTTGTATCT ACTTCTGACC CTTTTCAAAT ATACGGTCAA CTCATCTTTC ACTGGAGATG    240

CGGCCTGCTT GGTATTGCGA TGTTGTCAGC TTGGCAAATT GTGGCTTTCG AAAACACAAA    300
                       Nsi I    BamHI
ACGATTCCTT AGTAGCCATG CATCGGGATC CTTTAAGATA ACGGAATAGA AGAAAGAGGA    360

AATTAAAAAA AAAAAAAAAA CAAACATCCC GTTCATAACC CGTAGAATCG CCGCTCTTCG    420

TGTATCCCAG TACCACGGCA AAGGTATTTC ATGATCGTTC AATGTTGATA TTGTTCCCGC    480

CAGTATGGCT GCACCCCCAT CTCCGCGAAT CTCCTCTTCT CGAACGCGGT AGTGGCGCGC    540

CAATTGGTAA TGACCATAGG GAGACAAACA GCATAATAGC AACAGTGGAA ATTAGTGGCG    600

CAATAATTGA GAACACAGTG AGACCATAGC TGGCGGCCTG GAAAGCACTG TTGGAGACCA    660

ACTTGTCCGT TGCGAGGCCA ACTTGCATTG CTGTCAAGAC GATGACAACG TAGCCGAGGA    720

CCGTCACAAG GGACGCAAAG TTGTCGCGGA TGAGGTCTCC GTAGATGGCA TAGCCGGCAA    780

TCCGAGAGTA GCCTCTCAAC AGGTGGCCTT TTCGAAACCG GTAAACCTTG TTCAGACGTC    840

CTAGCCGCAG CTCACCGTAC CAGTATCGAG GATTGACGGC AGAATAGCAG TGGCTCTCCA    900

GGATTTGACT GGACAAAATC TTCCAGTATT CCCAGGTCAC AGTGTCTGGC AGAAGTCCCT    960

TCTCGCGTGC ANTCGAAAGT CGCTATAGTG CGCAATGAGA GCACAGTAGG AGAATAGGAA   1020

CCCGCGAGCA CATTGTTCAA TCTCCACATG AATTGGATGA CTGCTGGGCA GAATGTGCTG   1080

CCTCCAAAAT CCTGCGTCCA ACAGATACTC TGGCAGGGGC TTCAGATGAA TGCCTCTGGG   1140

CCCCCAGATA AGATGCAGCT CTGGATTCTC GGTTACNATG ATATCGCGAG AGAGCACGAG   1200

TTGGTGATGG AGGGACAGGA GGCATAGGTC GCGCAGGCCC ATAACCAGTC TTGCACAGCA   1260

TTGATCTTAC CTCACGAGGA GCTCCTGATG CAGAAACTCC TCCATGTTGC TGATTGGGTT   1320
```

FIG.13D

| | |
|---|---|
| GAGAATTTCA TCGCTCCTGG ATCGTATGGT TGCTGGCAAG ACCCTGCTTA ACCGTGCCGT | 1380 |
| GTCATGGTCA TCTCTGGTGG CTTCGTCGCT GGCCTGTCTT TGCAATTCGA CAGCAAATGG | 1440 |
| TGGAGATCTC TCTATCGTGA CAGTCATGGT AGCGATAGCT AGGTGTCGTT GCACGCACAT | 1500 |
| AGGCCGAAAT GCGAAGTGGA AAGAATTTCC CGGNTGCGGA ATGAAGTCTC GTCATTTTGT | 1560 |

<u>BamHI</u>

| | |
|---|---|
| ACTCGTACTC GACACCTCCA CCGAAGTGTT AATAATGGAT CCACGATGCC AAAAAGCTTG | 1620 |

<u>SphI</u>
<u>TGCATGC</u>                                                                                      1627

FIG.13E

```
              10         20         30         40         50         60
               |          |          |          |          |          |
   1 GAATTCTCAC GGTGAATGTA GGCCTTTTGT AGGGTAGGAA TTGTCACTCA AGCACCCCCA
  61 ACCTCCATTA CGCCTCCCCC ATAGAGTTCC CAATCAGTGA GTCATGGCAC TGTTCTCAAA
 121 TAGATTGGGG AGAAGTTGAC TTCCGCCCAG AGCTGAAGGT CGCACAACCG CATGATATAG
 181 GGTCGGCAAC GGCAAAAAAG CACGTGGCTC ACCGAAAAGC AAGATGTTTG CGATCTAACA
 241 TCCAGGAACC TGGATACATC CATCATCACG CACGACCACT TTGATCTGCT GGTAAACTCG
 301 TATTCGCCCT AAACCGAAGT GCGTGGTAAA TCTACACGTG GGCCCCTTTC GGTATACTGC
 361 GTGTGTCTTC TCTAGGTGCA TTCTTTCCTT CCTCTAGTGT TGAATTGTTT GTGTTGGGAG
 421 TCCGAGCTGT AACTACCTCT GAATCTCTGG AGAATGGTGG ACTAACGACT ACCGTGCACC
 481 TGCATCATGT ATATAATAGT GATCCTGAGA AGGGGGGTTT GGAGCAATGT GGGACTTTGA
 541 TGGTCATCAA ACAAAGAACG AAGACGCCTC TTTTGCAAAG TTTTGTTTCG GCTACGGTGA
 601 AGAACTGGAT ACTTGTTGTG TCTTCTGTGT ATTTTTGTGG CAACAAGAGG CCAGAGACAA
 661 TCTATTCAAA CACCAAGCTT GCTCTTTTGA GCTACAAGAA CCTGTGGGGT ATATATCTAG
 721 TGGCCAGAAT GCCTAGGTCA CCTCTAGAGA GTTGAAACTG CCTAAGATCT CGGGCCCTCG
 781 GGCTTCGGCT TTGGGTGTAC ATGTTTGTGC TCCGGGCAAA TGCAAAGTGT GGTAGGATCG
 841 ACACACTGCT GCCTTTACCA AGCAGCTGAG GGTATGTGAT AGGCAAATGT TCAGGGGCCA
 901 CTGCATGGTT TCGAATAGAA AGAGAAGCTT AGCCAAGAAC AATAGCCGAT AAAGATAGCC
 961 TCATTAAACG AAATGAGCTA GTAGGCAAAG TCAGCGAATG TGTATATATA AAGGTTCGAG
1021 GTCCGTGCCT CCCTCATGCT CTCCCCATCT ACTCATCAAC TCAGATCCTC CAGGAGACTT
1081 GTACACCATC TTTTGAGGCA CAGAAACCCA ATAGTCAACC GCGGACTGCG CATCATG
```

FIG. 15B

- RESTRICTION SITES MARKED WITH * ARE NOT SINGLE SITES
- TWO ADDITIONAL EcoRI -SITES IN THE cbh1-GENE

```
                                              KspI
                                           ┌──────┐
                                           CCGCGG ACTG CGCATC ATGT         1740

ATCGGAAGTT GGCCGTCATC TCGGCCTTCT TGGCCACAGC TCGTGCTCAG TCGGCCTGCA         1800

CTCTCCAATC GGAGACTCAC CCGCCTCTGA CATGGCAGAA ATGCTCGTCT GGTGGCACTT         1860

GCACTCAACA GACAGGCTCC GTGGTCATCG ACGCCAACTG GCGCTGGACT CACGCTACGA         1920

ACAGCAGCAC GAACTGCTAC GATGGCAACA CTTGGAGCTC GACCCTATGT CCTGACAACG         1980

AGACCTGCGC GAAGAACTGC TGTCTGGACG GTGCCGCCTA CGCGTCCACG TACGGAGTTA         2040

CCACGAGCGG TAACAGCCTC TCCATTGGCT TTGTCACCCA GTCTGCGCAG AAGAACGTTG         2100

GCGCTCGCCT TTACCTTATG GGCAGCGACA CGACCTACCA GGAATTCACC CTGCTTGGCA         2160

ACGAGTTCTC TTTCGATGTT GATGTTTCGC AGCTGCCGTA AGTGACTTAC CATGAACCCC         2220

TGACGTATCT TCTTGTGGGC TCCCAGCTGA CTGGCCAATT TAAGGTGCGG CTTGAACGGA         2280

GCTCTCTACT TCGTGTCCAT GGACGCGGAT GGTGGCGTGA GCAAGTATCC CACCAACACC         2340

GCTGGCGCCA AGTACGGCAC GGGGTACTGT GACAGCCAGT GTCCCCGCGA TCTGAAGTTC         2400

ATCAATGGCC AGGCCAACGT TGAGGGCTGG GAGCCGTCAT CCAACAACGC AAACACGGGC         2460

ATTGGAGGAC ACGGAAGCTG CTGCTCTGAG ATGGATATCT GGGAGGCCAA CTCCATCTCC         2520

GAGGCTCTTA CCCCCCACCC TTGCACGACT GTCGGCCAGG AGATCTGCGA GGGTGATGGG         2580

TGCGGCGGAA CTTACTCCGA TAACAGATAT GGCGGCACTT GCGATCCCGA TGGCTGCGAC         2640

TGGAACCCAT ACCGCCTGGG CAACACCAGC TTCTACGGCC CTGGCTCAAG CTTTACCCTC         2700

GATACCACCA AGAAATTGAC CGTTGTCACC CAGTCCGAGA CGTCGGGTGC CATCAACCGA         2760

TACTATGTCC AGAATGGCGT CACTTTCCAG CAGCCCAACG CCGAGCTTGG TAGTTACTCT         2820

GGCAACGAGC TCAACGATGA TTACTGCACA GCTGAGGAGG CAGAATTCGG CGGATCCTCT         2880

TTCTCAGACA AGGGCGGCCT GACTCAGTTC AAGAAGGCTA CCTCTGGCGG CATGGTTCTG         2940

GTCATGAGTC TGTGGGATGA TGTGAGTTTG ATGGACAAAC ATGCGCGTTG ACAAAGAGTC         3000
```

FIG.16B

```
AAGCAGCTGA CTGAGATGTT ACAGTACTAC GCCAACATGC TGTGGCTGGA CTCCACCTAC    3060

CCGACAAACG AGACCTCCTC CACACCCGGT GCCGTGCGCG AAGCTGCTC  CACCAGCTCC    3120

GGTGTCCCTG CTCAGGTCGA ATCTCAGTCT CCCAACGCCA AGGTCACCTT CTCCAACATC    3180

AAGTTCGGAC CCATTGGCAG CACCGGCAAC CCTAGCGGCG GCAACCCTCC CGGCGGAAAC    3240

CCGCCTGGCA CCACCACCAC CCGCCGCCCA GCCACTACCA CTGGAAGCTC TCCCGGACCT    3300

ACCCAGTCTC ACTACGGCCA GTGCGGCGGT ATTGGCTACA GCGGCCCCAC GGTCTGCGCC    3360

AGCGGCACAA CTTGCCAGGT CCTGAACCCT TACTACTCTC AGTGCCTGTA AAGCTCCGTG    3420

CGAAAGCCTG ACGCACCGGT AGATTCTTGG TGAGCCCGTA TCATGACGGC GGCGGGAGCT    3480

ACATGGCCCC GGGTGATTTA TTTTTTTTGT ATCTACTTCT GACCCTTTTC AAATATACGG    3540
       XmaI
```

FIG.16C

| 41A UNDILUTED | 41A 1:5 | 41A 1:50 | 41B UNDILUTED | 41B 1:5 | 41B 1:50 |
|---|---|---|---|---|---|
| 41E UNDILUTED | 41E 1:5 | 41E 1:50 | 35A UNDILUTED | 35A 1:5 | 35A 1:50 |
| 35B UNDILUTED | 35B 1:5 | 35B 1:50 | 35C UNDILUTED | 35C 1:5 | 35C 1:50 |
| 24A UNDILUTED | 24A 1:5 | 24A 1:50 | 24B UNDILUTED | 24B 1:5 | 24B 1:50 |
| 39A UNDILUTED | 39A 1:5 | 39A 1:50 | 39B UNDILUTED | 39B 1:5 | 39B 1:50 |
| 39C UNDILUTED | 39C 1:5 | 39C 1:50 | 32D UNDILUTED | 32D 1:5 | 32D 1:50 |
| CBHI NEGATIVE STRAIN UNDILUTED | HOST STRAIN UNDILUTED | BUFFER | HOST STRAIN CELLULOSE MEDIUM 1:20 | HOST STRAIN CELLULOSE MEDIUM 1:40 | HOST STRAIN CELLULOSE MEDIUM 1:80 |
| CBHI NEGATIVE STRAIN 1:5 | HOST STRAIN 1:5 | CBHI PROTEIN 200 ng | CBHI PROTEIN 100 ng | CBHI PROTEIN 50 ng | CBHI PROTEIN 25 ng |

FIG. 17B

```
        10         20         30         40         50         60
         |          |          |          |          |          |
   1 GAATTCTCAC GGTGAATGTA GGCCTTTTGT AGGGTAGGAA TTGTCACTCA AGCACCCCCA
  61 ACCTCCATTA CGCCTCCCCC ATAGAGTTCC CAATCAGTGA GTCATGGCAC TGTTCTCAAA
 121 TAGATTGGGG AGAAGTTGAC TTCCGCCCAG AGCTGAAGGT CGCACAACCG CATGATATAG
 181 GGTCGGCAAC GGCAAAAAAG CACGTGGCTC ACCGAAAAGC AAGATGTTTG CGATCTAACA
 241 TCCAGGAACC TGGATACATC CATCATCACG CACGACCACT TTGATCTGCT GGTAAACTCG
 301 TATTCGCCCT AAACCGAAGT GCGTGGTAAA TCTACACGTG GGCCCCTTTC GGTATACTGC
 361 GTGTGTCTTC TCTAGGTGCA TTCTTTCCTT CCTCTAGTGT TGAATTGTTT GTGTTGGGAG
 421 TCCGAGCTGT AACTACCTCT GAATCTCTGG AGAATGGTGG ACTAACGACT ACCGTGCACC
 481 TGCATCATGT ATATAATAGT GATCCTGAGA AGGGGGGTTT GGAGCAATGT GGGACTTTGA
 541 TGGTCATCAA ACAAAGAACG AAGACGCCTC TTTTGCAAAG TTTTGTTTCG GCTACGGTGA
 601 AGAACTGGAT ACTTGTTGTG TCTTCTGTGT ATTTTGTGG CAACAAGAGG CCAGAGACAA
 661 TCTATTCAAA CACCAAGCTT GCTCTTTTGA GCTACAAGAA CCTGTGGGGT ATATATCTAG
 721 TGGCCAGAAT GCCTAGGTCA CCTCTAAAGG TACCCTGCAG CTCGAGCTAG AGTTGTGAAG
 781 TCGGTAATCC CGCTGTATAG TAATACGAGT CGCATCTAAA TACTCCGAAG CTGCTGCGAA
 841 CCCGGAGAAT CGAGATGTGC TGGAAAGCTT CTAGCGAGCG GCTAAATTAG CATGAAAGGC
 901 TATGAGAAAT TCTGGAGACG GCTTGTTGAA TCATGGCGTT CCATTCTTCG ACAAGCAAAG
 961 CGTTCCGTCG CAGTAGCAGG CACTCATTCC CGAAAAAACT CGGAGATTCC TAAGTAGCGA
1021 TGGAACCGGA ATAATATAAT AGGCAATACA TTGAGTTGCC TCGACGGTTG CAATGCAGGG
1081 GTACTGAGCT GGACATAAC TGTTCCGTAC CCCACCTCTT CTCAACCTTT GGCGTTTCCC
1141 TGATTCAGCG TACCCGTACA AGTCGTAATC ACTATTAACC CAGACTGACC GGACGTGTTT
1201 TGCCCTTCAT TTGGAGAAAT AATGTCATTG CGATGTGTAA TTTGCCTGCT TGACCGACTG
1261 GGGCTGTTCG AAGCCCGAAT GTAGGATTGT TATCCGAACT CTGCTCGTAG AGGCATGTTG
1321 TGAATCTGTG TCGGGCAGGA CACGCCTCGA AGGTTCACGG CAAGGGAAAC CACCGATAGC
1381 AGTGTCTAGT AGCAACCTGT AAAGCCGCAA TGCAGCATCA CTGGAAAATA CAAACCAATG
1441 GCTAAAAGTA CATAAGTTAA TGCCTAAAGA AGTCATATAC CAGCGGCTAA TAATTGTACA
1501 ATCAAGTGGC TAAACGTACC GTAATTTGCC AACGCGTTTC TAGATTGCAG AAGCACGGCA
```

FIG. 18B

1561 AAGCCCACTT ACCCACGTTT GTTTCTTCAC TCAGTCCAAT CTCAGCTGGT GATCCCCCAA
1621 TTGGGTCGCT TGTTTGTTCC GGTGAAGTGA AAGAAGACAG AGGTAAGAAT GTCTGACTCG
1681 GAGCGTTTTG CATACAACCA AGGGCAGTGA TGGAAGACAG TGAAATGTTG ACATTCAAGG
1741 AGTATTTAGC CAGGGATGCT TGAGTGTATC GTGTAAGGAG GTTTGTCTGC CGATACGACG
1801 AATACTGTAT AGTCACTTCT GATGAAGTGG TCCATATTGA AATGTAAGTC GGCACTGAAC
1861 AGGCAAAAGA TTGAGTTGAA ACTGCCTAAG ATCTCGGGCC CTCGGGCTTC GGCTTTGGGT
1921 GTACATGTTT GTGCTCCGGG CAAATGCAAA GTGTGGTAGG ATCGACACAC TGCTGCCTTT
1981 ACCAAGCAGC TGAGGGTATG TGATAGGCAA ATGTTCAGGG GCCACTGCAT GGTTTCGAAT
2041 AGAAAGAGAA GCTTAGCCAA GAACAATAGC CGATAAAGAT AGCCTCATTA AACGAAATGA
2101 GCTAGTAGGC AAAGTCAGCG AATGTGTATA TATAAAGGTT CGAGGTCCGT GCCTCCCTCA
2161 TGCTCTCCCC ATCTACTCAT CAACTCAGAT CCTCCAGGAG ACTTGTACAC CATCTTTTGA
2221 GGCACAGAAA CCCAATAGTCAACCGCGGAC TGCGCATCAT G

FIG.18C

```
     10         20         30         40         50         60
      |          |          |          |          |          |
   1 CAATTCTCAC GGTGAATGTA GGCCTTTTGT AGGGTAGGAA TTGTCACTCA AGCACCCCCA
  61 ACCTCCATTA CGCCTCCCCC ATAGAGTTCC CAATCAGTGA GTCATGGCAC TGTTCTCAAA
 121 TAGATTGGGG AGAAGTTGAC TTCCGCCCAG AGCTGAAGGT CGCACAACCG CATGATATAG
 181 GGTCGGCAAC GGCAAAAAAG CACGTGGCTC ACCGAAAAGC AAGATGTTTG CGATCTAACA
 241 TCCAGGAACC TGGATACATC CATCATCACG CACGACCACT TTGATCTGCT GGTAAACTCG
 301 TATTCGCCCT AAACCGAAGT GCGTGGTAAA TCTACACGTG GGCCCCTTTC GGTATACTGC
 361 GTGTGTCTTC TCTAGGTGCA TTCTTTCCTT CCTCTAGTGT TGAATTGTTT GTGTTGGGAG
 421 TCCGAGCTGT AACTACCTCT GAATCTCTGG AGAATGGTGG ACTAACGACT ACCGTGCACC
 481 TGCATCATGT ATATAATAGT GATCCTGAGA AGGGGGGTTT GGAGCAATGT GGGACTTTGA
 541 TGGTCATCAA ACAAAGAACG AAGACGCCTC TTTTGCAAAG TTTTGTTTCG GCTACGGTGA
 601 AGAACTGGAT ACTTGTTGTG TCTTCTGTGT ATTTTGTGG CAACAAGAGG CCAGAGACAA
 661 TCTATTCAAA CACCAAGCTT GCTCTTTTGA GCTACAAGAA CCTTCTAAAT ATATATCTAG
 721 TGGCCAGAAT GCCTAGGTCA CCTCTAAATG TGTAATTTGC CTGCTTGACC GACTGGGGCT
 781 GTTCGAAGCC CGAATGTAGG ATTGTTATCC GAACTCTGCT CGTAGAGGCA TGTTGTGAAT
 841 CTGTGTCGGG CAGGACACGC CTCGAAGGTT CACGGCAAGG GAAACCACCG ATAGCAGTGT
 901 CTAGTAGCAA CCTGTAAAGC CGCAATGCAG CATCACTGGA AAATACAAAC CAATGGCTAA
 961 AAGTACATAA GTTAATGCCT AAAGAAGTCA TATACCAGCG GCTAATAATT GTACAATCAA
1021 GTGGCTAAAC GTACCGTAAT TGCCAACGC GTTTCTAGAT TGCAGAAGCA CGGCAAAGCC
1081 CACTTACCCA CGTTTGTTTC TTCACTCAGT CCAATCTCAG CTGGTGATCC CCCAATTGGG
1141 TCGCTTGTTT GTTCCGGTGA AGTGAAAGAA GACAGAGGTA AGAATGTCTG ACTCGGAGCG
1201 TTTTGCATAC AACCAAGGGC AGTGATGGAA GACAGTGAAA TGTTGACATT CAAGGAGTAT
1261 TTAGCCAGGG ATGCTTGAGT GTATCGTGTA AGGAGGTTTG TCTGCCGATA CGACGAATAC
```

FIG. 18D

1321 TGTATAGTCA CTTCTGATGA AGTGGTCCAT ATTGAAATGT AAGTCGGCAC TGAACAGGCA

1381 AAAGATTGAG TTGAAACTGC CTAAGATCTC GGGCCCTCGG GCTTCGGCTT TGGGTGTACA

1441 TGTTTGTGCT CCGGGCAAAT GCAAAGTGTG GTAGGATCGA CACACTGCTG CCTTTACCAA

1501 GCAGCTGAGG GTATGTGATA GGCAAATGTT CAGGGGCCAC TGCATGGTTT CGAATAGAAA

1561 GAGAAGCTTA GCCAAGAACA ATAGCCGATA AAGATAGCCT CATTAAACGA AATGAGCTAG

1621 TAGGCAAAGT CAGCGAATGT GTATATATAA AGGTTCGAGG TCCGTGCCTC CCTCATGCTC

1681 TCCCCATCTA CTCATCAACT CAGATCCTCC AGGAGACTTG TACACCATCT TTTGAGGCAC

1741 AGAAACCCAA TAGTCAACCG CGGACTGCGC ATC[ATG]

FIG.18E

```
       10        20        30        40        50        60
        |         |         |         |         |         |
   1 CAATTCTCAC GGTGAATGTA GGCCTTTTGT AGGGTAGGAA TTGTCACTCA AGCACCCCCA
  61 ACCTCCATTA CGCCTCCCCC ATAGAGTTCC CAATCAGTGA GTCATGGCAC TGTTCTCAAA
 121 TAGATTGGGG AGAAGTTGAC TTCCGCCCAG AGCTGAAGGT CGCACAACCG CATGATATAG
 181 GGTCGGCAAC GGCAAAAAAG CACGTGGCTC ACCGAAAAGC AAGATGTTTG CGATCTAACA
 241 TCCAGGAACC TGGATACATC CATCATCACG CACGACCACT TTGATCTGCT GGTAAACTCG
 301 TATTCGCCCT AAACCGAAGT GCGTGGTAAA TCTACACGTG GGCCCCTTTC GGTATACTGC
 361 GTGTGTCTTC TCTAGGTGCA TTCTTTCCTT CCTCTAGTGT TGAATTGTTT GTGTTGGGAG
 421 TCCGAGCTGT AACTACCTCT GAATCTCTGG AGAATGGTGG ACTAACGACT ACCGTGCACC
 481 TGCATCATGT ATATAATAGT GATCCTGAGA AGGGGGGTTT GGAGCAATGT GGGACTTTGA
 541 TGGTCATCAA ACAAAGAACG AAGACGCCTC TTTTGCAAAG TTTTGTTTCG GCTACGGTGA
 601 AGAACTGGAT ACTTGTTGTG TCTTCTGTGT ATTTTGTGG CAACAAGAGG CCAGAGACAA
 661 TCTATTCAAA CACCAAGCTT GCTCTTTTGA GCTACAAGAA CCTTCTAAAT ATATATCTAG
 721 TGGCCAGAAT GCCTAGGTCA CCTCTAAATG TGTAATTTGC CTGCTTGACC GATCTAAACT
 781 GTTCGAAGCC CGAATGTAGG ATTGTTATCC GAACTCTGCT CGTAGAGGCA TGTTGTGAAT
 841 CTGTGTCGGG CAGGACACGC CTCGAAGGTT CACGGCAAGG GAAACCACCG ATAGCAGTGT
 901 CTAGTAGCAA CCTGTAAAGC CGCAATGCAG CATCACTGGA AAATACAAAC CAATGGCTAA
 961 AAGTACATAA GTTAATGCCT AAAGAAGTCA TATACCAGCG GCTAATAATT GTACAATCAA
1021 GTGGCTAAAC GTACCGTAAT TTGCCAACGC GTTTCTAGAT TGCAGAAGCA CGGCAAAGCC
1081 CACTTACCCA CGTTTGTTTC TTCACTCAGT CCAATCTCAG CTGGTGATCC CCCAATTGGG
1141 TCGCTTGTTT GTTCCGGTGA AGTGAAAGAA GACAGAGGTA AGAATGTCTG ACTCGGAGCG
1201 TTTTGCATAC AACCAAGGGC AGTGATGGAA GACAGTGAAA TGTTGACATT CAAGGAGTAT
1261 TTAGCCAGGG ATGCTTGAGT GTATCGTGTA AGGAGGTTTG TCTGCCGATA CGACGAATAC
```

FIG. 18F

1321 TGTATAGTCA CTTCTGATGA AGTGGTCCAT ATTGAAATGT AAGTCGGCAC TGAACAGGCA
1381 AAAGATTGAG TTGAAACTGC CTAAGATCTC GGGCCCTCGG GCTTCGGCTT TGGGTGTACA
1441 TGTTTGTGCT CCGGGCAAAT GCAAAGTGTG GTAGGATCGA CACACTGCTG CCTTTACCAA
1501 GCAGCTGAGG GTATGTGATA GGCAAATGTT CAGGGGCCAC TGCATGGTTT CGAATAGAAA
1561 GAGAAGCTTA GCCAAGAACA ATAGCCGATA AAGATAGCCT CATTAAACGA AATGAGCTAG
1621 TAGGCAAAGT CAGCGAATGT GTATATATAA AGGTTCGAGG TCCGTGCCTC CCTCATGCTC
1681 TCCCCATCTA CTCATCAACT CAGATCCTCC AGGAGACTTG TACACCATCT TTTGAGGCAC
1741 AGAAACCCAA TAGTCAACCG CGGACTGCGC ATC ATG

FIG.18G

METHOD FOR CLONING ACTIVE PROMOTERS

CROSS-REFERENCE TO RELATED APPLICATIONS

This application is a continuation of U.S. application Ser. No. 07/932,485, filed Aug. 19, 1992, now abandoned, which is a continuation-in-part of U.S. application Ser. No. 07/496,155 filed Mar. 19, 1990, now pending, which is a continuation of U.S application Ser. No. 07/044,097, now abandoned.

BACKGROUND OF THE INVENTION

I. Methods for the Identification of Promoters

Many systems have been used to isolate genes and their promoters located immediately upstream of the translation start site of a gene. The techniques can roughly be divided in two categories, namely (1) where the aim is to isolate genomic DNA fragments containing promoter activity randomly by so-called promoter probe vector systems and (2) where the aim is to isolate a gene per se from a genomic bank (library) and isolation of the corresponding promoter follows therefrom.

In promoter probe vector systems, genomic DNA fragments are randomly cloned in front of the coding sequence of a reporter gene that is expressed only when the cloned fragment contains promoter activity (Neve, R. L. et al., *Nature* 277:324–325 (1979)). Promoter probe vectors have been designed for cloning of promoters in *E. coli* (An, G. et al., *J. Bact.* 140:400–407 (1979)) and other bacterial hosts (Band, L. et al., *Gene* 26:313–315 (1983); Achen, M. G., *Gene* 45:45–49 (1986)), yeast (Goodey, A. R. et al., *Mol. Gen. Genet.* 204:505–511 (1986)) and mammalian cells (Pater, M. M. et al., *J. Mol. App. Gen.* 2:363–371 (1984)). Because it is well known in the art that Trichoderma promoters fail to work in *E. coli* and yeast (e.g. Penttilä, M. E. et al., *Mol. Gen. Genet.* 194:494–499 (1984)), these organisms cannot be used as hosts to isolate Trichoderma promoters. Due to the fact that, during the transformation of Trichoderma, the transforming DNA integrates into the fungal genome in varying copies in random locations, application of this method by using Trichoderma itself as a cloning host is also unlikely to succeed and would not be practical for efficient isolation of Trichoderma promoters with the desired properties.

Known genes can be isolated from either a cDNA or chromosomal gene bank (library) using hybridization as a detection method. Such hybridization may be with a corresponding, homologous gene from another organism (e.g. Vanhanen et al., *Curr. Genet.* 15:181–186 (1989)) or with a probe designed on the basis of expected similarities in amino acid sequence. If amino acid sequence is available for the corresponding protein, an oligonucleotide can also be designed which can be used in hybridization for isolation of the gene. If the gene is cloned into an expression bank, the expression product of gene can be also detected from such expression bank by using specific antibodies or an activity test.

Specific genes can be isolated by using complementation of mutations in *E. coli* or yeast (e.g. Keesey, J. K. et al., *J. Bact.* 152:954–958 (1982); Kaslow, D. C., *J. Biol. Chem.* 265:12337–12341 (1990); Kronstad, J. W., *Gene* 79:97–106 (1989)), or complementation of corresponding mutants of filamentous fungi for instance by using SIB selection (Akins et al., *Mol. Cell. Biol.* 5:2272–2278 (1985)).

However, a major concern is how to isolate specific genes that have the desired promoter properties, for example genes which would be most highly expressed when glucose is present in the medium. There is no information available in the literature to indicate which genes are the most highly expressed in an organism, and especially not from filamentous fungi. The phosphoglyceratekinase (PGK) promoter from the yeast *Saccharomyces cerevisiae* is considered to be a strong promoter for protein production. However, results obtained by the inventors have shown that the corresponding Trichoderma promoter is not suitable for such protein production. Thus, the identification of specific Trichoderma genes for their isolation in order to obtain the best possible promoter for protein production in certain desired conditions is unknown and cannot be predicted. Consequently one cannot rely on any previous nucleotide or amino acid sequence information, nor complement any previously known mutations, in gene isolation for such purpose in Trichoderma.

Differential hybridization has been used for cloning of genes expressed under certain conditions. The method relies on the screening of a bank separately with an induced and noninduced cDNA probe. By this method e.g. *Trichoderma reesei* genes strongly expressed during production of cellulolytic enzymes have been isolated (Teeri, T. et al., *Bio/Technology* 1:696–699 (1983)). The differential hybridization methods used are based on the idea that the genes searched for are expressed in certain conditions (like cellulases on cellulose) but not in some other conditions (like cellulases on glucose) which enables picking up clones hybridizing with only one of the cDNA probes used. However, for isolation of the genes expressed strongly on glucose, this approach (expression on glucose and not on some other media) is not a suitable one, and might in fact result in not finding the most highly expressed genes. This is because when differentially screening a chromosomal bank, only induced genes are selected. Such induced genes are not necessarily the most strongly expressed genes. Thus, no method is known in the art which would permit the identification of promoters which function strongly in Trichoderma on glucose medium.

Another option for obtaining a promoter with desired properties is to modify the already existing ones. This is based on the fact that the function of a promoter is dependent on the interplay of regulatory proteins which bind to specific, discrete nucleotide sequences in the promoter, termed motifs. Such interplay subsequently affects the general transcription machinery and regulates transcription efficiency. These proteins are positive regulators or negative regulators (repressors), and one protein can have a dual role depending on the context (Johnson, P. F. and McKnight, S. L. *Annu. Rev. Biochem.* 58:799–839 (1989)). However, even a basic understanding of the regions responsible for regulation of a promoter requires a considerable amount of experimental data, and data obtained from the corresponding promoter of another organism is usually not useful (see Vanhanen, S. et al., *Gene* 106:129–133 (1991)), or at least not sufficient, to explain the function of a promoter originating from another organism.

II. Translation Elongation Factors

Translation Elongation Factors (TEFs) are universally conserved proteins that promote the GTP-dependent binding of an aminoacyl-tRNA to ribosomal A-site in protein synthesis. Especially conserved is the N-terminus of the protein containing the GTP binding domain. TEFs are known as very abundant proteins in cells comprising about 4–6% of total soluble proteins (Miyajima, I. et al., *J. Biochem.* 83:453–462 (1978); Thiele, D. et al., *J. Biol. Chem.* 260:3084–3089 (1985)).

tef genes have been isolated from several organisms. In some of them they constitute a multigene family. Also a number of pseudogenes have been isolated from some organisms. The promoter of the human tef gene can direct transcription in vitro at least 2-fold more effectively than the adenovirus major late promoter, which indicates that the tef promoter is a strong promoter in mammalian expression systems (Uetsuki et al., *J. Biol. Chem.* 264:5791–5798 (1989)). Both the human and the *A. thaliana* tef1 promoter (for translation elongation factor EF-1α) has been used in an expression system with high efficiency of gene expression (Kim et al., *Gene* 91:217–223 (1990); Curie et al., *Nucl. Acid Res.* 19:1305–1310 (1991)). In both cases the full expression of the promoter was dependent on the presence of the intron in the 5' noncoding region.

tef is quite constitutively expressed, the major exception being its expression in aging and quiescent cells. It is not known to be regulated by the growth substrates of the host.

III. Expression of Recombinant Proteins in Trichoderma

The filamentous fungus *Trichoderma reesei* is an efficient producer of hydrolases, especially of different cellulose degrading enzymes. Due to its excellent capacity for protein secretion and developed methods for industrial cultivations, Trichoderma is a powerful host for production of heterologous, recombinant proteins in large scale. The efficient production of both homologous and heterologous proteins in fungi relies on fungal promoters. The promoter of the main cellulase gene of Trichoderma, cellobiohydrolase 1 (cbh1), has been used for production of heterologous proteins in Trichoderma grown on media containing cellulose or its derivatives (Harkki et al., *Bio/Technology* 7:596–603 (1989); Saloheimo et al., *Bio/Technology* 9:987–990 (1991)). The cbh1 promoter cannot be used when the Trichoderma are grown on glucose containing media due to glucose repression of cbh1 promoter activity. This regulation occurs at the transcriptional level and thus glucose repression could be mediated through the promoter sequences. However, nothing is yet known of the mechanism of glucose repression at the promoter level in filamentous fungi.

Glucose repression in the yeast *Saccharomyces cerevisiae* has been studied for many years. These studies have however failed, until recently, to identify binding sequences in promoters or regulatory proteins binding to promoters which would mediate glucose repression. The first ever published glucose repressor protein and the binding sequence in eukaryotic cells was published by Nehlin and Ronne (Nehlin, J. O. and Ronne, H. *EMBO J.* 9:2891–2899 (1990)). This MIG1 protein seems to be responsible of one fifth of the glucose repression of GAL genes in *Saccharomyces cerevisiae*, other factors still being required to obtain full glucose repression effect (Nehlin, J. O. et al., *EMBO J.* 10:3373–3377 (1991)).

Thus, it is desirable to be able to produce proteins in Trichoderma grown on glucose. Not only is the substrate glucose cheap and readily available, but also Trichoderma produces less protease activity when grown on glucose. Further, cellulase production is repressed when Trichoderma is grown on glucose, thus allowing for the easier purification of the desired product from the Trichoderma medium. Nevertheless, to date there has been no identification or characterization of any promoter that is highly functional in Trichoderma grown on glucose. In addition, no modifications of the normally glucose repressed promoter, the cbh1 promoter, have been identified which would allow the use of this strong promoter for expression of heterologous genes in Trichoderma grown on glucose.

SUMMARY OF THE INVENTION

This invention is first directed to the identification of the motif, the DNA element, that imparts glucose repression onto the Trichoderma cbh1 promoter.

The invention is further directed to a modified Trichoderma cbh1 promoter, such modified promoter lacking such glucose repression element and such modified promoter being useful for the production of proteins, including cellulases, when the host is grown on glucose medium.

The invention is further directed to a method for the isolation of genes that are highly expressed on glucose, especially from filamentous fungal hosts such as Trichoderma.

The invention is further directed to five such previously undescribed genes and their promoters from *Trichoderma reesei*.

The invention is further directed to specific cloning vectors for Trichoderma containing the above mentioned sequences.

The invention is further directed to filamentous fungal strains transformed with said vectors, which strains thus are able to produce proteins such as cellulases on glucose.

The invention is further directed to a process for producing cellulases or other useful enzymes on glucose.

BRIEF DESCRIPTION OF THE DRAWINGS

FIG. 1. FIG. 1B is the nucleotide sequence of the tef1 promoter and coding sequence [SEQ ID 1]. The promoter sequence stops at base number 1234. The methionine codon of the start site of translation is located at base numbers 1235–1237 and is underlined.

FIG. 3. FIG. 3B is the nucleotide sequence of the cDNA1 promoter and coding sequence [SEQ ID 2]. The promoter sequence stops at base number 1857. The methionine codon of the start site of translation is located at base numbers 1858–1860 and is underlined, the first 700 bases shown in SEQ. ID 2 are bacterial sequences.

FIG. 4. FIG. 4B is the nucleotide sequence of the cDNA10 promoter and coding sequence [SEQ ID 3]. The promoter sequence stops at base number 1522. The methionine codon of the start site of translation is located at base numbers 1523–1525 and is underlined.

FIG. 5. FIG. 5B is the nucleotide sequence of the cDNA12 promoter and coding sequence [SEQ ID 4]. The promoter sequence stops at base number 1101. The methionine codon of the start site of translation is located at base numbers 1102–1104 and is underlined.

FIG. 6. FIG. 6B is the nucleotide sequence of the cDNA15 promoter and coding sequence [SEQ ID 5].

FIG. 7. FIG. 7B shows the sequence of the egl1 cDNA [SEQ ID 16]. FIG. 7C shows the sequence of the cbh1 terminator of pPLE3 [SEQ ID 23].

FIG. 13. FIG. 13B is the sequence of the cbh1 promoter of plasmid pMLO16 [SEQ ID18]. FIG. 13C is the sequence of the *T. reesei* cbh1 terminator on plasmid pMLO16 and plasmids derived from it [SEQ ID24].

FIG. 15. FIG. 15B is the sequence of the truncated cbh1 promoter [SEQ ID19]. The polylinker is underlined. The arrow denotes the deletion site.

FIG. 16. FIG. 16B shows the sequence of the KspI-XmaI fragment (the underlined portion) that contains the chromosomal cbh1 gene [SEQ ID17].

FIG. 18. FIG. 18B is the sequence of the altered cbh1 promoter of pMI-24 ([SEQ ID20]). The polylinker is underlined and the sequence alteration is boxed. FIG. 18C is the sequence of the altered cbh1 promoter of pMI-27 ([SEQ ID21]). The polylinker is underlined, the arrow denotes the deletion point and the sequence alterations are boxed. FIG. 18D is the sequence of the altered cbh1 promoter of pMI-28 ([SEQ ID22]). The polylinker is underlined, the arrow denotes the deletion point and the sequence alterations are boxed.

DETAILED DESCRIPTION OF THE PREFERRED EMBODIMENTS

Figure 1A:
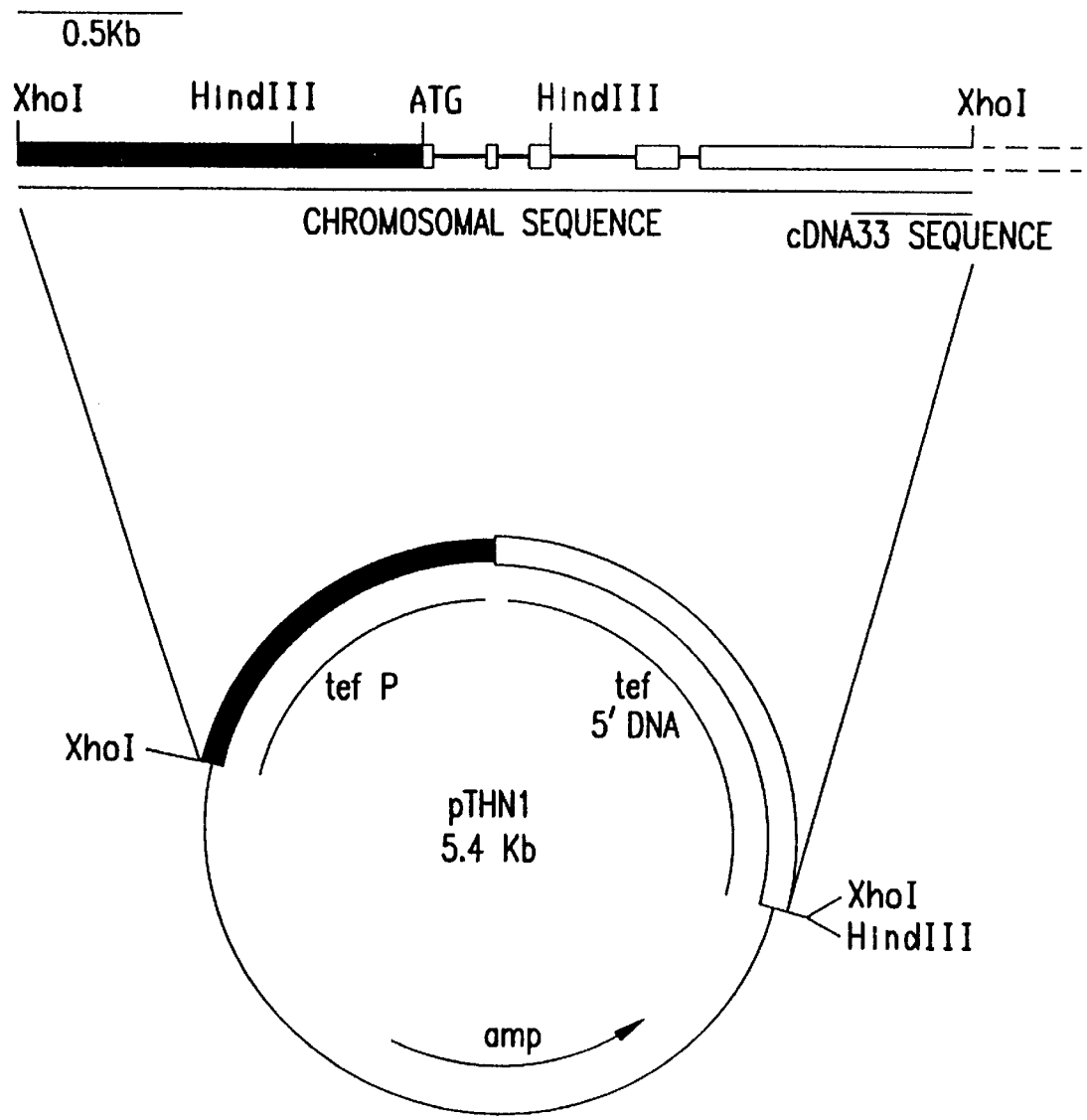
FIG. 1A shows the plasmid pTHN1 which carries the tef1 promoter and 5' part of the coding region and shows the relevant features of the tef1 gene and the sequenced areas.

1. Identification of Fungal Genes that Express on Glucose Medium

In the following description, reference will be made to various methodologies known to those of skill in the art of molecular genetics and biology. Publications and other materials setting forth such known methodologies to which reference is made are incorporated herein by reference in their entireties as though set forth in full.

General principles of the biochemistry and molecular biology of the filamentous fungi are set forth, for example, in Finkelstein, D. B. et al., eds., *Biotechnology of Filamentous Fungi: Technology and Products*, Butterworth-Heinemann, publishers, Stoneham, Mass. (1992) and Bennett, J. W. et al., *More Gene Manipulations in Fungi*, Academic Press-Harcourt Brace Jovanovich, publishers, San Diego Calif. (1991).

To be able to develop versatile systems for protein production from Trichoderma, especially when Trichoderma are grown on glucose, a method has been developed for the isolation of previously unknown Trichoderma genes which are highly expressed on glucose, and their promoters. The method of the invention requires the use of only one cDNA population of probes.

It is to be understood that the method of the invention would be useful for the identification of promoter sequences that are active under any desired environmental condition to which a cell could be exposed, and not just to the exemplified isolation of promoters that are capable of expression in glucose medium. By "environmental condition" is meant the presence of a physical or chemical agent, such agent being present in the cellular environment, either extracellularly or intracellularly. Physical agent would include, for example, certain growth temperatures, especially a high or low temperature. Chemical agents would include any compound or mixtures including carbon growth substrates, drugs, atmospheric gases, etc.

According to the method of the invention, the organism is first grown under the desired growth condition, such as the use of glucose as a carbon source. Total mRNA is then extracted from the organism and preferably purified through at least a polyA+ enrichment of the mRNA from the total RNA population. A cDNA bank is made from this total mRNA population using reverse transcriptase and the cDNA population cloned into any appropriate vector, such as the commercially available lambda-ZAP vector system (Stratagene). When using the lambda-ZAP vector system, or any lambda vector system, the cDNA is packaged such that it is suitable for infection of any *E. coli* strain susceptible to lambda bacteriophage infection.

The CDNA bank is transferred by standard colony hybridization techniques onto nitrocellulose filters for screening. The bank is plated and plaque lifts are taken onto nitrocellulose. The bank is screened with a population of labelled cDNAs that had been synthesized against the same RNA population from which the cloned cDNA bank was constructed, using stringent hybridization conditions. It should be noted that the genes are not expressed in any way during this selection process. This results in clones hybridizing with varying intensity and the ones showing the strongest signals are picked. Genes that are most strongly expressed in the orginal population comprise the majority of the total mRNA pool and thus give a strong signal in this selection.

The inserts in clones with the strongest signals are sequenced from the 3' end of the insert using any standard DNA sequencing technique as known in the art. This provides a first identification of each clone and allows the exclusion of identical clones. The frequency with which each desired clone is represented in the cDNA lambda-bank is determined by hybridizing the bank against a clone-specific PCR probe. The desired clones are those which, in addition to having the strongest signals as above, are also represented at the highest frequencies in the cDNA bank, since this implies that the abundancy of the mRNA in the population was relatively high and thus that the promoter for that gene was highly active under the growth conditions. Thus, the relevance of this approach and any clone identified therefrom can be double-checked: the intensity of the hybridization signal of a specific clone should correlate positively with the frequency with which that clone is found in the cDNA bank. The inserts of the clones selected in this manner, such inserts corresponding to the cDNA sequences, may be used as probes to isolate the corresponding genes and their promoters from a chromosomal bank, such as one cloned into lambda as above.

The method of the invention is not limited to Trichoderma, but would be useful for cloning genes from any host, or from a specific tissue with such host, from which a cDNA bank may be constructed, including, prokaryote (bacterial) hosts, and any eukaryotic host plants, mammals, insects, yeast, and any cultured cell populations.

For example, using the method of the invention, five genes that express relatively high levels of mRNA in *Trichoderma reesei* when such Trichoderma are grown on glucose were identified. These genes were sequenced and identified as clone cDNA33, cDNA1, cDNA10, cDNA12, and cDNA15. When used to screen a Trichoderma chromosomal lambda-bank, the corresponding genes and their promoters were identified. Such genes and promoters (or portions thereof) may then be subcloned into any desired vector, such as the pSP73 vector (Promega, Madison, Wis., USA).

According to the invention, the clones containing the genes and their promoters (or parts of them) highly expressed in Trichoderma grown on glucose are represented as follows:

| Plasmid | Figure | cDNA | Figure | SEQ ID No |
| --- | --- | --- | --- | --- |
| pTHN1 | 1A | cDNA33 | 1B | 1 |
| pEA33 | 2 | cDNA33 | 1B | 1 |
| pTHN3 | 3A | cDNA1 | 3B | 2 |
| pEA10 | 4A | cDNA10 | 4B | 3 |
| pEA12 | 5A | cDNA12 | 5B | 4 |
| pEA155 | 6A | cDNA15 | 6B | 5 |

One of the genes isolated according to the invention as being highly expressed when Trichoderma was grown on glucose has been identified as the one encoding Trichoderma translation elongation factor 1α (tef1). In addition, four other, new genes have been identified for the first time that are highly expressed on glucose in Trichoderma.

These data show that the method used in this invention resulted in isolating five genes, one of which (tef1) is known to be efficiently expressed in other organisms. However, the tef1 gene was not the most highly expressed of the five genes isolated from the Trichoderma cDNA bank by the method of the invention.

Of the five genes isolated, only tef1 shows a relevant degree of homology to any known protein sequences. All of the genes isolated are also expressed on other carbon sources and would not have been found with the classical method of differential cloning. This shows the importance of the method used in this invention in isolation of the most suitable genes for a specific purpose, such as for isolation of strong promoters for expression on glucose containing medium.

The promoter of any of these genes may be operably linked to a sequence heterologous to such promoter, and especially heterologous to the host Trichoderma, for expression of such gene from a Trichoderma host that is grown on glucose. Preferably, the coding sequence provides a secretion signal for secretion of the recombinant protein into the medium.

Use of the promoters of the invention allow for the expression of genes from Trichoderma under conditions in which there are no cellulases and relatively few proteases. Thus, for the first time, recombinant genes can be highly expressed on Trichoderma using a glucose-based growth medium.

The promoters of the invention, while being strongly expressed on glucose (that is, when the filamentous fungal host is grown on medium providing glucose as a carbon and energy source), are not repressed in the absence of glucose. In addition, they are active when the Trichoderma host is grown on carbon sources other than glucose.

The glucose promoters of the invention, and those identified by the methods of the invention, can be used to produce enzymes native to Trichoderma itself, especially of those capable of hydrolysing different kinds of plant material. On glucose, the fungus does not naturally produce these enzymes and consequently one or more specific hydrolytic enzymes could be produced on glucose medium free from other plant material hydrolyzing enzymes. This would result in an enzyme preparate or enzyme mixtures for specific applications.

II. Modification of the Cellobiohydrolase I Promoter

This invention also describes a method for the modification of the cellobiohydrolase 1 promoter (cbh1) such that the activity of the promoter is retained but the promoter no longer is repressed when cells are grown on glucose-containing medium. Essentially, the DNA motif that imparted glucose repression has been identified and removed from this promoter, allowing production of desired proteins whose coding sequences are operably linked to the promoter in suitable hosts, such as Trichoderma. Such a modified cbh1 promoter is termed a derepressed cbh1 promoter. As above, when the recombinant organisms obtained from transformation with such constructs are cultivated on glucose containing medium, any protein, including a cellulase may be produced without production of other plant material hydrolysing enzymes, especially of native cellulases.

Isolated glucose promoters or derepressed cbh1 promoter can be used for instance to produce separate individual cellulases in hosts grown on glucose without any simultaneous production of other hydrolases such as other cellulases, hemicellulases, xylanases etc. or to produce heterologous proteins in varying growth media.

III. Preparation of Coding Sequences Operably Linked to the Promoter Sequences of the Invention The process for genetically engineering a coding sequence, for expression under a promoter of the invention, is facilitated through the isolation and partial sequencing of pure protein encoding an enzyme of interest or by the cloning of genetic sequences which are capable of encoding such protein with polymerase chain reaction technologies; and through the expression of such genetic sequences. As used herein, the term "genetic sequences" is intended to refer to a nucleic acid molecule (preferably DNA). Genetic sequences that are capable of encoding a protein are derived from a variety of sources. These sources include genomic DNA, cDNA, synthetic DNA, and combinations thereof. The preferred source of genomic DNA is a fungal genomic bank. The preferred source of the cDNA is a cDNA bank prepared from fungal mRNA grown in conditions known to induce expression of the desired gene to produce mRNA or protein. However, since the genetic code is universal, a coding sequence from any host, including prokaryotic (bacterial) hosts, and any eukaryotic host plants, mammals, insects, yeasts, and any cultured cell populations would be expected to function (encode the desired protein).

Genomic DNA may or may not include naturally occurring introns. Moreover, such genomic DNA may be obtained in association with the 5' promoter region of the gene sequences and/or with the 3' transcriptional termination region. According to the invention however, the native promoter region would be replaced with a promoter of the invention.

Such genomic DNA may also be obtained in association with the genetic sequences which encode the 5' non-translated region of the mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA may be retained and employed for transcriptional and translational regulation.

Genomic DNA can be extracted and purified from any host cell, especially a fungal host cell, which naturally expresses the desired protein by means well known in the art. A genomic DNA sequence may be shortened by means known in the art to isolate a desired gene from a chromosomal region that otherwise would contain more information than necessary for the utilization of this gene in the hosts of the invention. For example, restriction digestion may be utilized to cleave the full-length sequence at a desired location. Alternatively, or in addition, nucleases that cleave from the 3'-end of a DNA molecule may be used to digest a certain sequence to a shortened form, the desired length then being identified and purified by gel electrophoresis and DNA sequencing. Such nucleases include, for example, Exonuclease III and Bal31. Other nucleases are well known in the art.

For cloning into a vector, such suitable DNA preparations (either genomic DNA or cDNA) are randomly sheared or enzymatically cleaved, respectively, and ligated into appropriate vectors to form a recombinant gene (either genomic or cDNA) bank.

A DNA sequence encoding a desired protein or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., (Maniatis, T. et al., *Molecular Cloning (A Laboratory Manual)*, Cold Spring Harbor Laboratory, second edition, 1988) and are well known in the art.

Libraries containing sequences coding for the desired gene may be screened and the desired gene sequence identified by any means which specifically selects for a sequence coding for such gene or protein such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immuno-precipitation of a translated protein product produced by the host containing the clone.

Oligonucleotide probes specific for a certain protein which can be used to identify clones to this protein can be designed from the knowledge of the amino acid sequence of the protein or from the knowledge of the nucleic acid sequence of the DNA encoding such protein or a related protein. Alternatively, antibodies may be raised against purified forms of the protein and used to identify the presence of unique protein determinants in transformants that express the desired cloned protein. When an amino acid sequence is listed horizontally, unless otherwise stated, the amino terminus is intended to be on the left end and the carboxy terminus is intended to be at the right end. Similarly, unless otherwise stated or apparent from the context, a nucleic acid sequence is presented with the 5' end on the left.

Because the genetic code is degenerate, more than one codon may be used to encode a particular amino acid. Peptide fragments may be analyzed to identify sequences of amino acids that may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code, one or more different oligonucleotides can be identified from the amino acid sequence, each of which would be capable of encoding the desired protein. The probability that a particular oligonucleotide will, in fact, constitute the actual protein encoding sequence can be estimated by considering abnormal base pairing relationships and the frequency with which a particular codon is actually used (to encode a particular amino acid) in eukaryotic cells. Using "codon usage rules," a single oligonucleotide sequence, or a set of oligonucleotide sequences, that contain a theoretical "most probable" nucleotide sequence capable of encoding the protein sequences is identified.

The suitable oligonucleotide, or set of oligonucleotides, which is capable of encoding a fragment of a certain gene (or which is complementary to such an oligonucleotide, or set of oligonucleotides) may be synthesized by means well known in the art (see, for example, *Oligonucleotides and Analogues, A Practical Approach*, F. Eckstein, ed., 1992, IRL Press, New York) and employed as a probe to identify and isolate a clone to such gene by techniques known in the art. Techniques of nucleic acid hybridization and clone identification are disclosed by Maniatis, T., et al., in: *Molecular Cloning, A Laboratory Manual*, Cold Spring Harbor Laboratories, Cold Spring Harbor, N.Y. (1982)), and by Hames, B. D., et al., in: *Nucleic Acid Hybridization, A Practical Approach*, IRL Press, Washington, DC (1985)). Those members of the above-described gene bank which are found to be capable of such hybridization are then analyzed to determine the extent and nature of coding sequences which they contain.

To facilitate the detection of a desired DNA coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. If single stranded, the oligonucleotide may be radioactively labelled using kinase reactions. Alternatively, polynucleotides are also useful as nucleic acid hybridization probes when labeled with a non-radioactive marker such as biotin, an enzyme or a fluorescent group.

Thus, in summary, the elucidation of a partial protein sequence, permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a gene.

In an alternative way of cloning a gene, a bank is prepared using an expression vector, by cloning DNA or, more preferably cDNA prepared from a cell capable of expressing the protein into an expression vector. The bank is then screened for members which express the desired protein, for example, by screening the bank with antibodies to the protein.

The above discussed methods are, therefore, capable of identifying genetic sequences that are capable of encoding a protein or biologically active or antigenic fragments of this protein. The desired coding sequence may be further characterized by demonstrating its ability to encode a protein having the ability to bind antibody in a specific manner, the ability to elicit the production of antibody which are capable of binding to the native, non-recombinant protein, the ability to provide a enzymatic activity to a cell that is a property of the protein, and the ability to provide a non-enzymatic (but specific) function to a recipient cell, among others.

In order to produce the recombinant protein in the vectors of the invention, it is desirable to operably link such coding sequences to the glucose regulatable promoters of the invention. When the coding sequence and the operably linked promoter of the invention are introduced into a recipient eukaryotic cell (preferably a fungal host cell) as a non-replicating DNA (or RNA), non-integrating molecule, the expression of the encoded protein may occur through the transient (nonstable) expression of the introduced sequence.

Preferably the coding sequence is introduced on a DNA molecule, such as a closed circular or linear molecule that is incapable of autonomous replication. Preferably, a linear molecule that integrates into the host chromosome. Genetically stable transformants may be constructed with vector systems, or transformation systems, whereby a desired DNA is integrated into the host chromosome. Such integration may occur de novo within the cell or, be assisted by transformation with a vector which functionally inserts itself into the host chromosome.

The gene encoding the desired protein operably linked to the promoter of the invention may be placed with a transformation marker gene in one plasmid construction and introduced into the host cells by transformation, or, the marker gene may be on a separate construct for co-transformation with the coding sequence construct into the host cell. The nature of the vector will depend on the host organism. In the practical realization of the invention the filamentous fungus Trichoderma has been employed as a model. Thus, for Trichoderma and especially for *T. reesei*, vectors incorporating DNA that provides for integration of the expression cassette (the coding sequence operably linked to its transcriptional and translational regulatory elements) into the host's chromosome are preferred. It is not necessary to target the chromosomal insertion to a specific site. However, targeting the integration to a specific locus may be achieved by providing specific coding or flanking sequences on the recombinant construct, in an amount sufficient to direct integration to this locus at a relevant frequency.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transformation. A genetic marker especially for the transformation of the hosts of the invention is amdS, encoding acetamidase and thus enabling Trichoderma to grow on acetamide as the only nitrogen source. Selectable markers for use in transforming filamentous fungi include, for example, acetamidase (the amdS gene), benomyl resistance, oligomycin resistance, hygromycin resistance, aminoglycoside resistance, bleomycin resistance; and, with auxotrophic mutants, ornithine carbamoyltransferase (OCTase or the argB gene). The use of such markers is also reviewed in Finkelstein, D. B. in: *Biotechnology of Filamentous Fungi: Technology and Products*, Chapter 6, Finkelstein, D. B. et al., eds., Butterworth-Heinemann, publishers, Stoneham, Mass., (1992), pp. 113–156).

To express a desired protein and/or its active derivatives, transcriptional and translational signals recognizable by an appropriate host are necessary. The cloned coding sequences, obtained through the methods described above, and preferably in a double-stranded form, may be operably linked to sequences controlling transcriptional expression in an expression vector, and introduced into a host cell, either prokaryote or eukaryote, to produce recombinant protein or a functional derivative thereof. Depending upon which strand of the coding sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of the protein or a functional derivative thereof, in eukaryotic cells, and especially in fungus.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a coding sequence and a promoter region sequence linked to the 5' end of the coding sequence) are said to be operably linked if induction of promoter function results in the transcription of mRNA encoding the desired protein and if the nature of the linkage between the two DNA sequences does not (1) result in the introduction of a frame-shift mutation, (2) interfere with the ability of the expression regulatory sequences to direct the expression of the protein, antisense RNA, or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences may also include enhancer sequences or upstream activator sequences, as desired.

Expression of a protein in eukaryotic hosts such as fungus requires the use of regulatory regions functional in such hosts, and preferably fungal regulatory systems. A wide variety of transcriptional and translational regulatory sequences can be employed, depending upon the nature of the host. Preferably, these regulatory signals are associated in their native state with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from filamentous fungal genes which encode a mRNA product capable of translation are preferred, and especially, strong promoters can be employed provided they also function as promoters in the host cell.

As is widely known, translation of eukaryotic mRNA is initiated at the codon which encodes the first methionine. For this reason, it is preferable to ensure that the linkage between a eukaryotic promoter and a DNA sequence which encodes the desired protein, or a functional derivative thereof, does not contain any intervening codons which are capable of encoding a methionine. The presence of such codons results either in a formation of a fusion protein (if the AUG codon is in the same reading frame as the protein-coding DNA sequence) or a frame-shift mutation (if the AUG codon is not in the same reading frame as the protein-coding sequence).

It may be desired to construct a fusion product that contains a partial coding sequence (usually at the amino terminal end) of a protein and a second coding sequence (partial or complete) of a second protein. The first coding sequence may or may not function as a signal sequence for secretion of the protein from the host cell. For example, the sequence coding for desired protein may be linked to a signal sequence which will allow secretion of the protein from, or the compartmentalization of the protein in, a particular host. Such fusion protein sequences may be designed with or without specific protease sites such that a desired peptide sequence is amenable to subsequent removal. In a preferred embodiment, the native signal sequence of a fungal protein is used, or a functional derivative of that sequence that retains the ability to direct the secretion of the peptide that is operably linked to it. Aspergillus leader/secretion signal elements also function in Trichoderma.

If desired, the non-transcribed and/or non-translated regions 3' to the sequence coding for a desired protein can be obtained by the above-described cloning methods. The 3'-non-transcribed region may be retained for its transcriptional termination regulatory sequence elements, or for those elements which direct polyadenylation in eukaryotic cells. Where the native expression control sequences signals do not function satisfactorily in a host cell, then sequences functional in the host cell may be substituted.

The vectors of the invention may further comprise other operably linked regulatory elements such as DNA elements which confer antibiotic resistance, or origins of replication for maintenance of the vector in one or more host cells.

In another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors may be employed for this purpose. In Bacillus hosts, integration of the desired DNA may be necessary.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

When it is desired to use *S. cerevisiae* as a host for a shuttle vector, preferred *S. cerevisiae* yeast plasmids include those containing the 2-micron circle, etc., or their derivatives. Such plasmids are well known in the art (Botstein, D., et al., *Miami Wntr. Symp.* 19:265–274 (1982); Broach, J. R., in: *The Molecular Biology of the Yeast Saccharomyces: Life Cycle and Inheritance,* Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise,* Vol. 3, Gene Expression, Academic Press, NY, pp. 563–608 (1980)), and are commercially available.

Once the vector or DNA sequence containing the construct(s) is prepared for expression, the DNA construct (s) is introduced into an appropriate host cell by any of a variety of suitable means, including transformation. After the introduction of the vector, recipient cells are grown in a selective medium, which selects for the growth of vector-containing cells. If this medium includes glucose, expression of the cloned gene sequence(s) results in the production of the desired protein, or in the production of a fragment of this protein as desired. This expression can take place in a continuous manner in the transformed cells, or in a controlled manner, for example, by induction of expression.

Fungal transformation is carried out also accordingly to techniques known in the art, for example, using, for example, homologous recombination to stably insert a gene into the fungal host and/or to destroy the ability of the host cell to express a certain protein.

Fungi useful as recombinant hosts for the purpose of the invention include, e.g. Trichoderma, Aspergillus, *Claviceps purpurea, Penicillium chrysogenum, Magnaporthe grisea,* Neurospora, Mycosphaerella spp., *Collectotrichum trifolii,* the dimorphic fungus *Histoplasmia capsulatum, Nectria haematococca* (anamorph: *Fisarium solani* f. sp. *phaseoli* and f. sp. *pisi*), *Ustilago violacea, Ustilago maydis, Cephalosponium acremonium, Schizophyllum commune, Podospora anserina, Sordaria macrospora, Mucor circinelloides,* and *Collectotrichum capsici.* Transformation and selection techniques for each of these fungi have been described (reviewed in Finkelstein, D. B. in: *Biotechnology of Filamentous Fungi: Technology and Products,* Chapter 6, Finkelstein, D. B. et al., eds., Butterworth-Heinemann, publishers, Stoneham, Mass., (1992), pp. 113–156). Especially preferred are *Trichoderma reesei, T. harzianum, T. longibrachiatum, T. viride, T. koningii, Aspergillus nidulans, A. niger, A. terreus, A. ficum, A. oryzae, A. awamori* and *Neurospora crassa.*

The hosts of the invention are meant to include all Trichoderma. Trichoderma are classified on the basis of morphological evidence of similarity. *T. reesei* was formerly known as *T. viride* Pers. or *T. koningii* Oudem; sometimes it was classified as a distinct species of the *T. longibrachiatum* group. The entire genus Trichoderma, in general, is characterized by rapidly growing colonies bearing tufted or pustulate, repeatedly branched conidiophores with lageniform phialides and hyaline or green conidia borne in slimy heads (Bissett, J., Can. J. Bot. 62:924–931 (1984)).

The fungus called *T. reesei* is clearly defined as a genetic family originating from the strain QM6a, that is, a family of strains possessing a common genetic background originating from a single nucleus of the particular isolate QM6a. Only those strains are called *T. reesei.*

Classification by morphological means is problematic and the first recently published molecular data from DNA-fingerprint analysis and the hybridization pattern of the cellobiohydrolase 2 (cbh2) gene in *T. reesei* and *T. longibrachiatum* clearly indicates a differentiation of these strains (Meyer, W. et al., *Curr. Genet.* 21:27–30 (1992); Morawetz, R. et al., *Curr. Genet.* 21:31–36 (1992).

However, there is evidence of similarity between different Trichoderma species at the molecular level that is found in the conservation of nucleic acid and amino acid sequences of macromolecular entities shared by the various Trichoderma species. For example, Cheng, C., et al., *Nucl. Acids. Res.* 18:5559 (1990), discloses the nucleotide sequence of *T. viride* cbh1. The gene was isolated using a probe based on the *T. reesei* sequence. The authors note that there is a 95% homology between the amino acid sequences of the *T. viride* and *T. reesei* gene. Goldman, G. H. et al., *Nucl. Acids Res.* 18:6717 (1990), discloses the nucleotide sequence of phosphoglycerate kinases from *T. viride* and notes that the deduced amino acid sequence is 81% homologous with the phosphoglycerate kinase gene from *T. reesei*. Thus, the species classified to *T. viride* and *T. reesei* must genetically be very close to each other.

In addition, there is a high similarity of transformation conditions among the Trichoderma. Although practically all the industrially important species of Trichoderma can be found in the formerly discussed Trichoderma section Longbrachiatum, there are some other species of Trichoderma that are not assigned to this section. Such a species is, for example, *Trichoderma harzianum,* which acts as a biocontrol agent against plant pathogens. A transformation system has also been developed for this Trichoderma species (Herrera-Estrella, A. et al., *Molec. Microbiol.* 4:839–843 (1990), that is essentially the same as that taught in the application. Thus, even though *Trichoderma harzianum* is not assigned to the section Longibrachiatum, the method used by Herrera-Estrella in the preparation of spheroplasts before transformation is the same. The teachings of Herrera-Estrella show that there is not a significant diversity of Trichoderma spp. such that the transformation system of the invention would not be expected to function in all Trichoderma.

Further, there is a common functionality of fungal transcriptional control signals among fungal species. At least three *A. nidulans* promoter sequences, amdS, argB, and gpd, have been shown to give rise to gene expression in *T. reesei.* For amdS and argB, only one or two copies of the gene are sufficient to being about a selectable phenotypes (Penttilä et al., *Gene* 61:155–164 (1987)). Gruber, F. et al., *Curr. Genetic* 18:71–76 (1990) also notes that fungal genes can often by successfully expressed across different species. Therefore, it is to be expected that the glucose regulated promoters identified herein would be also regulatable by glucose in other fungi.

Many species of fungi, and especially Trichoderma, are available from a wide variety of resource centers that contain fungal culture collections. In addition, Trichoderma species are catalogued in various databases. These resources and databases are summarized by O'Donnell, K. et al., in *Biochemistry of Filamentous Fungi: Technology and Products*, D. B. Fingelstein et al., eds., Butterworth-Heinemann, Stoneham, Mass., USA, 1992, pp. 3–39.

After the introduction of the vector and selection of the transformant, recipient cells are grown in a selective medium, which selects for the growth of vector-containing cells. Expression of the cloned gene sequence(s) results in the synthesis and secretion of the desired heterologous or homologous protein, or in the production of a fragment of this protein, into the medium of the host cell.

In a preferred embodiment, the coding sequence is the sequence of an enzyme that is capable of hydrolysing lignocellulose. Examples of such sequences include a DNA sequence encoding cellobiohydrolase I (CBHI), cellobiohydrolase II (CBHII), endoglucanase I (EGI), endoglucanase II (EGII), endoglucanase III (EGIII), β-glucosidases, xylanases (including endoxylanases and β-xylosidase), sidegroup cleaving activities, (for example, α-arabinosidase, α-D-glucuronidase, and acetyl esterase), mannanases, pectinases (for example, endo-polygalacturonase, exopolygalacturonase, pectinesterase, or, pectin and pectin acid lyase), and enzymes of lignin polymer degradation, (for example, lignin peroxidase LIII from *Phlebia radiata* (Saloheimo et al., *Gene* 85:343–351 (1989)), or the gene for another ligninase, laccase or Mn peroxidase (Kirk, In: *Biochemistry and Genetics of Cellulose Degradation*, Aubert et al. (eds.), FEMS Symposium No. 43, Academic Press, Harcourt, Brace Jovanovitch Publishers, London. pp. 315–332 (1988))). The cloning of the cellulolytic enzyme genes has been described and recently reviewed (Teeri, T. T. in: *Biotechnology of Filamentous Fungi: Technology and Products*, Chapter 14, Finkelstein, D. B. et al., eds., Butterworth-Heinemann, publishers, Stoneham, Mass., (1992), pp. 417–445). The gene for the native cellobiohydrolase CBHI sequence has been cloned by Shoemaker et al. (Shoemaker, S., et al., *Bio/Technology* 1:691–696 (1983)) and Teeri et al. (Teeri, T., et al., *Bio/Technology* 1:696–699 (1983)) and the entire nucleotide sequence of the gene is known (Shoemaker, S., et al., *Bio/Technology* 1:691–696 (1983)). From *T. reesei*, the gene for the major endoglucanase (EGI) has also been cloned and characterized (Penttila, M., et al., *Gene* 45:253–263 (1986); Patent Application EP 137,280; Van Arstel, J. N. V., et al., *Bio/Technology* 5:60–64). Other isolated cellulase genes include cbh2 (Patent Application WO 85/04672; Chen, C. M., et al., *Bio/Technology* 5:274–278 (1987)) and egl3 (Saloheimo, M., et al., *Gene* 63:11–21 (1988)). The genes for the two endo-β-xylanases of *T. reesei* (xln1 and xln2) have been cloned and described in applicants' copending application, U.S. Ser. No. 07/889,893, filed May 29, 1992. The xylanase proteins have been purified and characterized (Tenkanen, M. et al., *Proceeding of the Xylans and Xylanases Symposium*, Wageningen, Holland (1991)).

The expressed protein may be isolated and purified from the medium of the host in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation.

The manner and method of carrying out the present invention may be more fully understood by those of skill by reference to the following examples, which examples are not intended in any manner to limit the scope of the present invention or of the claims directed thereto.

EXAMPLE 1

Isolation of *Trichoderma reesei* Genes Strongly Expressed on Glucose

For the isolation of glucose induced mRNA *Trichoderma reesei* strain QM9414 (Mandels, M. et al., *Appl. Microbiol.* 21:152–154 (1971)) was grown in a 10 liter fermenter in glucose medium (glucose 60 g/l, Bacto-Peptone 5 g/l, Yeast extract 1 g/l, $KH_2PO_4$ 4 g/l, $(NH_4)_2SO_4$ 4 g/l, $MgSO_4$ 0.5 g/l, $CaCl_2$ 0.5 g/l and trace elements $FeSO_4.7H_2O$ 5 mg/l, $MnSO_4.H_2O$ 1.6 mg/l, $ZnSO_4.7H_2O$ 1.4 mg/l, and $CoCl_2.6H_2O$ 3.7 mg/l, pH 5.0–4.0). Glucose feeding (465 g/20 h) was started after 30 hours of growth. Mycelium was harvested at 45 hours of growth and RNA was isolated according to Chirgwin, J. M. et al., *Biochem. J.* 18:5294–5299 (1979). Poly A+ RNA was isolated from the total RNA by oligo(dT)-cellulose chromatography (Maniatis, T. et al., *Molecular Cloning: A Laboratory Manual*, Cold Spring Harbor Laboratory, Cold Spring Harbor, N.Y. (1982)) and cDNA synthesis and cloning of the cDNAs was carried out according to manufacturer's instructions into lambda-ZAP vector (ZAP-cDNA synthesis kit, Stratagene). The cDNA bank was transferred onto nitrocellulose filters and screened with $^{32}$P-labelled single-stranded CDNA synthesized (Teeri, T. T. et al., *Anal. Biochem.* 164:60–67 (1987)) from the same poly A+ RNA from which the bank was constructed. The labelled cDNA was relabelled with $^{32}$P-dCTP (Random Primed DNA Labeling kit, Boehringer-Mannheim). The hybridization conditions were as described in Maniatis, T. et al., *Molecular Cloning: A Laboratory Manual*, Cold Spring Harbor Laboratory, Cold Spring Harbor, N.Y. (1982). Fifty clones giving the strongest positive reaction were isolated and the cDNAs were subcloned in vivo into Bluescript SK(−) plasmid according to manufacturer's instructions (ZAP-cDNA synthesis kit, Stratagene).

To identify the clones and exclude the same ones they were all sequenced from the 3' end by using standard methods. The frequency of each specific clone in the cDNA lambda-bank was determined by hybridizing the bank with a clone specific PCR probe. The clones cDNA33, cDNA1, DNA10, cDNA12, cDNA15, showing the five highest frequencies corresponded to 1–3% of the total mRNA pool.

EXAMPLE 2

Figure 2:
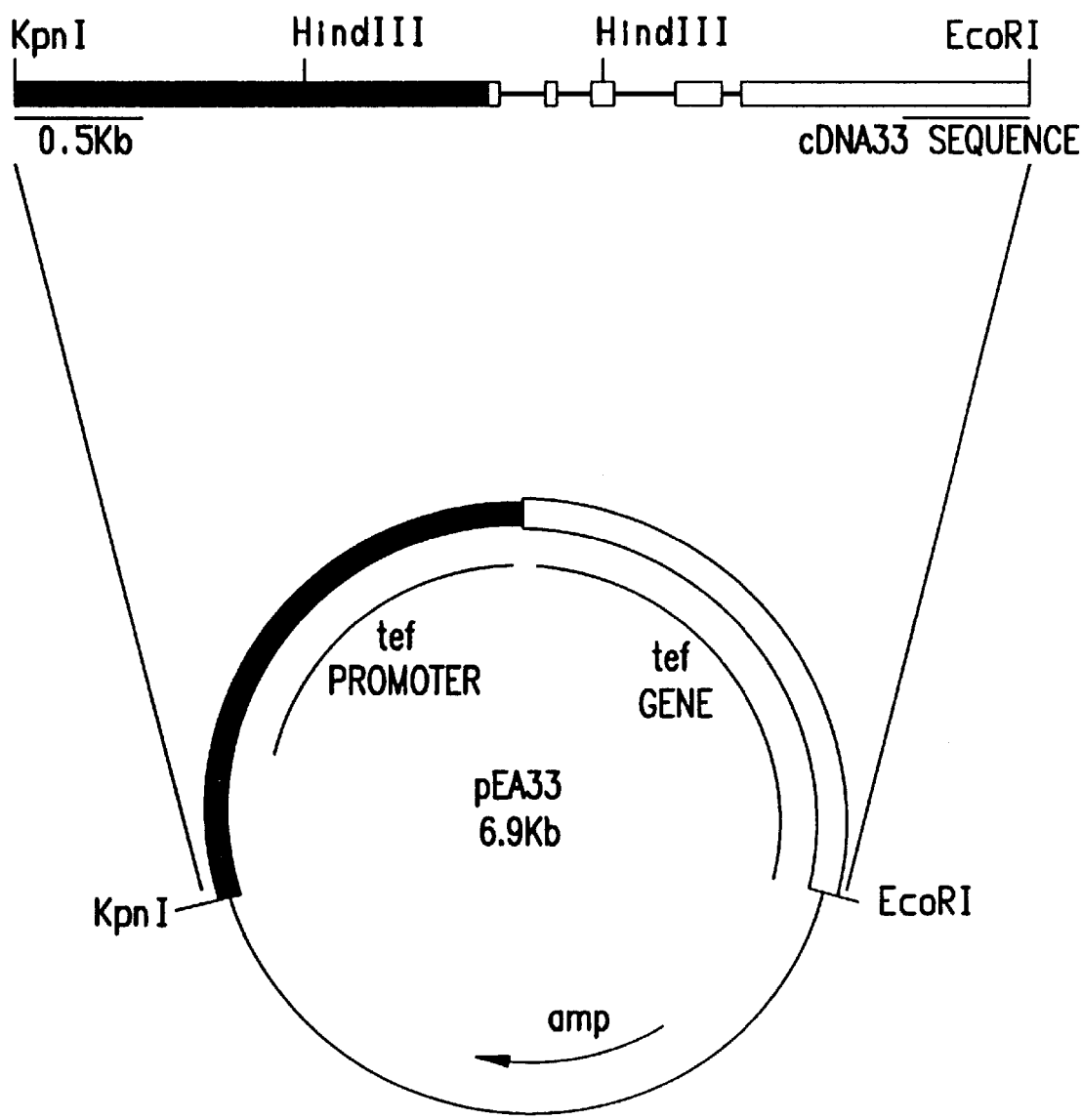
FIG. 2 shows the plasmid pEA33 which carries the tef1 promoter and the coding region with relevant features.
Figure 3A:
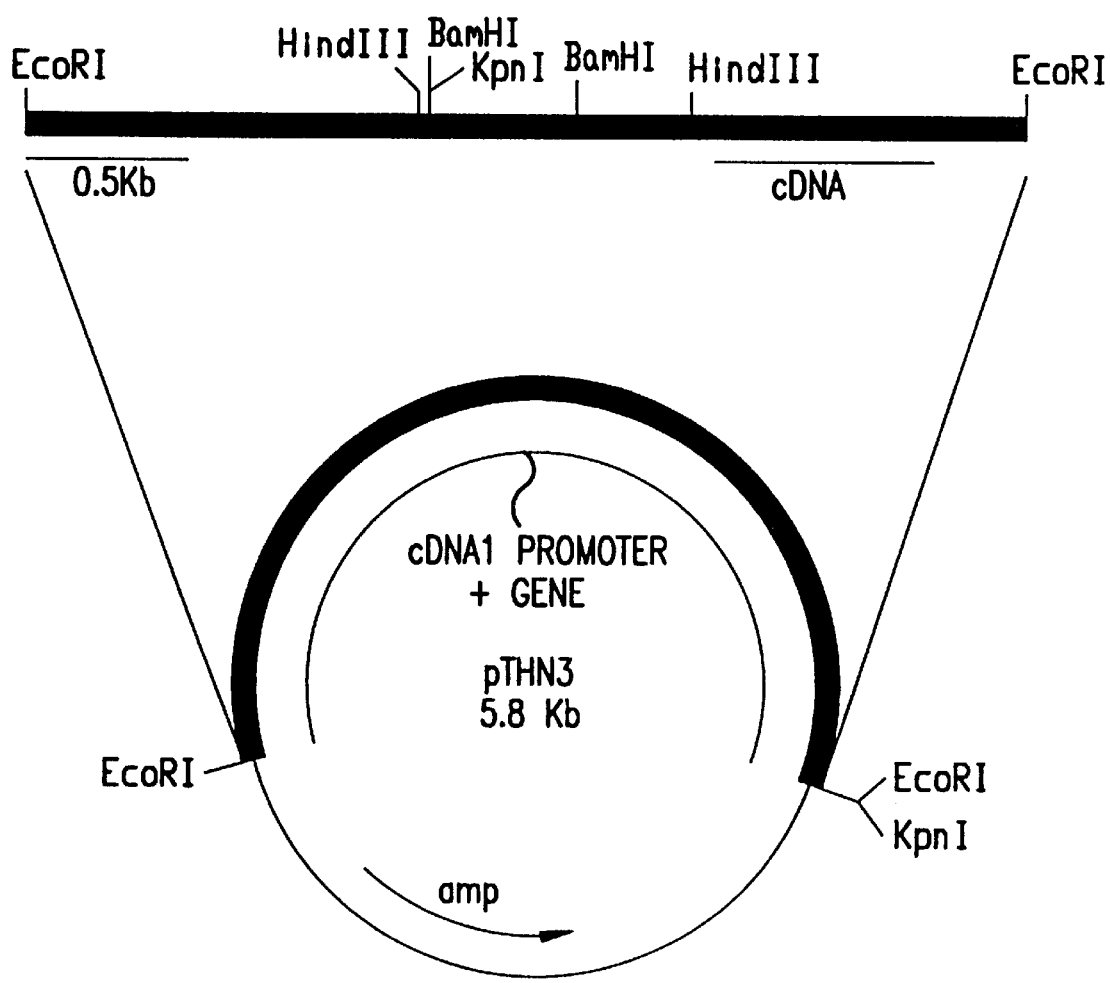
FIG. 3A shows the plasmid pTHN3 which carries the promoter and coding region of the clone cDNA1 and shows the relevant features.
Figure 4A:
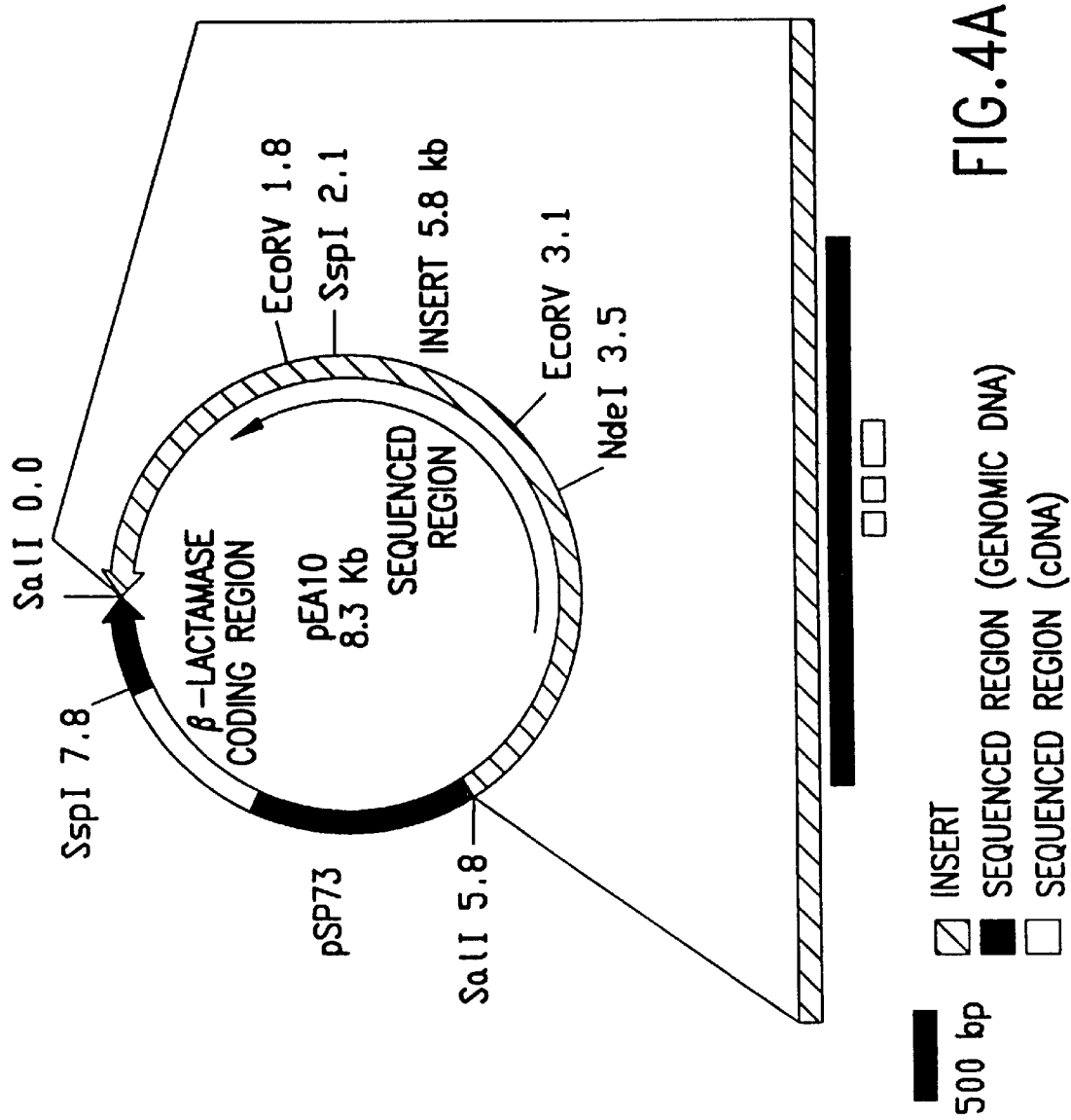
FIG. 4A shows the plasmid pEA10 which carries the promoter and coding region of the clone cDNA10 and the relevant regions and sequenced areas. Diagonally hatched=insert; solid line=sequenced region (genomic DNA); squared criss-crossed=sequenced region (cDNA). Not all EcoRV and NdeI sites are shown.
Figure 5A:
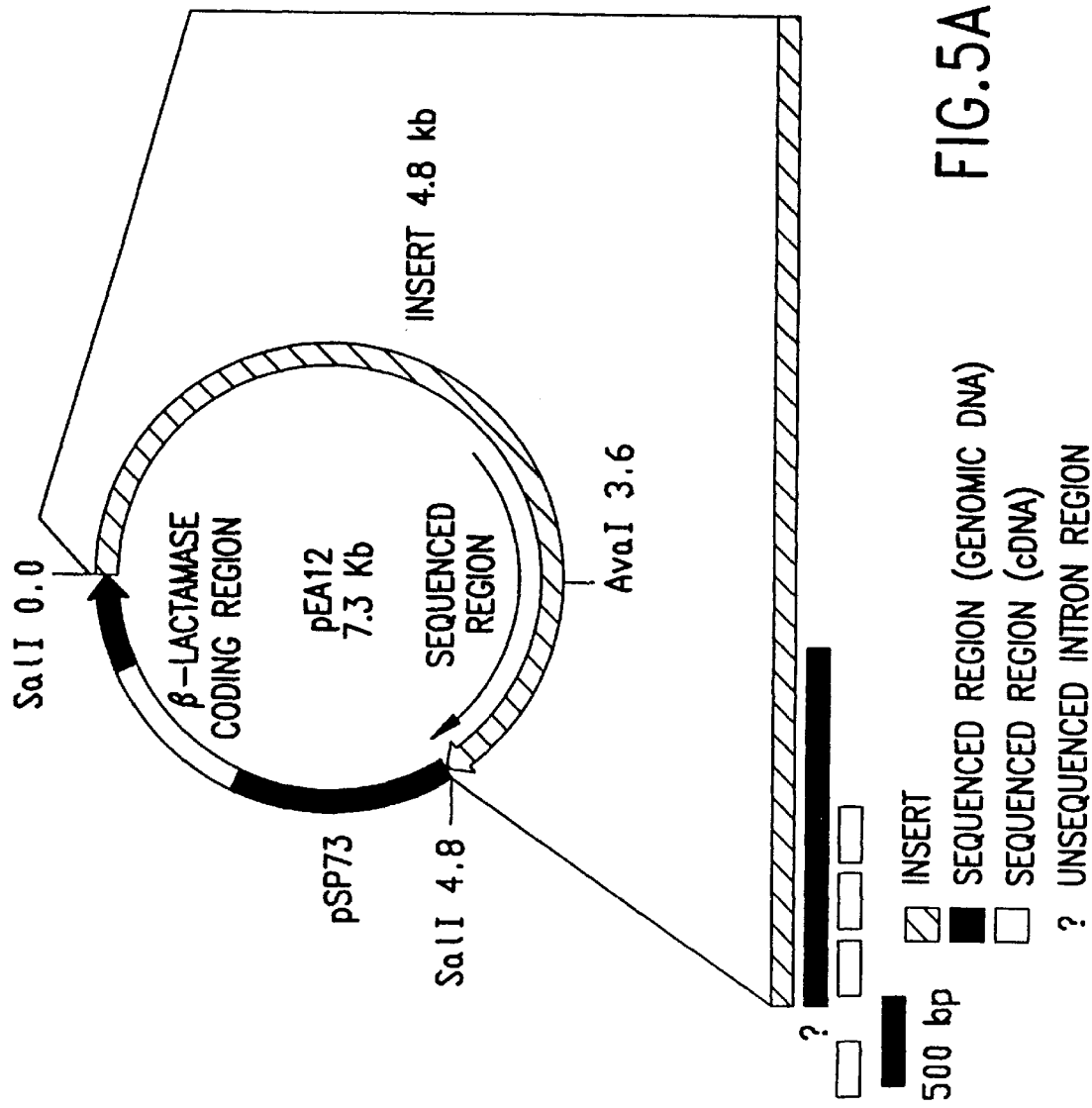
FIG. 5A shows the plasmid pEA12 which carries the clone cDNA12 and relevant features and sequenced areas. Diagonally hatched=insert; solid line=sequenced region (genomic DNA); squared criss-crossed=sequenced region (cDNA). ?=unsequenced intron region. Note: AvaI is not a unique site.
Figure 6A:
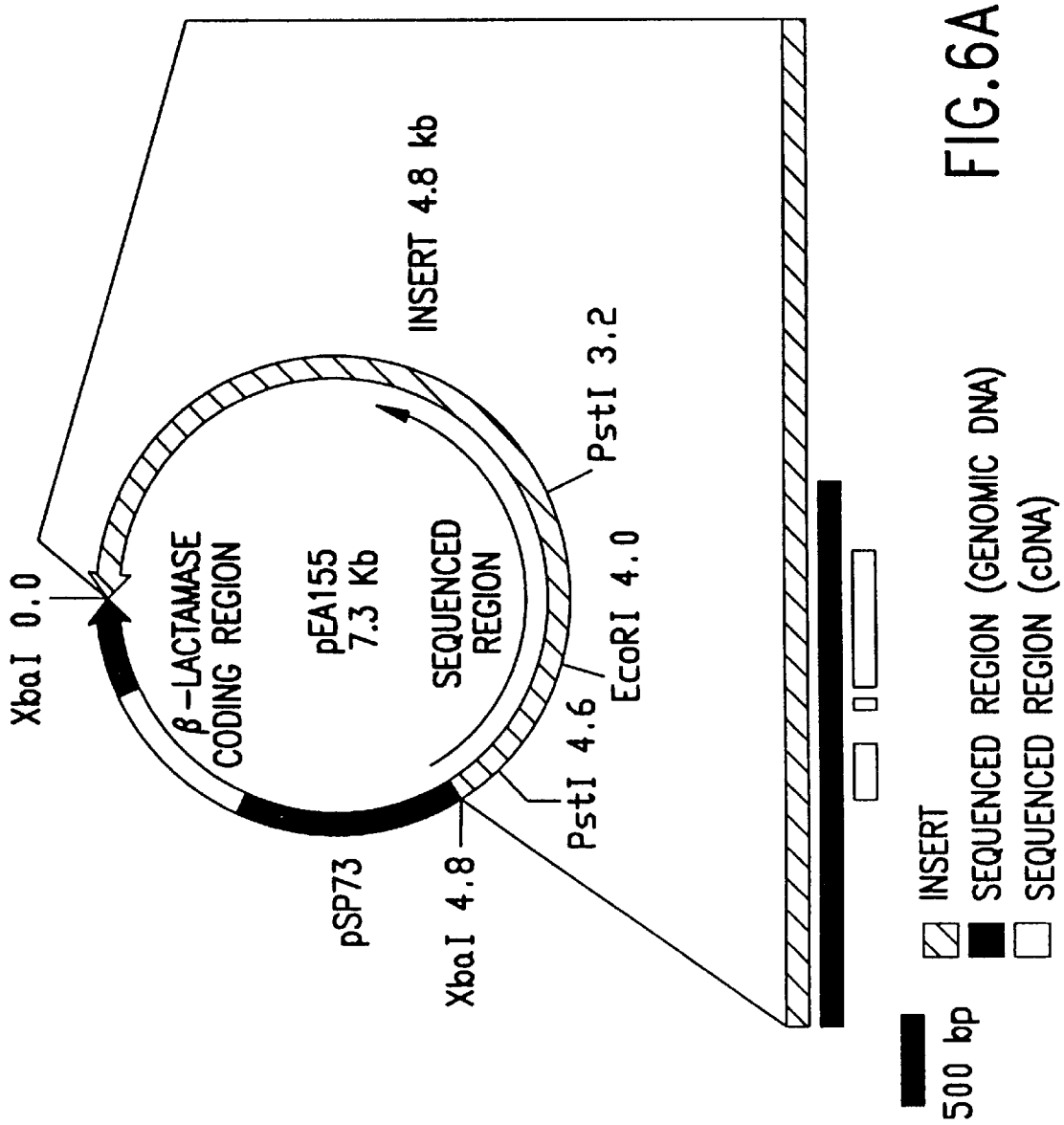
FIG. 6A shows the plasmid pEA155 which carries the promoter and coding region of the clone cDNA15 and the relevant features and sequenced areas. Diagonally hatched=insert; solid line=sequenced region (genomic DNA); squared criss-crossed=sequenced region (cDNA). Not all PstI and EcoRI sites are shown.

Characterization of Isolated Glucose Expressed Trichoderma Genes and Their Promoters The cDNAs of the clones cDNA33, cDNA1, cDNA10, cDNA12, and cDNA15 were used as probes to isolate the corresponding genes and promoters from a Trichoderma chromosomal lambda-bank prepared earlier (Vanhanen, S. et al., *Curr. Genet.* 15:181–186 (1989)). On the basis of Southern analysis of restriction enzyme digestions carried out for the chromosomal lambda clones, the promoters and either the 5' parts of the chromosomal genes or the whole genes were subcloned into pSP73 vector (Promega, Madison, USA) using appropriate restriction enzymes yielding the plasmids pTHN1 (FIG. 1), pEA33 (FIG. 2), pTHN3 (FIG. 3), pEA10 (FIG. 4), pEA12 (FIG. 5) and pEA155 (FIG. 6), corresponding to the clones cDNA33, CDNA1, CDNA10, cDNA12 and cDNA15, respectively. Sequences were obtained from the 5' ends of the genes and from the promoters using primers designed from previously obtained sequences. The sequences of the isolated promoters and genes or parts of them (either obtained from cDNA or chromosomal DNA) are shown in SEQ ID1 for cDNA33, SEQ ID2 for cDNA1, SEQ ID3 for cDNA10, SEQ ID4 for cDNA12, and SEQ ID5 for cDNA15. Based on sequence similarity to known sequences in a protein data bank the clone cDNA33could be identified as a translation elongation factor, TEF1 α.

Figure 7A:
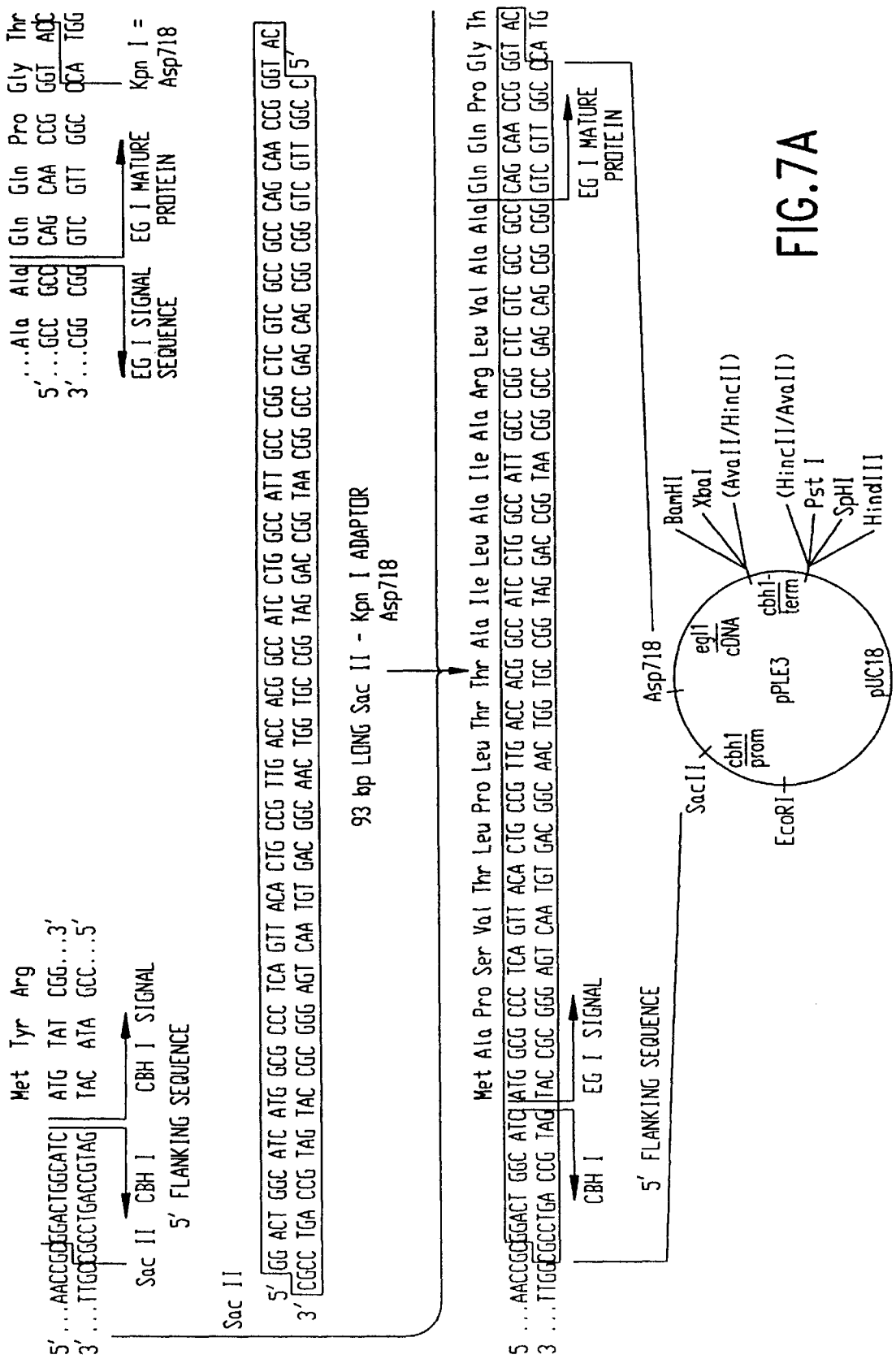
FIG. 7A shows plasmid pPLE3 which carries the egl1 cDNA. Just above the plasmid map is the sequence of the adaptor molecule [SEQ. ID 25] that was constructed to remove the small SacII and Asp718 fragment from the plasmid so as to construct an exact joint [SEQ ID 26, SEQ ID 27] between the cbh1 promoter and the egl1 signal sequences [SEQ IDs 18 and 16].

EXAMPLE 3
Construction of Vectors for Expression of EGI-core under the tef1-Promoter in Trichoderma A XhoI+DraIII fragment that is internal to the egl1 cDNA [SEQ ID 16 and FIG. 7B] sequence of plasmid pPLE3 (FIG. 7) carrying the EcoRI-BamHI fragment of egl1 cDNA from pTTc11 (Penttilä et al., Gene 45:253–263 (1986); Penttilä et al., Yeast 3:175–185 (1987) inbetween the cbh1 promoter and c. 700 nt long AvaII terminator fragment was replaced by a XhoI-DraIII fragment of cDNA from plasmid pEG131 (Nitisinprasert, S., Reports from Department of Microbiology, University of Helsinki (1990)). The pPLE3 insert sequence is egl1 cDNA in which a STOP codon is constructed just before the hinge region of the egl1 gene. The cbh1 terminator sequence is FIG. 7C [SEQ ID 23]. SEQ ID 23 is a shortened cbh1 terminator sequence, similar to SEQ ID 24 (the "long" cbh1 terminator but lacking 30 nucleotides at the 5' end).

pPLE3 contains a pUC18 backbone, and carries the cbh1 promoter inserted at the EcoRI site. The cbh1 promoter is operably linked to the full length egl1 cDNA coding sequence and to the cbh1 transcriptional terminator. The ori and amp genes are from the bacterial plasmid.

Figure 8:
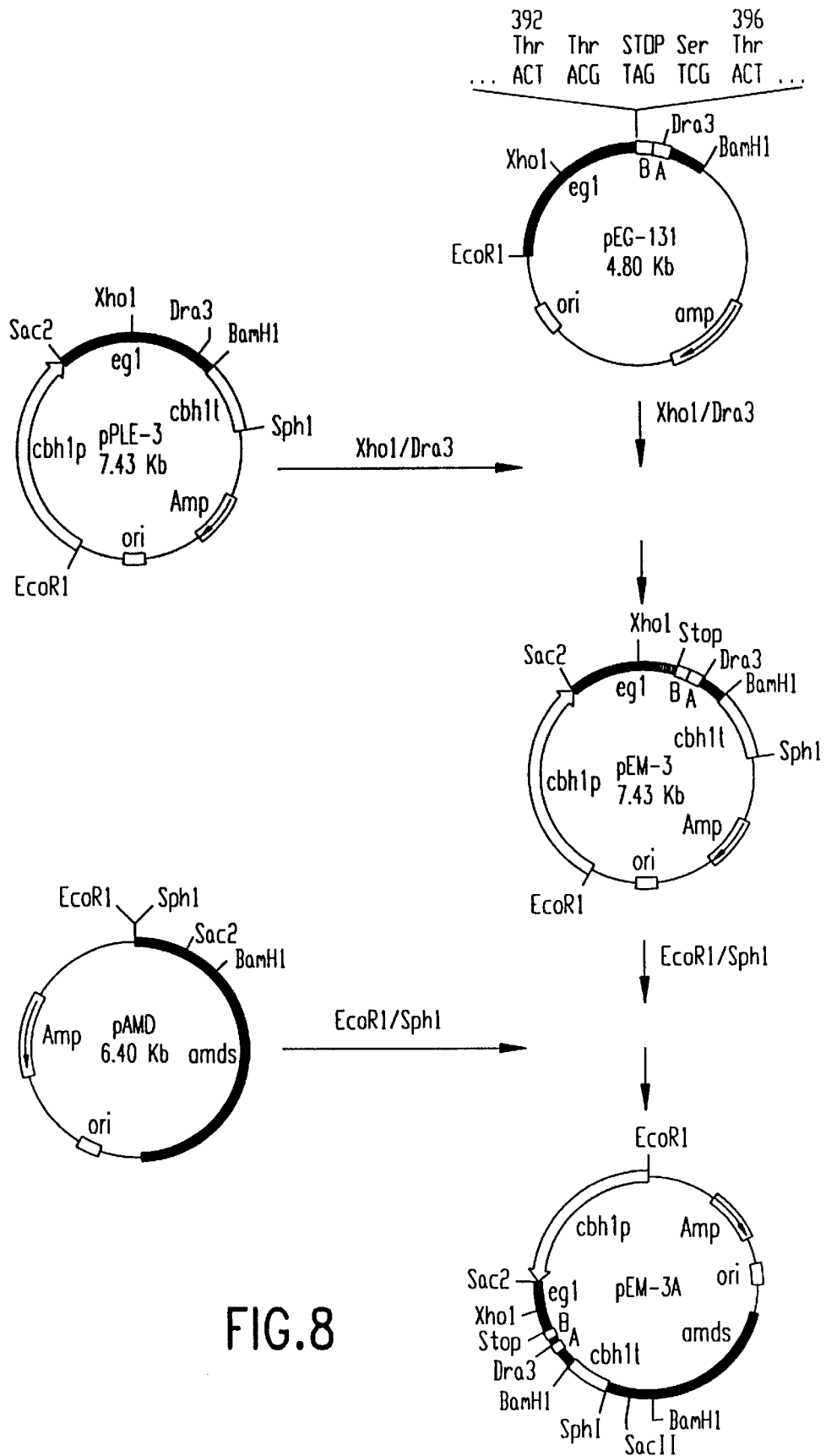
FIG. 8 shows construction of plasmid pEM-3A. The "A" on the plasmid maps denotes the EGI tail sequence and the "B" denotes the EGI hinge sequence SEQ ID 28 is also shown in the figure.

The resulting plasmid pEM-3 (FIG. 8) now carries a copy of egl1 cDNA with a translational stop codon after the egl1 core region (EGI amino acids 1–22 are the EGI signal sequence; EGI amino acids 23–393, terminating at a Thr, are considered the 'core' sequence). pEM-3 was then digested with EcoRI and SphI and the released Bluescribe M13+ moiety (Vector Cloning Systems, San Diego, USA) of the plasmid was replaced by EcoRI and SphI digested pAMD (FIG. 8) containing a 3.4 kb amdS fragment from plasmid p3SR2 (Hynes, M. J. et al., Mol. Cell. Biol. 3:1430–1439 (1983); Tilburn, J. et al., Gene 26:205–221 (1983). This resulting plasmid pEM-3A (FIG. 8) was digested with EcoRI and partially with KspI to release the 2.3 kb fragment carrying the cbh1-promotor and the 8.6 kb fragment carrying the rest of the plasmid was purified from agarose gel. Based on the sequence data of the tef1 promoter (SEQ ID1 bases 1–1234), two primers were designed (SEQ ID6 and SEQ ID7) and used in a PCR reaction to isolate a 1.2 kb promoter fragment adjacent to the translational start site of the tef1 gene. The 5' primer was ACCGGGAATTCATATCTAGAGGAGCCCGCGAGTTTGGATACGCC (SEQ ID6) and the 3' primer was ACCGCCGCGGTTTGACGGTTTGTGTGATGTAGCG (SEQ ID7).

Figure 9:
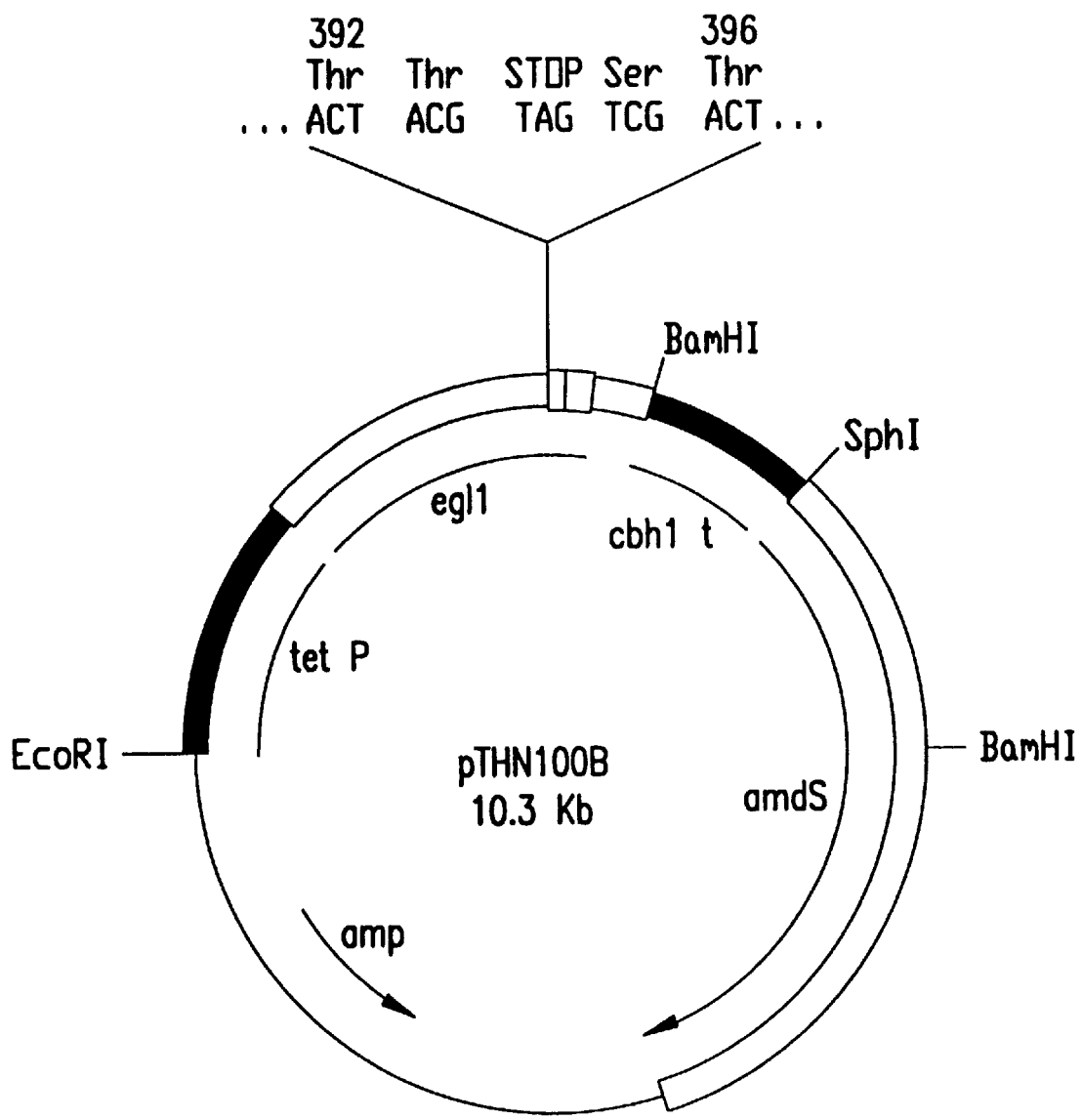
FIG. 9 shows the plasmid pTHN100B for expression of the EGIcore under the tef1 promoter SEQ ID 28 is also shown in the figure.

The bold and underlined GAATTC in the 5' primer is an EcoRI site. The bold and underlined TCTAGA in the 5' primer is an XbaI site. The bold and underlined CCGCGG in the 3' primer is a SacII site. This fragment was digested with EcoRI and partially with KspI and purified from agarose gel and ligated to the 8.6 kb pEM-3A fragment resulting in plasmid pTHN100B (FIG. 9). This expression vector carries DNA encoding the EGI-core construction operably linked to the tef1 promoter; this plasmid also carries an amdS marker gene for selection of Trichoderma transformants.

Figure 10:
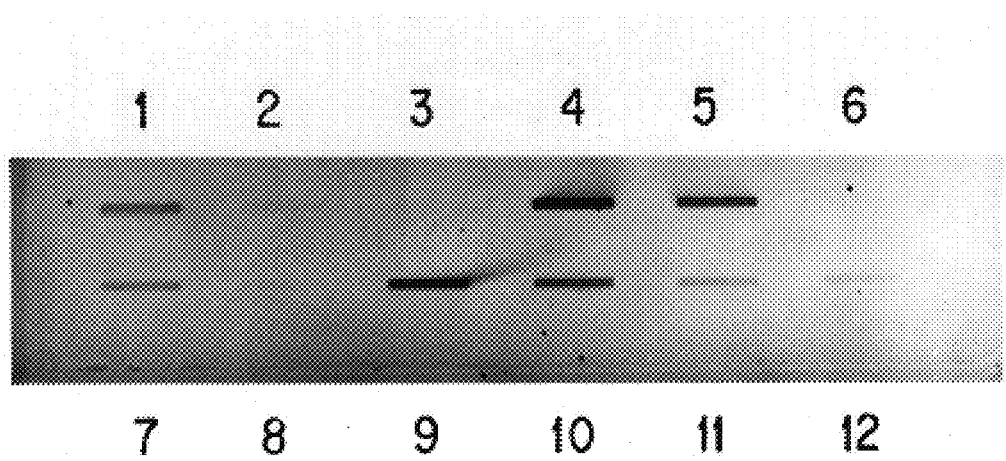
FIG. 10 shows production of EGIcore from the plasmid pTHN100B into the culture medium of the host strain QM9414 analyzed by EGI specific antibodies from a slot blot. Lane 1: pTHN100B-16b, 200 µl glucose supernatant; lane 2: QM9414, 200 µl glucose supernatant; lane 3: TBS; lane 4: QM9414, 200 µl solka floc 1:500 diluted supernatant; lane 5: QM9414, 200 µl solka floc 1:5,000 diluted supernatant; lane 6: QM9414, 200 µl solka floc 1:10,000 diluted supernatant; lane 7: pTHN100B-16b, 200 µl glucose 1:5 diluted supernatant; lane 8: QM9414, 200 µl glucose 1:5 diluted supernatant; lane 9: 200 ng EGI protein; lane 10: 100 ng EGI protein; lane 11: 50 ng EGI protein; and lane 12: 25 ng EGI protein.

EXAMPLE 4
Transformation of Trichoderma, Purification of the EGI-Core Producing Clones and Their Analysis Trichoderma reesei strain QM9414 was transformed essentially as described (Penttilä, M. et al., Gene 61:155–164 (1987) using 6–10 μg of the plasmid pTHN100B. The Amd$^+$ transformants obtained were streaked twice onto slants containing acetamide (Penttilä, M. et al. Gene 61:155–164 (1987)). Thereafter spore suspensions were made from transformants grown on Potato Dextrose agar (Difco). EGI-core production was tested by slot blotting with EGI specific antibody from 50 ml shake flask cultures carried out in minimal medium (Penttilä, M. et al. Gene 61:155–164 (1987)) supplemented with 5% glucose and using additional glucose feeding (total amount of fed glucose was 6 ml of 20% glucose). The spore suspensions of the EGI-core producing clones were purified to single spore cultures on Potato Dextrose agar plates. EGI-core production was analyzed again from these purified clones as described above (FIG. 10).

Figure 11:
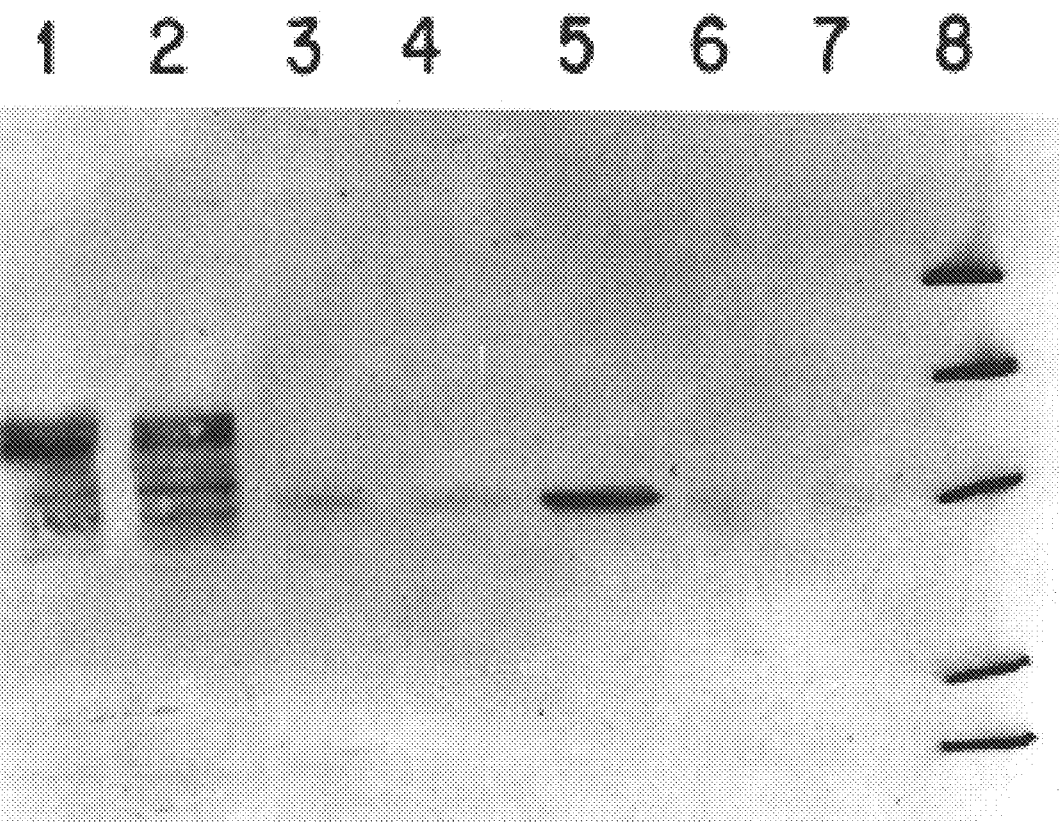
FIG. 11 shows Western blotting with EGI specific antibodies of culture medium of the strain pTHN100B-16c grown in whey-spent grain or glucose medium, and of EGIcore purified from the glucose medium. Lane 1: pTNH100B-16c, 10 µl whey spent grain supernatant; lane 2: pTNH100B-16c, 5 µl whey spent grain supernatant; lanes 3–5: EGIcore purified from pTHN100B-16c glucose fermentation; lane 6: pTHN100B-16c, 15 µl glucose fermenter supernatant, concentrated 100×; lane 7: pTHN100B-16c, 7.5 µl glucose fermenter supernatant, concentrated 100×; and lane 8: low molecular weight markers at 94 kDa, 67 kDa, 43 kDa, 30 kDa and 20.1 kDa (bands 1–5 starting from lane 8, top of gel).
Figure 12:
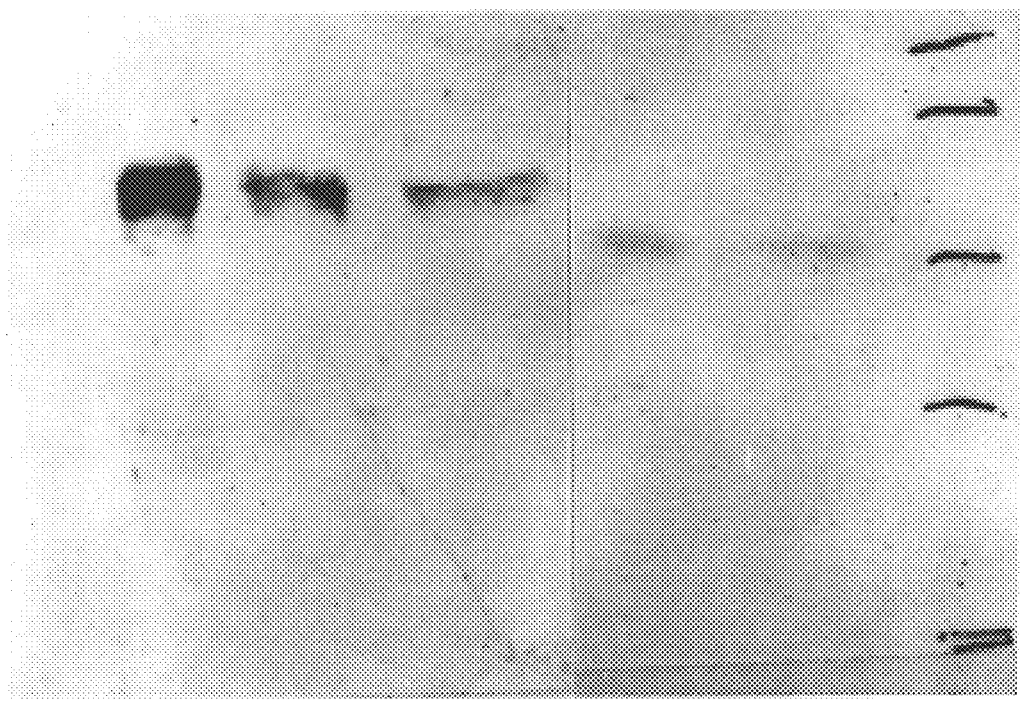
FIG. 12 shows Western blotting of culture medium of the strain pTHN100B-16c grown on glucose medium. Lane 1: EGI protein, about 540 ng; lane 2, EGI protein, about 220 ng; lane 3, EGI protein, about 110 ng; lane 4: pTHN100B-16c, 30 µl glucose fermenter supernatant; lane 5: pTHN100B-16c, 30 µl glucose fermenter supernatant, concentrated 4.2×; lane 6: low molecular weight markers at 94 kDa, 67 kDa, 43 kDa, 30 kDa and 20.1 kDa (bands 1–5 starting from lane 6, top of gel).

EXAMPLE 5
Characterization of EGI-core Produced by Trichoderma Grown on Glucose EGI-core producing strain pTHN100B-16c was grown in a 10 liter fermenter in glucose medium as described earlier in Example 1 except that yeast extract was left out and glucose feeding was 555 g/22 h. The culture supernatant was separated from the mycelium by centrifugation. The secretion of EGI-core by Trichoderma was verified by Western blotting by conventional methods running concentrated culture supernatants on SDS-PAGE and treating the blotted filter with monoclonal EGI-core specific antibodies (FIG. 11 and FIG. 12). The enzyme activity was shown semiquantitatively in a microtiter plate assay by using the concentrated culture supernatants and 3 mM chloronitrophenyl lactocide as a substrate and measuring the absorbance at 405 nm (Clayessens, M. et al., Biochem. J. 261:819–825 (1989)).

Figure 13A:
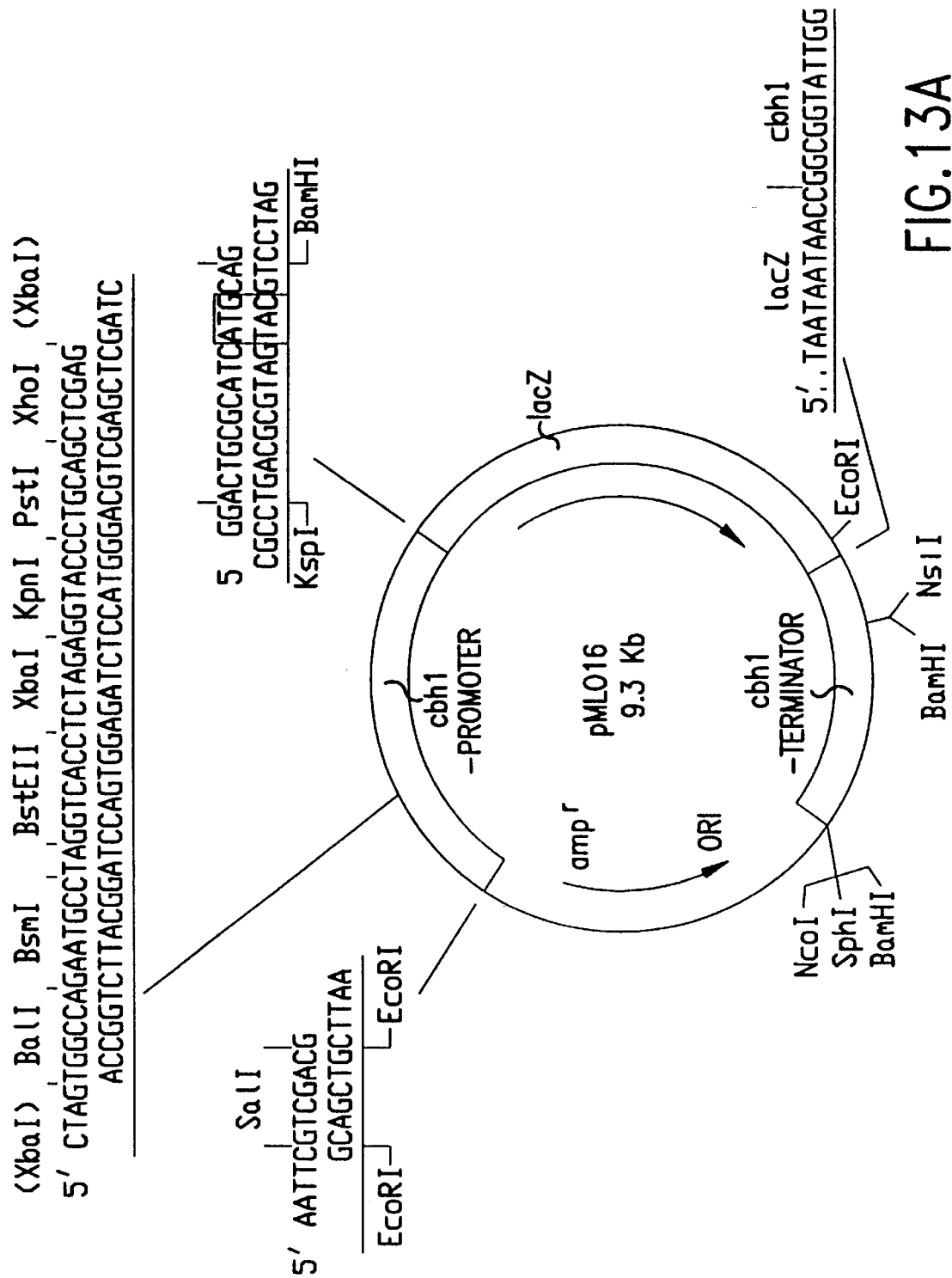
FIG. 13A diagrams the elements of the plasmid pMLO16.

EXAMPLE 6
Construction of β-Galactosidase Expression Vectors with Truncated Fragments of the cbh1-Promoter The vector pMLO16 (FIG. 13A) contains a 2.3 kb cbh1 promoter fragment ([SEQ ID18, FIG. 13B) starting at 5' end from the EcoRI site, isolated from chromosomal gene bank of Trichoderma reesei (Teeri, T. et al., Bio/Technology 1:696–699 (1983)), a 3.1 kb BamHI fragment of the lacZ gene from plasmid pAN924-21 (van Gorcom et al., Gene 40:99–106 (1985)) and a 1.6 kb cbh1 terminator (FIG. 13C, [SEQ ID 24]) starting from 84 bp upstream from the translation stop codon and extending to a BamHI site at the 3' end (Shoemaker, S. et al., Bio/Technology 1:691–696 (1983); Teeri, T. et al., Bio/Technology 1:696–699 (1983)). These pieces were linked to a 2.3 kb long EcoRI-PvuII region of pBR322 (Sutcliffe, J. G., Cold Spring Harbor Symp. Quant. Biol. 43:77–90 (1979)) generating junctions as shown in FIG. 13. The exact in frame joint between the 2.3 kb cbh1 promoter and the 3.1 kb lacZ gene was constructed by using an oligo depicted in FIG. 13. A polylinker shown in FIG. 13 was cloned into the single internal XbaI site in the cbh1 promoter for the purpose of promoter deletions. A short SalI linker shown in FIG. 13 was cloned into the joint between the pBR322 and cbh1 promoter fragments so that the expression cassette can be released from the vector by restriction digestion with SalI and SphI. Progressive unidirectional deletions were introduced to the cbh1 promoter by cutting the vector with KpnI and XhoI and using the Erase-A-Base System (Promega, Madison, USA) according to manufacturer's instructions. Plasmids obtained from different deletion time points were transformed into the *E. coli* strain DH5α (BRL) by the method described in (Hanahan D., *J. Mol. Biol.* 166:557–580 (1983)) and the deletion end points were sequenced by using standard methods.

EXAMPLE 7
Transformation of Trichoderma, Isolation of the β-Galactosidase Producing Clones and Their Analysis p

Figure 14:
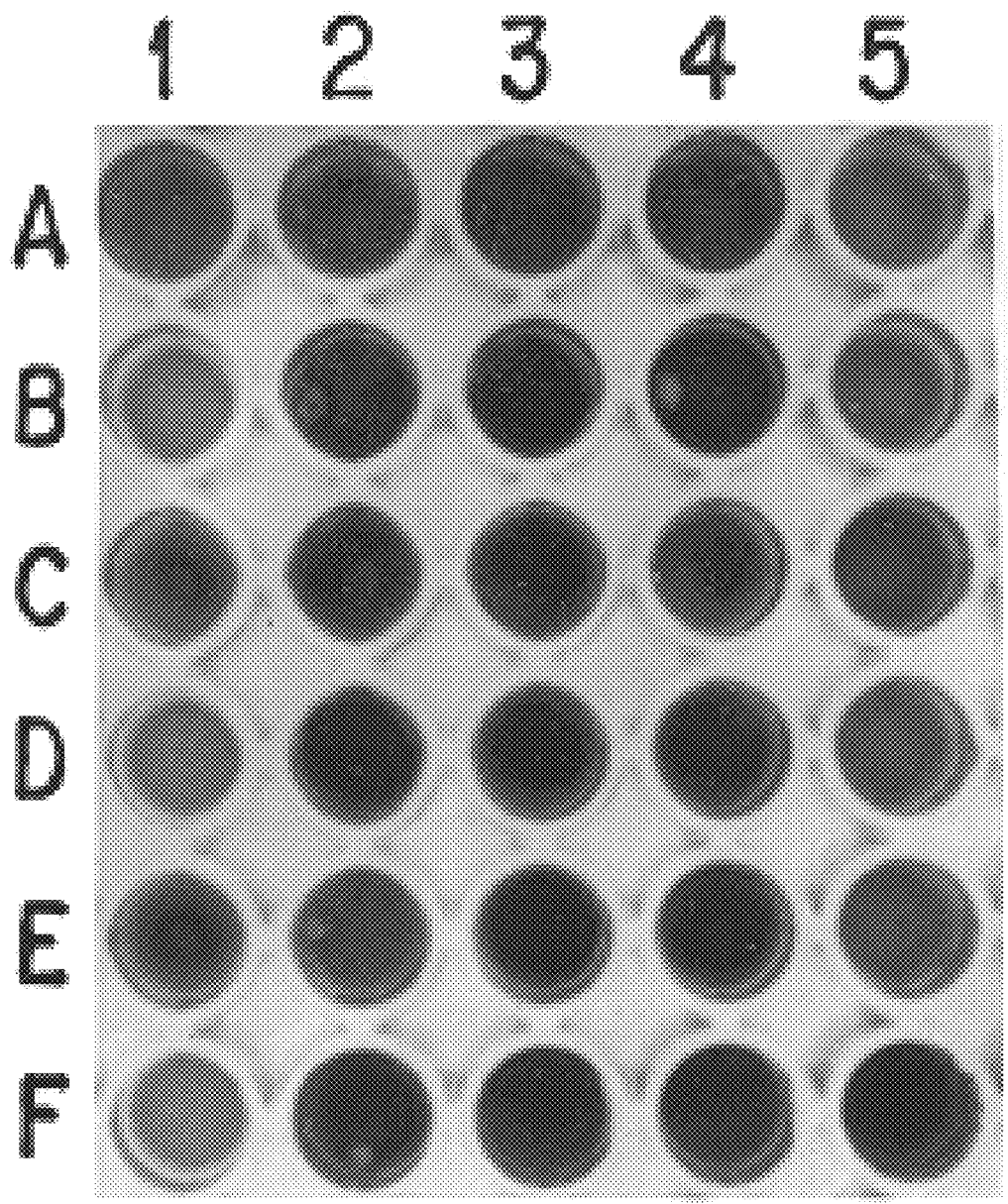
FIG. 14 shows the expression of β-galactosidase on glucose medium in pMLO16del5(11)-transformants of *Trichoderma reesei* QM 9414 (A2–F5). A1: QM 9414 host strain; C1 and E1: QM 9414 transformant in which one copy of β-galactosidase expression cassette with intact cbh1 promoter has replaced the cbh1 locus; B1, D1 and F1: empty wells.
Figure 15A:
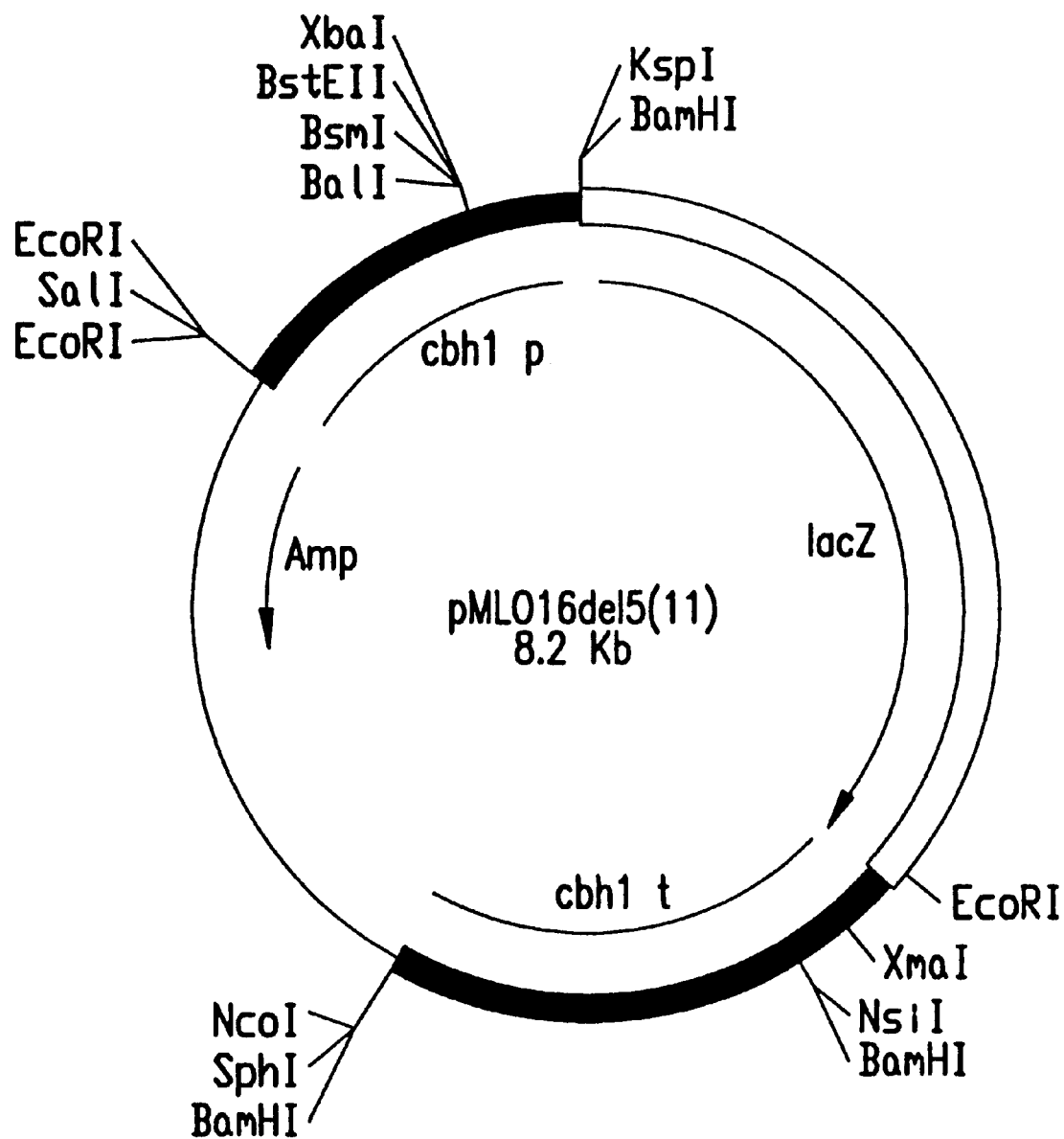
FIG. 15A shows the restriction map of the plasmid pMLO16del5(11), which carries the shortened form of the cbh1 promoter fused to the lacZ gene and the cbh1 terminator.

*Trichoderma reesei* strain QM9414 was transformed with expression vectors for β-galactosidase containing either the intact 2.3 kb cbh1 promoter or truncated versions of it, generated as explained in Example 6. Twenty μg of the plasmids were digested with SalI and SphI to release the expression cassettes from the vectors and these mixtures were cotransformed to Trichoderma together with 3 μg of plasmid p3SR2 (Hynes, M. J. et al., *Mol. Cell. Biol.* 3:1430–1439 (1983)) containing the acetamidase gene. The transformation method was that described in (Penttilä, M. et al. *Gene* 61:155–164 (1987)) and the Amd⁺ transformants were screened as described earlier in Example 4. The βgalactosidase production of the Amd⁺ transformants was tested by inoculating spore suspensions on microtiter plate wells containing solid minimal medium (Penttilä, M. et al. *Gene* 61:155–164 (1987)) supplemented with 2% glucose, 2% fructose and 0.2% peptone and pH adjusted to 7. After 24 h incubation in 28° C., 10 μl of the chromogenic substrate X-gal (20 mg/ml) was added to each well and the formation of blue color was followed as an indication of β-galactosidase activity. An intense blue color could be detected in transformants transformed with a plasmid pMLO16del5(11) (FIG. 14) containing a 1110 bp deletion in the cbh1 promoter beginning from the promoter internal polylinker and ending 385 bp before the translation initiation site (FIG. 15). The sequence of this truncated promoter is provided as SEQ ID19 (FIG. 15B).

Figure 16A:
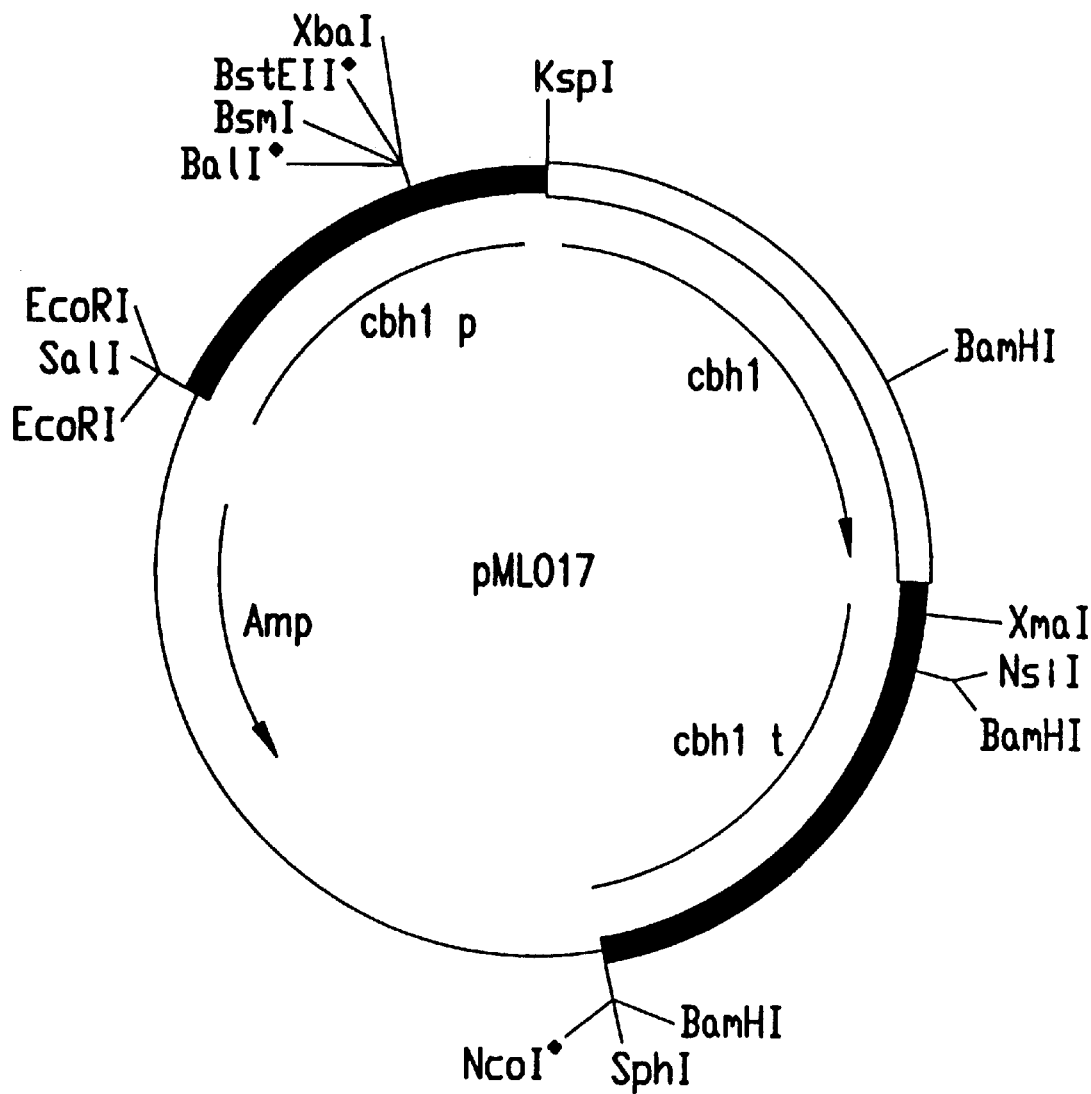
FIG. 16A shows the restriction map of the plasmid pMLO17, which carries the shortened form of the cbh1 promoter fused to the cbh1 chromosomal gene. The restriction sites marked with a superscripted cross "+" are not single sites. There are two additional EcoRI sites in the cbh1 gene that are not shown.
Figure 17A:
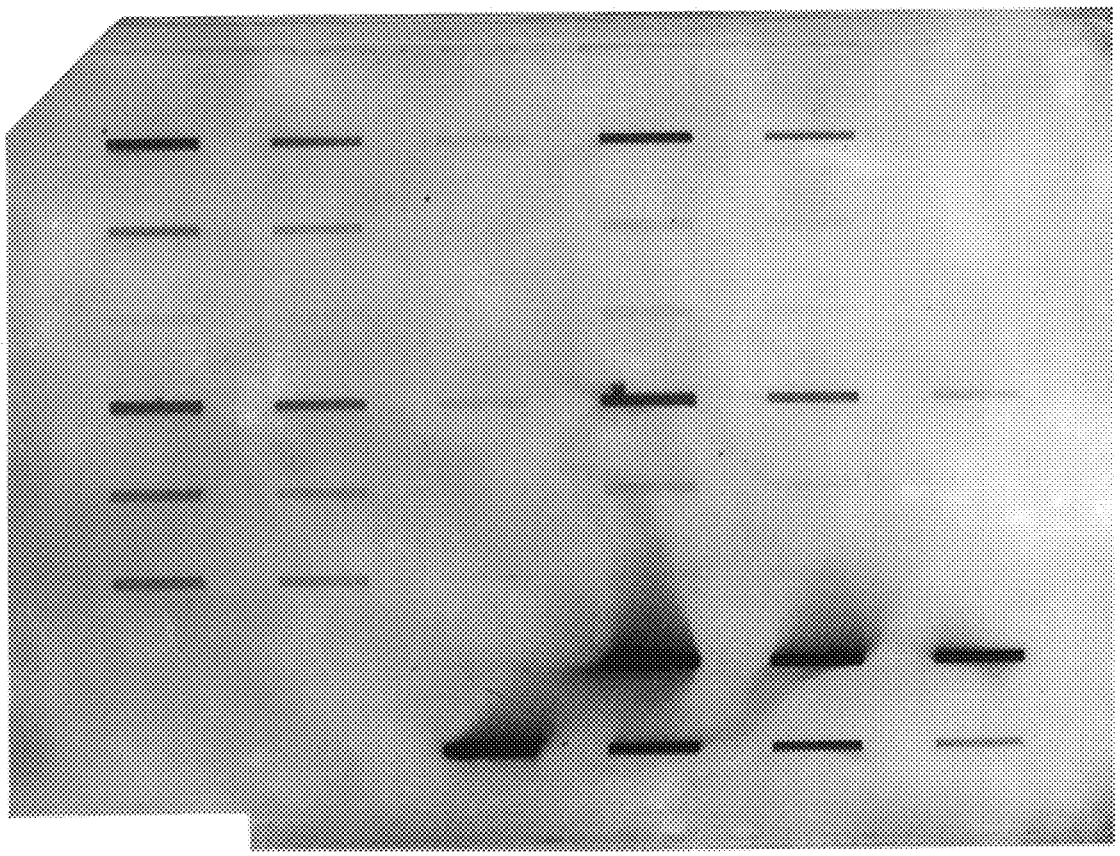
FIG. 17 shows the expression of CBHI on glucose medium in pMLO17 transformants of *Trichoderma reesei* QM 9414. A collection of single spore cultures (number and a letter-code) and different control samples are shown.

EXAMPLE 8
Production of CBHI on Glucose with the Glucose-Derepressed cbh1-Promoter For the production of CBHI on glucose an expression plasmid pMLO 17 (FIG. 16) was constructed. The plasmid pMLO16del5(11) was digested with the enzymes KspI (the first nucleotide of the recognition sequence is at the position −16 from the ATG) and XmaI (the first nucleotide of the recognition sequence is 76 nucleotides downstream from the translation stop codon of the cbh1 gene). The vector part containing the shortened cbh1 promoter, the cbh1 terminator and the pBR322 sequence was ligated to the chromosomal cbh1 gene isolated as a KspI-XmaI-fragment from the chromosomal gene bank of *Trichoderma reesei* (Teeri, T. et al., *Bio/Technology* 1:696–699 (1983)). The sequence of this fragment is provided as the underlined portion of FIG. 16B ([SEQ ID17]). The plasmid pMLO17 was transformed to the *Trichoderma reesei* strain QM 9414 and the Amd⁺ transformants were screened as described earlier in example 7. CBHI production was tested from 40 transformants in microtiter plate cultures (200 μl; 3 days) carried out in minimal medium (Penttilä, M. et al. *Gene* 61:155–164 (1987) supplemented with 3% glucose and using additional glucose feeding (total amount of fed glucose was 6 mg/200 μl culture). The culture supernatants were slot blotted on nitrocellulose filters and CBHI was detected with specific antibody. The spore suspensions of the 10 best CBHI producing transformants were purified to single spore cultures on plates containing acetamide and Triton X-100 (Penttilä, M. et al., *Gene* 61:155–164 (1987)). Thirty single spore cultures were tested for CBHI production in shake flask cultivations (50 ml; 6 days) carried out in the same medium as described above. The total amount of fed glucose was 1.8 g/50 ml culture. Dilutions of the culture supernatants were slot blotted and CBHI was detected with specific antibody (FIG. 17).

Figure 18A:
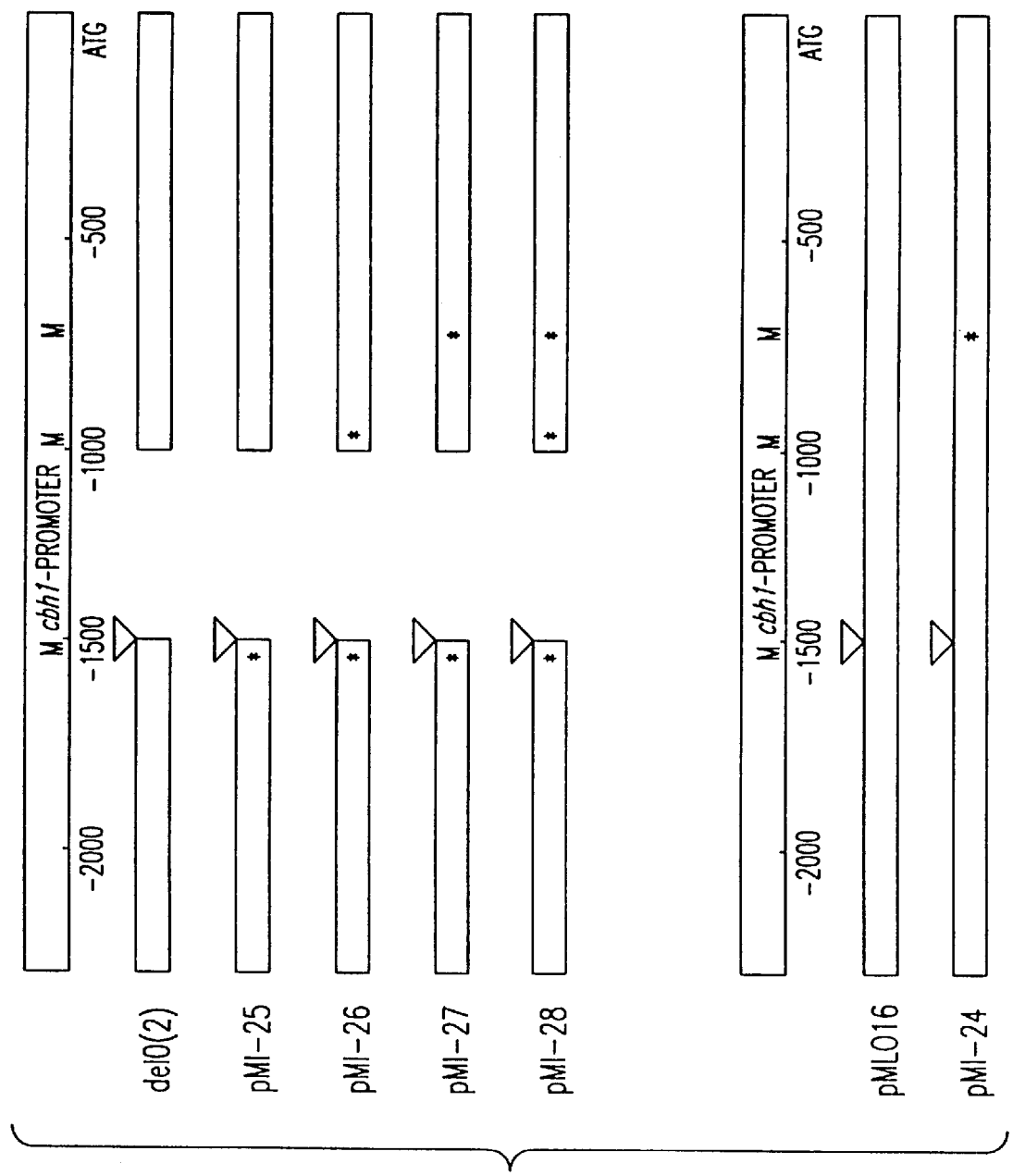
FIG. 18A shows specific mutations of mig-like sequences (M) in cbh1 promoters of pMI-24, pMI-25, pMI-26, pMI-27 and pMI-28. The promoters shown here were fused to lacZ gene and cbh1 terminator as described for pMLO16 (see FIG. 13) or pMLO16del0(2) (see FIG. 19). *: sequence alteration made in cbh1 promoter in different combinations. At position −1505–1500 the genomic sequence is 5'-CTGGGG and the altered sequence is 5'-TCTAAA. At position −1001–996 the genomic sequence is 5'-CTGGGG and the altered sequence is 5'-TCTAAA. At position −720–715 the genomic sequence is 5'-GTGGGG and the altered sequence is 5'-TCTAGA. pMLO16del0(2) was used as a starting vector for pMI-25, pMI-26, pMI-27 and pMI-28, pMLO16 for pMI-24. ▽=the polylinker.
Figure 19:
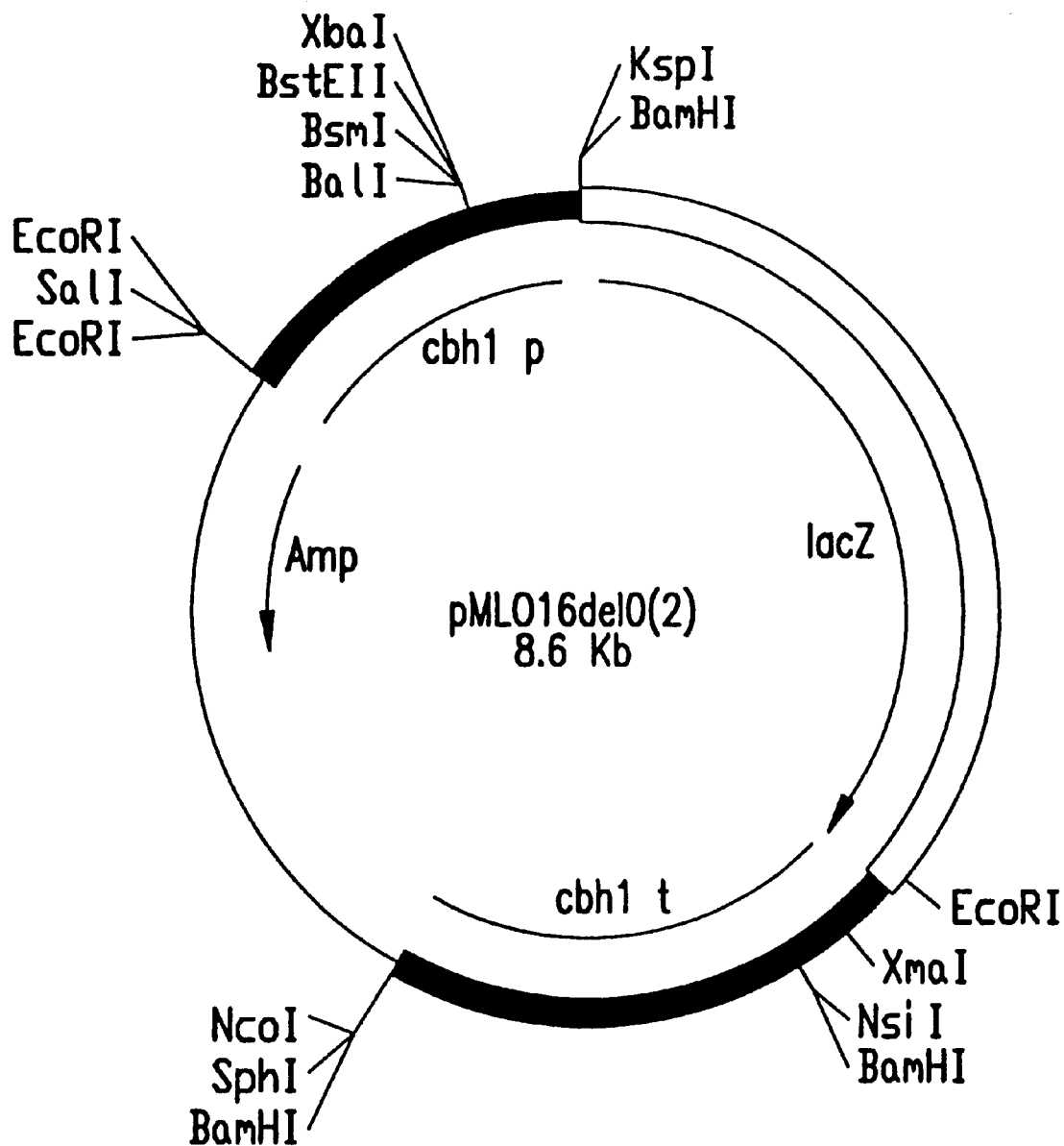
FIG. 19 shows the restriction map of the plasmid pMLO16del0(2), which carries the shortened form of the cbh1 promoter fused to lacZ gene and the cbh1 terminator.

EXAMPLE 9
β-Galactosidase Expression Vectors with Specific Mutations in cbh1 Promoter to Release Glucose Repression Three 6 bp sequences found in cbh1 promoter similar to binding sites of *Saccharomyces cerevisiae* glucose repressor protein MIG1 (Nehlin & Ronne, *EMBO J.* 9:2891–2899 (1990); Nehlin et al., *EMBO J.* 10:3373–3377 (1991)) were changed into other nucleotides to study the functionality of these mig-like sequences in mediating the glucose repression of the native cbh1 promoter of *Trichoderma reesei*. To construct β-galactosidase expression vectors with cbh1 promoters carrying specific mutations, sequence alterations were made into primers (specifically: TCT TCA AGA ATT GCT CGA CCA ATT CTC ACG GTG AAT GTA GG (SEQ ID 8); ACA CAT CTA GAG GTG ACC TAG GCA TTC TGG CCA CTA GAT ATA TAT TTA GAA GGT TCT TGT AGC TCA AAA GAG C (SEQ ID 9); GGG AAT TCT CTA GAA ACG CGT TGG CAA ATT ACG GTA CG (SEQ ID 10); GGG AAT TCG GTC ACC TCT AAA TGT GTA ATT TGC CTG CTT GAC C (SEQ ID 11); GGG AAT TCG GTC ACC TCT AAA TGT GTA ATT TGC CTG CTT GAC CGA TCT AAA CTG TTC GAA GCC CGA ATG TAG G (SEQ ID 12); GGG AAT TCT TCT AGA TTG CAG AAG CAC GGC AAA GCC CAC TTA CCC (SEQ ID 13); TAG CGA ATT CTA GGT CAC CTC TAA AGG TAC CCT GCA GCT CGA GCT AG (SEQ ID 14); and GGG AAT TCA TGA TGC GCA GTC CGC GG (SEQ ID 15); these primers were specific for the cbh1 promoter and the cbh1 promoter internal polylinker and were used in PCR amplification of cbh1 promoter sequences for cloning.

pMLO16(FIG. 13) was used as a PCR template with the appropriate primers to yield a 770 bp fragment A (primers TAG CGA ATT CTA GGT CAC CTC TAA AGG TAC CCT GCA GCT CGA GCT AG (SEQ ID 14) and GGG AAT TCT CTA GAA ACG CGT TGG CAA ATT ACG GTA CG (SEQ ID 10), beginning at the polylinker at −1500 and ending at −720 upstream of ATG, and a 720 bp fragment B (primers GGG AAT TCT TCT AGA TTG CAG AAG CAC GGC AAA GCC CAC TTA CCC (SEQ ID 13) and GGG AAT TCA TGA TGC GCA GTC CGC GG (SEQ ID 15)), beginning at −720 and ending at KspI at −16. Fragments A and B were purified from agarose gel and digested with BstEII-XbaI and XbaI-KspI respectively, ligated to the 7.8 kb fragment of pMLO16to produce pMI-24. The resulting cbh1 promoter carries a sequence alteration (genomic sequence 5' GTGGGG, altered sequence: 5' TCTAGA) at position −720 to −715 upstream of the translation initiation codon of intact cbh1 promoter (FIG. 18). The sequence of the altered cbh1 promoter in pMI-24 is provided in FIG. 18B and SEQ ID20.

pMLO16del0(2) (FIG. 19) containing a 460 bp deletion in the cbh1 promoter beginning from the promoter internal polylinker and ending 1025 bp before the translation initiation site was constructed as described in Example 6 and used as a PCR template with primers (TCT TCA AGA ATT GCT CGA CCA ATT CTC ACG GTG AAT GTA GG (SEQ ID 8) and ACA CAT CTA GAG GTG ACC TAG GCA TTC TGG CCA CTA GAT ATA TAT TTA GAA GGT TCT TGT AGC TCA AAA GAG C (SEQ ID 9)) to yield a 800 bp fragment C, beginning from the 5' end of cbh1 promoter and ending at the promoter internal polylinker. Fragment C was purified from agarose gel, digested with SalI-XbaI and ligated to the 7.6 kb SalI-XbaI fragment of pMLO16del0(2) to produce pMI-25. The cbh1 promoter of pMI-25 has a sequence alteration (genomic sequence: 5'GTGGGG, altered sequence: 5'TCTAAA) at position −1505–1500 upstream of the translation initiation codon of intact cbh1 promoter (FIG. 18).

pMLO16del0(2) was used as a PCR template to yield a 750 bp fragment D (primers GGG AAT TCG GTC ACC TCT AAA TGT GTA ATT TGC CTG CTT GAC CGA TCT AAA CTG TTC GAA GCC CGA ATG TAG G (SEQ ID 12) and GGG AAT TCA TGA TGC GCA GTC CGC GG (SEQ ID 15)), beginning from the promoter internal polylinker and ending at KspI at −16. Fragment D was purified from agarose gel, digested with BstEII-KspI and ligated to the 7.8 kb BstEII-KspI fragment of pMI-25 to produce pMI-26. The cbh1 promoter of pMI-26 has sequence alterations at positions −1505–1500 (genomic sequence: 5'GTGGGG, altered sequence: 5'TCTAAA) and −1001–996 (genomic sequence: 5'CTGGGG, altered sequence: 5'TCTAAA) upstream of the translation initiation codon of intact cbh1 promoter (FIG. 18).

pMLO16del0(2) was used as a PCR template to yield a 280 bp fragment E (primers GGG AAT TCT CTA GAA ACG CGT TGG CAA ATT ACG GTA CG (SEQ ID 10) and GGG AAT TCG GTC ACC TCT AAA TGT GTA ATT TGC CTG CTT GAC C (SEQ ID 11)), beginning from the promoter internal polylinker and ending at −720 and a 720 bp fragment F (primers GGG AAT TCT TCT AGA TTG CAG AAG CAC GGC AAA GCC CAC TTA CCC (SEQ ID 13) and GGG AAT TCA TGA TGC GCA GTC CGC GG (SEQ ID 15)), beginning at −720 and ending at KspI at −16. Fragments D and E were purified from agarose gel, digested with BstEII-XbaI and XbaI-KspI respectively and ligated to the 7.8 kb BstEII-KspI fragment of pMI-25 to produce pMI-27. The cbh1 promoter of pMI-27 has sequence alterations at positions −1505–1500 (genomic sequence: 5'GTGGGG, altered sequence: 5'TCTAAA) and −720–715 (genomic sequence: 5'GTGGGG, altered sequence: 5'TCTAGA) upstream of the translation initiation codon of intact cbh1 promoter (FIG. 18). The sequence of the altered cbh1 promoter of pMI-27 is shown in FIG. 18C and SEQ ID21.

pMLO16del0(2) was used as a PCR template to yield a 280 bp fragment G (primers GGG AAT TCT CTA GAA ACG CGT TGG CAA ATT ACG GTA CG (SEQ ID 10) and GGG AAT TCG GTC ACC TCT AAA TGT GTA ATT TGC CTG CTT GAC CGA TCT AAA CTG TTC GAA GCC CGA ATG TAG G (SEQ ID 12)), beginning from the promoter internal polylinker and ending at −720 and a 720 bp fragment H (primers GGG AAT TCT TCT AGA TTG CAG AAG CAC GGC AAA GCC CAC TTA CCC (SEQ ID 13) and GGG AAT TCA TGA TGC GCA GTC CGC GG (SEQ ID 15)), beginning at −720 and ending at KspI at −16. Fragments G and H were purified from agarose gel, digested with BstEII-XbaI and XbaI-KspI respectively and ligated to the 7.8 kb BstEII-KspI fragment of pMI-25 to produce pMI-28. The cbh1 promoter of pMI-28 has sequence alterations at positions −1505–1500 (genomic sequence: 5'GTGGGG, altered sequence: 5'TCTAAA), −1001–996 (genomic sequence: 5'CTGGGG, altered sequence: 5'TCTAAA), and −720–715 (genomic sequence: 5'GTGGGG, altered sequence: 5'TCTAGA) upstream of the translation initiation codon of intact cbh1 promoter (FIG. 18). The sequence of the altered cbh1 promoter of pMI-28 is shown in FIG. 18D and SEQ ID22.

Figure 20:
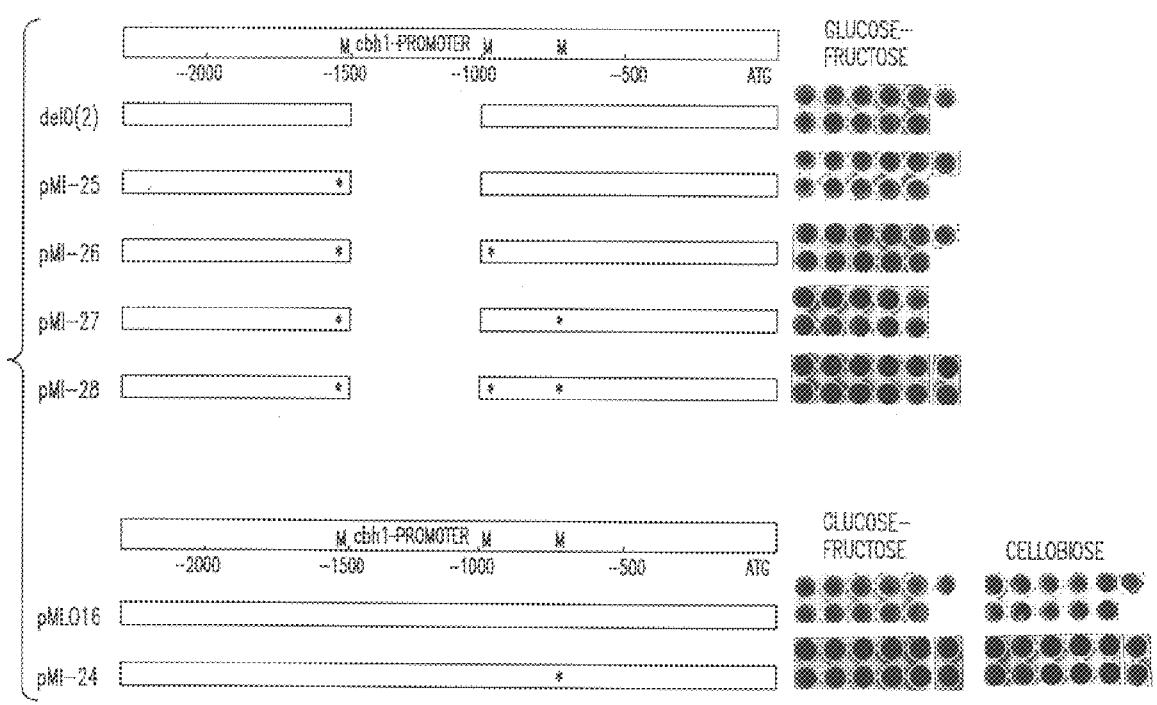
FIG. 20 shows the expression of β-galactosidase on indicated medium in *Trichoderma reesei* QM9414 transformed with pMLO16del0(2), pMI-25, pMI-27, pMI-28, pMLO16 and pMI-24.

All PCR amplified DNA fragments and ligation joints were sequenced using standard methods to ensure that the mutations were present and no other nucleotides were changed. Transformation of *Trichoderma reesei* QM9414 with the vectors mentioned above, isolation of β-galactosidase producing clones and their analysis was done as described in Example 7. After addition of X-gal, an intense blue color was detected on glucose grown transformant colonies as an indication of β-galactosidase activity in transformants transformed with the plasmids pMI-24, pMI-27 and pMI-28 (FIG. 20), indicating that altering the cbh1 promoter according to any of those mutations was sufficient to allow for expression of proteins in Trichoderma under the cbh1 promoter in the presence of glucose.

What is claimed is:

1. A method for cloning a promoter, said method comprising:
   (a) extracting mRNA from cells;
   (b) preparing a cDNA bank from said mRNA and cloning said cDNA bank;
   (c) detectably labelling a sample of cDNA that had been synthesized against said mRNA;
   (d) hybridizing the detectably labelled sample of step (c) to the cloned cDNA bank of step (b) under conditions in which the clones hybridize with varying intensity such that cDNAs that are the most abundant give the strongest signals;
   (e) selecting from the hybridization of step (d) clones showing the strongest signals as compared to the signals of other clones in the hybridization;
   (f) determining the frequency with which a clone selected in step (e) is represented in said mRNA by preparing a clone-specific probe, hybridizing said probe against said cDNA bank of step (b), and determining the percent of the total cDNA bank that said clones identified in step (e) represents;
   (g) selecting clones showing the strongest signals as compared to the signals of other clones in the hybridization of step (d) and that are present at a desired frequency as determined in step (f);
   (h) using the clone-specific sequence of the clones selected in step (g) to identify the corresponding gene; and
   (i) cloning the promoter of said gene.

2. The method of claim 1, wherein the cells are filamentous fungi.

3. The method of claim 1, wherein the cells are selected from the group consisting of Trichoderma, Aspergillus, *Claviceps purpurea, Penicillium chrysogenum, Magnaporthe grisea,* Neurospora, Mycosphaerella spp., *Collectotrichum trifolii,* the dimorphic fungus *Histoplasmia capsulatum, Nectria haematococca* (anamorph:*Fusarium solani* f. sp. phaseoli and f. sp. pisi), *Ustilago violacea, Ustilago maydis, Cephalosporium acremonium, Schizophyllum commune, Podospora anserina, Sordaria macrospora, Mucor circinelloides,* and *Collectotrichum capsici*.

4. The method of claim 3, wherein the cells are Trichoderma.

5. The method of claim 4, wherein the cells are *T. reesei*.

* * * * *

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 3461 base pairs
      (B) TYPE: nucleic acid
      (C) STRANDEDNESS: single
      (D) TOPOLOGY: linear (xi) SEQUENCE DESCRIPTION: SEQ ID NO:1:

```
CGCCGTGACG ACAGAAACGG AGCCCGCGAG TTTGGATACG CCGCTGAAAT GGGGCTTGAC      60

GGTGAAGGAG AAGCCGAGCG CGGTGCCAGA GGACAAGATG GATGTAGAGC CAGGCGACGA     120

CGACCAAACG CAACCATCAA ATCAATCAGA TGGCAATGAC GCACCACCGC CCCAGCAGCG     180

CGAACCGCCG ACGAAGAAGC CATGGACGCG CTCCTCGGCA AGACGCCCAA GGAACAGAAA     240

AAAGTAATCT CCGCACCCGT ATCAGAAGAC GACGCCTACC GCCGCGACGT CGAAGCCTCC     300
```

```
GGCGCGGTGT CCACGCTCCA GGATTACGAA GACATGCCCG TCGAGGAGTT TGGCGCCGCC      360

CTCCTCCNNN GCATGGGCTG GAACGGGGAA GCCCGCGGCC CGCCGGTCAA GCAGGTCAAG      420

AGGCGGCAGA ACAGGCTCGG CCTCGGCGCC AAGGAGCTCA AGGAGGAAGA GGACCTCGGC      480

GGGTGGAACC AGAACGGCAA GAAAAAGTCG AGGCCSCGCG GCTGAGCGAG TATCGGAGGG      540

AGGAGAGCAA GCGCAAGGAA GGCCGGGGGC ATGAGGACAG CTATAAACGA GAGAGGGAGC      600

GCGAACGGAT CGCGAGAGGG ATCACTACAG GGAGCGAGAC CGGGACAGGG ATCGCGATTA      660

TAGGGATCGG GATAGGGATA GACATCGGGA CCACGATAGG CACAGGGACC GACATCGCGA      720

CTCTGACCGG CACCATCGAC GATGAAGGAG CTTTTGCATT CTTCTCTTCG TCAACCACTT      780

TTGAGACTAA CATTAACCAT GCCGTTTTCT TGAAAAGCTT GTACTCATCA TGATGTTTTT      840

AAGCAAATAG GCGACAGGCG TACAGACACC TTAATATCAC ATAGAGGCAC GGCACACATA      900

CGTCTTGGAG AAGACACGTA CTTACGAATG ATGGGAGAAT TACCTACTCT GACTTGTGTA      960

AATTAGAATA TCAATGACAC TATGTATATT CAGTCGAGCT GCGAATGGTC ACACATTGTC     1020

TGATCTGCGA ATTTGTATGT GCTGCCTCTC CCTCTGACCT TCTGGTCTGG TGATACCATC     1080

CTCCCTCAGT TTGGATCATC GCCTTATTCT TCTTCCCTCT TCTGCATCTG CTTCCTGCTC     1140

GTTTGAGGAA CATCGCCAGC TGACTCTGCT TGCCTCGCAG CGATCTAGTC AAGAACAACA     1200

CNAGCTCTCA CGCTACATCA CACAAACCGT CAAAATGGGT AAGGAGGACA AGACTCACAT     1260

CAACGTGGTC GTCATCGTAC GTATTTTCCG ATCCCTCATC GGCNGTCATC TGNCCAGTCT     1320

GATTCCAAGA ATCACCGTGC TAACCATATA CCATCTANGG GTGCGTATTC CATCAATCAT     1380

CTTGAGCCAG ATCGACCGAA CATACGATAC TGACTTTGCT ACGACAGCCA CGTCGACTCC     1440

GGCAAGTCTA CCACCGTGAG TAAACACCCA TTCCACTCCA CGACCGCAAG CTCCATCTTG     1500

CGCGTGGCGT CTCTGCGATG AACATCCGAA ACTGACGTTC TGTTACAGAC TGGTCACTTG     1560

ATCTACCAGT GCGGTGGTAT CGACAAGCGT ACCATTGAGA AGTTCGAGAA GGTAAGCTTC     1620

GTTCCTTAAA TCTCCAGACG CGAGCCCAAT CTTTGCCCAT CTGCCCAGCA TCTGGCGAAC     1680

GAATGCTGTG CCGACACGAT TTTTTTTTTC ATCACCCCGC TTTCTCCTAC CCCTCCTTCG     1740

AGCGACGCAA ATTTTTTTTG CTGCCTTACG AGTTTTAGTG GGGTCGCACC TCACAACCCC     1800

ACTACTGCTC TCTGGCCGCT CCCCAGTCAC CCAACGTCAT CAACGCAGCA GTTTTCAATC     1860

AGCGATGCTA ACCATATTCC CTCGAACAGG AAGCCGCCGA ACTCGGCAAG GGTTCCTTCA     1920

AGTACGCGTG GGTTCTTGAC AAGCTCAAGG CCGAGCGTGA GCGTGGTATC ACCATCGACA     1980

TTGCCCTCTG GAAGTTCGAG ACTCCCAAGT ACTATGTCAC CGTCATTGGT ATGTTGGCAG     2040

CCATCACCTC ACTGCGTCGT TGACACATCA AACTAACAAT GCCCTCACAG ACGCTCCCGG     2100

CCACCGTGAC TTCATCAAGA ACATGATCAC TGGTACTTCC CAGGCCGACT GCGCTATCCT     2160

CATCATCGCT GCCGGTACTG GTGAGTTCGA GGCTGGTATC TCCAAGGATG CCAGACCCG      2220

TGAGCACGCT CTGCTCGCCT ACACCCTGGG TGTCAAGCAG CTCATCGTCG CCATCAACAA     2280

GATGGACACT GCCAACTGGG CCGAGGCTCG TTACCAGGAA ATCATCAAGG AGACTTCCAA     2340

CTTCATCAAG AAGGTCGGCT TCAACCCCAA GGCCGTTGCT TTCGTCCCCA TCTCCGGCTT     2400

CAACGGTGAC AACATGCTCA CCCCCTCCAC CAACTGCCCC TGGTACAAGG CTGGGAGAA      2460

GGAGACCAAG GCTGGCAAGT TCACCGGCAA GACCCTCCTT GAGGCCATCG ACTCCATCGA     2520

GCCCCCCAAG CGTCCCACGG ACAAGCCCCT GCGTCTTCCC CTCCAGGACG TCTACAAGAT     2580

CGGTGGTATC GGAACAGTTC CCGTCGGCCG TATCGAGACT GGTGTCCTCA AGCCCGGTAT     2640

GGTCGTTACC TTCGCTCCCT CCAACGTCAC CACTGAAGTC AAGTCCGTCG AGATGCACCA     2700
```

```
CGAGCAGCTC GCTGAGGGCC AGCCTGGTGA CAACGTTGGT TTCAACGTGA AGAACGTTTC        2760

CGTCAAGGAA ATCCGCCGTG GCAACGTTGC CGGTGACTCC AAGAACGACC CCCCCATGGG        2820

CGCCGCTTCT TTCACCGCCC AGGTCATCGT CATGAACCAC CCCGGCCAGG TCGGTGCCGG        2880

CTACGCCCCC GTCCTCGACT GCCACACTGC CCACATTGCC TGCAAGTTCG CCGAGCTCCT        2940

CGAGAAGATC GACCGCCGTA CCGGTAAGGC TACCGAGTCT GCCCCCAAGT TCATCAAGTC        3000

TGGTGACTCC GCCATCGTCA AGATGATCCC CTCCAAGCCC ATGTGCGTTG AGGCTTTCAC        3060

CGACTACCCT CCCCTGGGTC GTTTCGCCGT CCGTGACATG CGCCAGACCG TCGCTGTCGG        3120

TGTCATCAAG GCCGTCGAGA AGTCCTCTGC CGCCGCCGCN AAGGTCACCA AGTCCGCTGC        3180

CAAGGCCGCC AAGAAATAAG CGATACCCAT CATCAACACC TGATGTTCTG GGGTCCCTCG        3240

TGAGGTTTCT CCAGGTGGGC ACCACCATGC GCTCACTTCT ACGACGAAAC GATCAATGTT        3300

GCTATGCATG AGSACTCGAC TATGAATCGA GGCACGGTTA ATTGAGAGGC TGGGAATAAG        3360

GGTTCCATCA GAACTTCTCT GGGAATGCAA AACAAAAGGG AACAAAAAAA CTAGATAGAA        3420

GTGAATTCAT GACTTCGACA ACCAAAAAAA AAAAAAAAA A                            3461

(2) INFORMATION FOR SEQ ID NO:2:

(i) SEQUENCE CHARACTERISTICS:
        (A) LENGTH: 2336 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..700
        (D) OTHER INFORMATION: /note= "The first 700 bases of the
            nucleotide sequence are vector pSP73 sequences and
            are not part of the promoter sequence."

(xi) SEQUENCE DESCRIPTION: SEQ ID NO:2:

GCCAGTGGCG ATAAGTCGTG TCTTCCGGGT TGGACTCAAG ACGATAGTTA CCGGATAAGG          60

CGCAGCGGTC GGGCTGAACG GGGGGTTCGT GCACACAGCC CAGCTTGGAG CGAACGACCT         120

ACACCGAACT GAGATACCTA CAGCGTGAGC TATGAGAAAG CGCCACGCTT CCCGAAGGGA         180

GAAAGGCGGA CAGGTATCCG GTAAGCGGCA GGGTCGGAAC AGGAGAGAGA AAGAGGGANN         240

TTCCAGGGGG AAACGCCTGG TATCTTTATA GTCCTGTTGG GTTTCGCCAC CTCTGACTTG         300

AGCGTCGATT TTTGTGATGC TCGTCAGGGG GNGGAGCCTA TGGAAAAACG CCAGCAACGC         360

GGCCTTTTTA CGGTTCCTGG CCTTTTGCTG GCCTTTTGCT CACATGTTCT TTCCTGCGTT         420

ATCCCCTGAT TCTGTGGATA ACCGTATTAC CGCCTTTGAG TGAGCTGATA CCGCTCGCCG         480

CAGCCGAACG ACCGAGCGCA GCGAGTCAGT GAGCGAGGAA GCGGAAGAGC GCCCAATACG         540

CAAACCGCCT CTCCCCGCGC GTTGGCCGAT TCATTAATGC AGGTTAACCT GGCTTATCGA         600

AATTAATACG ACTCACTATA GGGAGACCGG CCTCGAGCAG CTGAAGCTTG CATGCCTGCA         660

GGTCGACTCT AGAGGATCCC CGGGTACCGA GCTCGAATTC GGTCTGAAGG ACGTGGAATG         720

ATGGACTTAA TGACAAGAGT TGCCTGGCTA TTGAGCTCTG GTACATGGAT CTCGAACTGA         780

GAGCGTACAA GTTACATGTA GTAAATCTAG TAGATCTCGC TGAAAGCCCT CTTTCCCGGT         840

AGAAACACCA CCAGCGTCCC GTAGGACAAG ATCCTGTCGA TCTGAGCACA TGAATTGCTT         900

CCCTGGATCT GGCGCTGCAT CTGTTTCCCC AGACAATGAT GGTAGCAGCG CATGGAAGAA         960

CCCGGTTGTT CGGAATGTCC TTGTGCTAAC AGTGGCATGA TTTTACGTTG CGGCTCATCT        1020

CGCCTTGGCA CCGGACCTCA GCAAATCTTG TCACAACAGC AATCTCAAAC AGCCTCATGG        1080
```

```
TTCCCAGATT CCCTGATTCA GAACTCTAGA GCGGCAGATG TCAAACGATT CTGACCTAGT     1140

ACCTTGAGCA TCCCTTTCGG ATCCGGCCCA TGTTCTGCCT GCCCTTCTGA GCACAGCAAA     1200

CAGCCCAAAA GGCGCCGGCC GATTCCTTTC CCGGGATGCT CCGGAGTGGC ACCACCTCCC     1260

AAAACAAGCA ACCTTGAACC CCCCCCCCAA ATCAACTGAA GCGCTCTTCG CCTAACCAGC     1320

ATAAGCCCCC CCCAGGATCG TTAGGCCAAG TGGTAGGGCC AGCCAATTAG CGAGNGGCCA     1380

TTTGGAGGTC ATGGGCGCAG AATGTCCTGA CAGTGGTATG ATATTGACTG CCCGGTGTGT     1440

GTGGCATCTG GCCATAATCG CAGGCTGAGG CGAGGAAGTC TCGTGAGGAT GTCCCGACTT     1500

TGACATCATG AGGGAGTGAG AAACTGAAGA GAAGGAAAGC TTCGAAGGTT CGATAAGGGA     1560

TGATTTGCAT GGCGGGCGAC AGGATGCGAT GGCTCGTTGG GATACATAAT GCTTGGGTTG     1620

GAAGCGATTC CAGGTCGTCT TTTTTTGGTT CATCATCACA GCATCAACAA GCAACGATAC     1680

AAGCAATCCA CTGAGGATTA CCTCTCAACT CAACCACTTT CCAAACCATC TCAACTCCCT     1740

AAGATTCTTT CAGTGTATTA TCACTAGGAT TTTTCCCAAG CCGGCTTCAA AACACACAGA     1800

TAAACCACCA ACTCTACAAC CAAAGACTTT TTGATCAATC CAACAACTTC TCTCAACATG     1860

TCTGCTGCAA CCGTCACCCG CACTGCAACC GCCGCTGTTC GCAGACCCGG CTTCTTCATG     1920

CAAGTCCGAC GGATGGGACG CTCATTGAG CACCAGCCCT TTGAGCGACT CTCCGCCACC     1980

ATGAAGCCTG CACGACCCGA CTATGCTAAG CAAGTCGTCT GGACGGCTGG CAAGTTTGTC     2040

ACTTATGTTC CTCTTTTCGG CGCCATGCTT ACCTGGCCTG CGCTCGCCAA STGGGCTCTG     2100

GACGGACACA TCGGACGGTG GTAAAAGATC AGACTCTTGT CGAGGCAACG GGGAATAGAC     2160

AGGACAGCAA AAAAGATATC TCCGGATAGA AGTGTCCATC TTTCGACTTG TATATATATA     2220

TATGCTATAC TCTGGGGGCG TTTGGATGGA CTTTGGGCAC GAAGCATACT TTGGCGCAAC     2280

GCAGATACTT TAATCTGATT CCTTTTGTTA ATTCAAAAAA AAAAAAAAAA AAAAAA         2336

(2) INFORMATION FOR SEQ ID NO:3:

(i) SEQUENCE CHARACTERISTICS:
              (A) LENGTH: 2868 base pairs
              (B) TYPE: nucleic acid
              (C) STRANDEDNESS: single
              (D) TOPOLOGY: linear (xi) SEQUENCE DESCRIPTION: SEQ ID NO:3:

TTTGTATGGC TGGATCTCGA AAGGCCCTTG TCATCGCCAA GCGTGGCTAA TATCGAATGA      60

GGGACACCCA CTTGCATATC TCCTGATCAT TCAAACGACA AGTGTGAGGT AGGCAATCCT     120

CGTATCCCAT TGCTGGGCTG AAAGCTTCAC ACGTATCGCA TAAGCGTCTC CAACCAGTGC     180

TTAGGTGACC CTTAAGGATA CTTACAGTAA GACTGTATTA AGTCAGTCAC TCTTTCACTC     240

GGGCTTTGAA TACGATCCTC AATACTCCCG ATAACAGTAA GAGGATGATA CAGCCTGCAG     300

TTGGCAAATG TAAGCGTAAT TAAACTCAGC TGAACGGCCC TTGTTGAAAG TCTCTCTCGA     360

TCAAAGCAAA GCTATCCACA GACAAGGGTT AAGCAGGCTC ACTCTTCCTA CGCCTTGGAT     420

ATGCAGCTTG GCCAGCATCG CGCATGGCCA ATGATGCACC CTTCACGGCC AACGGATCT     480

CCCGTTAAAC TCCCCTGTAA CTTGGCATCA CTCATCTGTG ATCCCAACAG ACTGAGTTGG     540

GGGCTGCGGC TGGCGGATGT CGGAGCAAAG GATCACTTCA AGAGCCCAGA TCCGGTTGGT     600

CCATTGCCAA TGGATCTAGA TTCGGCACCT TGATCTCGAT CACTGAGACA TGGTGAGTTG     660

CCCGGACGCA CCACAACTCC CCCTGTGTCA TTGAGTCCCC ATATGCGTCT TCTCAGCGTG     720

CAACTCTGAG ACGGATTAGT CCTCACGATG AAATTAACTT CCAGCTTAAG TTCGTAGCCT     780

TGAATGAGTG AAGAAATTTC AAAAACAAAC TGAGTAGAGG TCTTGAGCAG CTGGGGTGGT     840
```

```
ACGCCCCTCC TCGACTCTTG GGACATCGTA CGGCAGAGAA TCAACGGATT CACACCTTTG      900

GGTCGAGATG AGCTGATCTC GACAGATACG TGCTTCACCA CAGCTGCAGC TACCTTTGCC      960

CAACCATTGC GTTCCAGGAT CTTGATCTAC ATCACCGCAG CACCCGAGCC AGGACGGAGA     1020

GAACAATCCG GCCACAGAGC AGCACCGCCT TCCAACTCTG CTCCTGGCAA CGTCACACAA     1080

CCTGATATTA GATATCCACC TGGGTGATTG CCATTGCAGA GAGGTGGCAG TTGGTGATAC     1140

CGACTGGCCA TGCAAGACGC GGCCGGGCTA GCTGAAATGT CCCCGAGAGG ACAATTGGGA     1200

GCGTCTATGA CGGCGTGGAG ACGACGGGAA AGGACTCAGC CGTCATGTTG TGTTGCCAAT     1260

TTGAGATTGT TGACCGGGAA AGGGGGACG AAGAGGATGG CTGGGTGAGG TGGTATTGGG      1320

AGGATGCATC ATTCGACTCA GTGAGCGATG TAGAGCTCCA AGAATATAAA TATCCCTTCT     1380

CTGTCTTCTC AAAATCTCCT TCCATCTTGT CCTTCATCAG CACCAGAGCC AGCCTGAACA     1440

CCTCCAGTCA ACTTCCCTTA CCAGTACATC TGAATCAACA TCCATTCTTT GAAATCTCAC     1500

CACAACCACC ATCTTCTTCA AAATGAAGTT CTTCGCCATC GCCGCTCTCT TTGCCGCCGC     1560

TGCCGTTGCC CAGCCTCTCG AGGACCGCAG CAACGGCAAC GGCAATGTTT GCCCTCCCGG     1620

CCTCTTCAGC AACCCCCAGT GCTGTGCCAC CCAAGTCCTT GGCCTCATCG GCCTTGACTG     1680

CAAAGTCCGT AAGTTGAGCC ATAACATAAG AATCCTCTTG ACGGAAATAT GCCTTCTCAC     1740

TCCTTTACCC CTGAACAGCC TCCCAGAACG TTTACGACGG CACCGACTTC CGCAACGTCT     1800

GCGCCAAAAC CGGCGCCCAG CCTCTCTGCT GCGTGGCCCC CGTTGTAAGT TGATGCCCCA     1860

GCTCAAGCTC CAGTCTTTGG CAAACCCATT CTGACACCCA GACTGCAGGC CGGCCAGGCT     1920

CTTCTGTGCC AGACCGCCGT CGGTGCTTGA GATGCCCGCC CGGGGTCAAG GTGTGCCCGT     1980

GAGAAAGCCC ACAAAGTGTT GATGAGGACC ATTTCCGGTA CTGGGAAAGT TGGCTCCACG     2040

TGTTTGGGCA GGTTTGGGCA AGTTGTGTAG ATATTCCATT CGTACGCCAT TCTTATTCTC     2100

CAATATTTCA GTACACTTTT CTTCATAAAT CAAAAAGACT GCTATTCTCT TTGTGACATG     2160

CCGGAAGGGA ACAATTGCTC TTGGTCTCTG TTATTTGCAA GTAGGAGTGG GAGATTCGCC     2220

TTAGAGAAAG TAGAGAAGCT GTGCTTGACC GTGGTGTGAC TCGACGAGGA TGGACTGAGA     2280

GTGTTAGGAT TAGGTCGAAC GTTGAAGTGT ATACAGGATC GTCTGGCAAC CCACGGATCC     2340

TATGACTTGA TGCAATGGTG AAGATGAATG ACAGTGTAAG AGGAAAAGGA AATGTCCGCC     2400

TTCAGCTGAT ATCCACGCCA ATGATACAGC GATATACCTC CAATATCTGT GGGAACGAGA     2460

CATGACATAT TTGTGGGAAC AACTTCAAAC AGCGAGCCAA GACCTCAATA TGCACATCCA     2520

AAGCCAAACA TTGGCAAGAC GAGAGACAGT CACATTGTCG TCGAAAGATG GCATCGTACC     2580

CAAATCATCA GCTCTCATTA TCGCCTAAAC CACAGATTGT TTGCCGTCCC CCAACTCCAA     2640

AACGTTACTA CAAAAGACAT GGGCGAATGC AAAGACCTGA AGCAAACCC TTTTTGCGAC      2700

TCAATTCCCT CCTTTGTCCT CGGAATGATG ATCCTTCACC AAGTAAAAGA AAAGAAGAT      2760

TGAGATAATA CATGAAAAGC ACAACGGAAA CGAAAGAACC AGGAAAAGAA TAAATCTATC     2820

ACGCACCTTG TCCCCACACT AAAAGCAACA GGGGGGGTAA AATGAAAT                  2868
```

(2) INFORMATION FOR SEQ ID NO:4:

(i) SEQUENCE CHARACTERISTICS:
        (A) LENGTH: 2175 base pairs
        (B) TYPE: nucleic acid
        (C) STRANDEDNESS: single
        (D) TOPOLOGY: linear (xi) SEQUENCE DESCRIPTION: SEQ ID NO:4:

```
AAAAAGCTAG AACGAGACGA TTCCGGCCCG GCAAACCAGG CCGAGTGACG GGAGCATTTC    60

CATGATTTCA CTCGGCAAAC TCTGGCTACA ATTTTCAGGC GGCGAGTTCC GATACAAGGG   120

AAATCTATTA CCCACAGACG AACGGGAATC GGTGATGAGT GGTTTCTTGT AAGTCAACAT   180

TGAGCTAGAT AATTCCGGGC GAGATCAAGA TGCCATACTT TGATTGATGA AAAATCAATG   240

TCAGGCGTAA GTCTCTTCAA GCTCGCCCAG TCCTCTGTAT GTAACAGCAA TCGCAATTCC   300

GAAATGTGCC GAGCCAATGG AACATGCGTG TCTTTCTCTT TTCACACACA TCCAGTTCGA   360

GAGTCTTCTC TTCATCGTTT CATCGAATCC CTTCCCCTCC AGCTATTCAC CCAGCCGAGC   420

CCTTCAGCGC ACCAGCGTAT GTATGTACCC TCGGCTAAGA CGCAACAGAA GCATCATCAA   480

TATACCTGAT GTACTACTAT CTACTATGAA GCCCAAAAAC CCCTTCGCAG CCCAAATGTA   540

ACCCAAGCAA CGAATCCCCA ATAAGAGACA ATCCTCAGTG ACCCCAGAA GAGCACAGAA   600

TCGAGCTGGT CCTGGTGGGT CGCATTGAGA CCGGTGGAGA TGCGTTCGAT TCGACTGCCG   660

GAGCTCCCGG GAAGCCGGCA GATGGTCCCA TGCGATGCCC TGCACCGTTT TTGTGAATCG   720

TCGGCATCGC GAGAAGTGGC CTGCTATGAC GTCGCTTGCA GCTTGGCCGC TCTGTTCGAA   780

GTTTTTCGAT GTTTTTCTTC ATGCGGGAGA AAGAAAACAT CAGATGACAT GATTATCCGA   840

ATGGATGGCG GGAGTTATCG TGGTGACGGC TGCTTCATGA GATGAGTATA AATGAGCTTG   900

TTCGCTCAGC GTGTCATGGA TCTTGTCCAG CTCCAAAGCA TCGGCTTCAG CATCCATCCG   960

CTTGAACAGA CAGGCACCAG CTTGAATCAG AAGCATACCC TTGATTTGAT ACTCTCTTGG  1020

GAAAAAACAC CACCATCTGT GTAATACTTT GATACCCCCA AAGCTCAAAC GACCGCTTGT  1080

ACATACAATA ACACCGCCAC AATGTTCGCC AACTTGACGC ACGCTACCCT GCGATTCATC  1140

GCCTTCTTCA ACCACCTGAT GATCCTGGCC TCATCAGCCA TCGTCACCGG CCTCGTATCC  1200

TGGTTCCTCG ACAAGTACGA CTACCGCGGC GTGAACATTG TCTACCAGGA AGTCATCGTA  1260

TGTCCTCCCA AGCACCACAT CAAACACACC CCATACCTTG GCTCTCCTCA GCTCCGTCGA  1320

AGCACATAAT ACTAACGCAT GCAACAACTA GGCCACCATA ACTCTGGGCT TCTGGCTCGT  1380

TGGTGCCGTC TTGCCCCTCG TTGGCAGATA CCGCGGCCAC CTGGCCCCTC TCAACCTCAT  1440

CTTCTCCTAC CTCTGGCTCA CCTCTTTCAT CTTCTCCGCG CAGGACTGGA GCAGCGACAA  1500

GTGCAGCTTC GGCCAGCCTG GCGAGGGCCA CTGCAGCCGC AAGAAGGCCA TTGAATCCTT  1560

CAACTTTATC GCATTGTAAG TGCCTACAAG TAATTTGCTA TGTATATGGG AGAGAGAGAG  1620

AAGAAGAAGA ATATGGCTCT AACATGGCAT CTCTACAGCT TCTTCCTCCT CTGCAACACC  1680

CTGGTTGAGA TGCTCCTGCT CCGCGCCGAG TATGCTACCC CCGTTGCTGC TGCTCACAAC  1740

AAGGAGATTT CTGCCGGCCG CCCCTCTGAC AACTCTGTCT AAATAACAAT AGACATGCAT  1800

AGATGAACGG AGACCACTTC TACTTTCTTT GCGAGTTCCT GATCCGTTGA CCTGCAGGTC  1860

GACBBBBBCC GCGCTCGCAT GGTTCATCTG CTACAACAAC ACAATGACAA TCCGAACCAG  1920

TCAATAAACC TCGACAACAC GACGAGTACT TTTGCGGATA GAAAGATACC CATTACACAG  1980

GAGATCAAAT GGGGAAATTG GAAGTGTATG GATGGACGCC CGTGTATAAT GAGGTTGTGA  2040

ACGGGATGGG AGGCAATGAA TAATGGATAA TGAGGTAATG GATAGATTCG GTCGTTTTGA  2100

TACCACAGCT GCACTCTGCT CTACGTCTGT CATTAATGAT ACATACAAAT GATACCTTAT  2160

ACGCTAAAAA AAAAA                                                   2175
```

(2) INFORMATION FOR SEQ ID NO:5:

(i) SEQUENCE CHARACTERISTICS:
        (A) LENGTH: 2737 base pairs
        (B) TYPE: nucleic acid (C) STRANDEDNESS: single
(D) TOPOLOGY: linear (xi) SEQUENCE DESCRIPTION: SEQ ID NO:5:

```
TCTAGAATCT CTTCGAGATG GCCGAGAAAG GCTTGTTTTT CTCTCCTTCT TCAAACTGGC          60

CACTGTTTGT TTTCAAACTT GGGGTTTCGT GGGGCTTTTG GGGGCATGTC TGCCAGGTCT         120

CCCGTAGGCT GGACAGCCAA AGCCTCACTA CAAACAGGCA GTTGTCAATA GATTGATGTC         180

TGAGATGGAT GGTTTTATGT TTGGGGGAGG TCATGTATGT ATTTATCTAT ATTTGCAAAG         240

ATGATCCATG AGTCAGACTT GCACAGGTTT CTCGTGCGCT GGATAAATCT TGTTGGAGTG         300

CGGGTGAGGT GGTGGATGGC ATTCAACCCA CAGCAACACT TGCCCAGGGG GATGTACTGC         360

AGCGATTTGT TTCCCTTCGA GTATTAGATG ATGATGCCGA ACAGACAAAT TTGAGCCTCG         420

CTGCTCTCGG ATGTCGGGTT TCTCTTGTGT GCCGGTGATG TGTGATGGCC TGGCCCGCAA         480

AGAGAGCGAA AAACATGCTC AAAATGTAGC ACACGGCGAC TTCTCGGACA CTTGCGTACC         540

TTGAGAGACA AGCAGACTAC AGGGATGACG AGTAATACGA CAGAGCGATA CGACACAGCT         600

ATACGACACA GCTAAGAAAA TAAAGGTATT AGTACTACTA ATTGATTACC TACTACCTAG         660

ATATATACTA TACCTTATAT TTTATATGTG TGTGTGTGTG TATGTATATG CCTTACCTTA         720

TGCTTCGCAA AGAAGAGAAA CTAAAACGCC TCCTGGCTAC CTACCTACCT CTACCTTGTA         780

AGAGATGGAA TAATGTGGCC GCGCGTAAAG TAGGTACTGG ATATACAGGT CCTGAACATG         840

GCCCTGAATC CTGCCAGGCA GCCACCTCAC CCCTTCCGCA GGTATTTATG TAGCCCACAG         900

CTCCTCCAGA GACGATGCCG AGATGCCTCA TGCAGTCTAC CTACAAAGCC AGCAGTTTCA         960

CGCTTGACTC TCACTCTTGA TTGAATTCCC TCCCTCCCAT AATACCAATT GGCGTTCAAC        1020

GATTGCCAGC AGAATGGCCG CCCAACACGA CGTCGAGGCC ATGGCAAAGT CCATGTCCGA        1080

CTTTTTCAAG GACACGGCCC AAAAGCAGGA CTCGACCAAG CATGACTTTG TCCAAGCCTC        1140

GCACGGCATC ATGAGGGCCA TTGTCGAGCC GCTCGTCACC CAGATGGGCT TCCGCGAGAC        1200

CCTCACCGAG CCCGTCGTCT TGCTCGACAG CGCGTGCGGA GCGGGCGTGC TGACGCAGGA        1260

GGTGCAGGCG GCGCTGCCAA AGGAGCTTCT GGAGAGGAGC TCGTTTACGT GTGCGGACAA        1320

TGCCGAGGGC TTGGTGGACG TGGTGAAGAG GAGGATTGAT GAGGAGAAGT GGGTGAATGC        1380

AGAGGCCAAG GTCCTTGATG CCCTGGTGAG TATATACATA TATATCTATA TCTATATAGA        1440

TATATATATG CCTTTGACTC CCCCCTTTAC ATGTCCTACG GCTGCTGATT GATTGATTGA        1500

TGTGGTGATG GTGATGTCCC AGAACACGGG GCTCCCAGAC AACTCCTTCA CCCATGTGGG        1560

CATTGCCCTG GCACTGCACA TCATCCCCGA TCCAGATGCC GTCGTCAAAG GTAAACAATC        1620

ACCAGCGTCA CTGCAAAGAG AGATTACGGG ATATCATATA CTGAAACCAA AGCCCAGACT        1680

GCATCAGAAT GCTCAAGCCA GGCGGCATCT TTGGCGCATC GACATGGCCC AAGGCCAGCG        1740

CCGACATGTT CTGGATCGCC GACATGCGCA CCGCCCTGCA GTCGCTCCCC TTTGACGCGC        1800

CGCTGCCAGA CCCGTTCCCC ATGCAGCTGC ACACCTCGGG CCACTGGGAC GACGCCGCCT        1860

GGGTCGAGAA GCATCTCGTC GAGGATCTGG GGCTGGCCAA CGTCTGTGTG AGGGAGCCGG        1920

CGGGCGAGTA CAGCTTTGCG AGCGCGGACG AGTTCATGGC GACGTTTCAG ATGATGCTGC        1980

CGTGGATTAT GAAGACGTTT TGGAGCGAGG AGGTGAGGGA GAAGCATTCG GTCGACGAGG        2040

TCAAGGAGTT GGTGAAGAGG CATCTGGAGG ACAAGTATGG GGGGAAGGGA TGGACCATTA        2100

AGTGGCGGGT GATTACCATG ACTGCGACTG CGAGCAAGTG AGGGAGGGCA TCTGCTCATG        2160

ATTATGTGAC AGCGAGCCAG TAGAGAGCCA TATTGTTGTC TTCAGAATGT GAGGACCGTG        2220

ATGGTTGGTG TTTGTTGGAG TGATAACTCG TGGGTGTTGC TATTTGCATG TGAGACGATG        2280
```

```
AACCATGCGC ACCAGCCACA ATCACTGTCC CCCACCTTAC CTACCAACTT CAAGTTACCA      2340

CCTTACCTTT ACCTGATCTA GCACTGTGGC GCAGCTTGGT TTGACTGCTA GGTACCTACC      2400

TAGTAGTAAT CAGGTACATT CTTCATCCCT GTGTCCTGGT GTCGCAGTTG CAGCTTGTCT      2460

TATCGCTGTG GCCACGCATC GAGTGGCAGC ATCTTCAACT TCAAGTCCCG TCGGTCGCAC      2520

TCTGGCCACG TCGCAGATGG ATCGCAGCGG GATCTGAACC GCTCGCTCGG CAACTGATAC      2580

CAAGTCAACA AACACACGAG ACGACGGGAC GCTGATATAA NNNNGAGGAG GGTAAGAGAA      2640

CTCTACGAGG GGCGGAAACT TGGTCCGACA ATTTCCCTCC CATCTTCACC CTCGACTCGA      2700

ACTCGAACTC GATAGCCGCA CCCTCGACCG ATTGCCC                               2737

(2) INFORMATION FOR SEQ ID NO:6:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:6:

ACCGGAATTC ATATCTAGAG GAGCCCGCGA GTTTGGATAC GCC                        43

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:7:

ACCGCCGCGG TTTGACGGTT TGTGTGATGT AGCG                                  34

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:8:

TCTTCAAGAA TTGCTCGACC AATTCTCACG GTGAATGTAG G                          41

(2) INFORMATION FOR SEQ ID NO:9:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:9:

ACACATCTAG AGGTGACCTA GGCATTCTGG CCACTAGATA TATATTTAGA AGGTTCTTGT      60

AGCTCAAAAG AGC                                                         73

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear
```

(xi) SEQUENCE DESCRIPTION: SEQ ID NO:10:

GGGAATTCTC TAGAAACGCG TTGGCAAATT ACGGTACG                                38

(2) INFORMATION FOR SEQ ID NO:11:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:11:

GGGAATTCGG TCACCTCTAA ATGTGTAATT TGCCTGCTTG ACC                          43

(2) INFORMATION FOR SEQ ID NO:12:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:12:

GGGAATTCGG TCACCTCTAA ATGTGTAATT TGCCTGCTTG ACCGATCTAA ACTGTTCGAA        60

GCCCGAATGT AGG                                                          73

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:13:

GGGAATTCTT CTAGATTGCA GAAGCACGGC AAAGCCCACT TACCC                        45

(2) INFORMATION FOR SEQ ID NO:14:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:14:

TAGCGAATTC TAGGTCACCT CTAAAGGTAC CCTGCAGCTC GAGCTAG                      47

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:15:

GGGAATTCAT GATGCGCAGT CCGCGG                                             26

(2) INFORMATION FOR SEQ ID NO:16:

(i) SEQUENCE CHARACTERISTICS:
        (A) LENGTH: 1588 base pairs
        (B) TYPE: nucleic acid
        (C) STRANDEDNESS: single
        (D) TOPOLOGY: linear (xi) SEQUENCE DESCRIPTION: SEQ ID NO:16:

```
CCCCCCTATC TTAGTCCTTC TTGTTGTCCC AAAATGGCGC CCTCAGTTAC ACTGCCGTTG        60

ACCACGGCCA TCCTGGCCAT TGCCCGGCTC GTCGCCGCCC AGCAACCGGG TACCAGCACC       120

CCCGAGGTCC ATCCCAAGTT GACAACCTAC AAGTGTACAA AGTCCGGGGG GTGCGTGGCC       180

CAGGACACCT CGGTGGTCCT TGACTGGAAC TACCGCTGGA TGCACGACGC AAACTACAAC       240

TCGTGCACCG TCAACGGCGG CGTCAACACC ACGCTCTGCC CTGACGAGGC GACCTGTGGC       300

AAGAACTGCT TCATCGAGGG CGTCGACTAC GCCGCCTCGG GCGTCACGAC CTCGGGCAGC       360

AGCCTCACCA TGAACCAGTA CATGCCCAGC AGCTCTGGCG GCTACAGCAG CGTCTCTCCT       420

CGGCTGTATC TCCTGGACTC TGACGGTGAG TACGTGATGC TGAAGCTCAA CGGCCAGGAG       480

CTGAGCTTCG ACGTCGACCT CTCTGCTCTG CCGTGTGGAG AGAACGGCTC GCTCTACCTG       540

TCTCAGATGG ACGAGAACGG GGGCGCCAAC CAGTATAACA CGGCCGGTGC CAACTACGGG       600

AGCGGCTACT GCGATGCTCA GTGCCCCGTC CAGACATGGA GGAACGGCAC CCTCAACACT       660

AGCCACCAGG GCTTCTGCTG CAACGAGATG GATATCCTGG AGGGCAACTC GAGGGCGAAT       720

GCCTTGACCC CTCACTCTTG CACGGCCACG GCCTGCGACT CTGCCGGTTG CGGCTTCAAC       780

CCCTATGGCA GCGGCTACAA AGCTACTAC GGCCCCGGAG ATACCGTTGA CACCTCCAAG        840

ACCTTCACCA TCATCACCCA GTTCAACACG GACAACGGCT CGCCCTCGGG CAACCTTGTG       900

AGCATCACCC GCAAGTACCA GCAAAACGGC GTCGACATCC CCAGCGCCCA GCCCGGCGGC       960

GACACCATCT CGTCCTGCCC GTCCGCCTCA GCCTACGGCG GCCTCGCCAC CATGGGCAAG      1020

GCCCTGAGCA GCGGCATGGT GCTCGTGTTC AGCATTTGGA ACGACAACAG CCAGTACATG      1080

AACTGGCTCG ACAGCGGCAA CGCCGGCCCC TGCAGCAGCA CCGAGGGCAA CCCATCCAAC      1140

ATCCTGGCCA ACAACCCCAA CACGCACGTC GTCTTCTCCA ACATCCGCTG GGGAGACATT      1200

GGGTCTACTA CGAACTCGAC TGCGCCCCCG CCCCCGCCTG CGTCCAGCAC GACGTTTTCG      1260

ACTACACGGA GGAGCTCGAC GACTTCGAGC AGCCCGAGCT GCACGCAGAC TCACTGGGGG      1320

CAGTGCGGTG GCATTGGGTA CAGCGGGTGC AAGACGTGCA CGTCGGGCAC TACGTGCCAG      1380

TATAGCAACG ACTACTACTC GCAATGCCTT TAGAGCGTTG ACTTGCCTCT GGTCTGTCCA      1440

GACGGGGGCA CGATAGAATG CGGGCACGCA GGGAGCTCGT AGACATTGGG CTTAATATAT      1500

AAGACATGCT ATGTTGTATC TACATTAGCA AATGACAAAC AAATGAAAAA GAACTTATCA      1560

AGCAAAAAAA AAAAAAAAAA AAAAAAA                                          1588
```

(2) INFORMATION FOR SEQ ID NO:17:

(i) SEQUENCE CHARACTERISTICS:
        (A) LENGTH: 1820 base pairs
        (B) TYPE: nucleic acid
        (C) STRANDEDNESS: single
        (D) TOPOLOGY: linear (xi) SEQUENCE DESCRIPTION: SEQ ID NO:17:

```
CCGCGGACTG CGCATCATGT ATCGGAAGTT GGCCGTCATC TCGGCCTTCT TGGCCACAGC        60

TCGTGCTCAG TCGGCCTGCA CTCTCCAATC GGAGACTCAC CCGCCTCTGA CATGGCAGAA       120

ATGCTCGTCT GGTGGCACTT GCACTCAACA GACAGGCTCC GTGGTCATCG ACGCCAACTG       180

GCGCTGGACT CACGCTACGA ACAGCAGCAC GAACTGCTAC GATGGCAACA CTTGGAGCTC       240

GACCCTATGT CCTGACAACG AGACCTGCGC GAAGAACTGC TGTCTGGACG GTGCCGCCTA       300

CGCGTCCACG TACGGAGTTA CCACGAGCGG TAACAGCCTC TCCATTGGCT TGTCACCCA        360

GTCTGCGCAG AAGAACGTTG GCGCTCGCCT TTACCTTATG GGCAGCGACA CGACCTACCA       420
```

```
GGAATTCACC CTGCTTGGCA ACGAGTTCTC TTTCGATGTT GATGTTTCGC AGCTGCCGTA      480

AGTGACTTAC CATGAACCCC TGACGTATCT TCTTGTGGGC TCCCAGCTGA CTGGCCAATT      540

TAAGGTGCGG CTTAACGGA GCTCTCTACT TCGTGTCCAT GGACGCGGAT GGTGGCGTGA       600

GCAAGTATCC CACCAACACC GCTGGCGCCA AGTACGGCAC GGGGTACTGT GACAGCCAGT      660

GTCCCCGCGA TCTGAAGTTC ATCAATGGCC AGGCCAACGT TGAGGGCTGG GAGCCGTCAT      720

CCAACAACGC AAACACGGGC ATTGGAGGAC ACGGAAGCTG CTGCTCTGAG ATGGATATCT      780

GGGAGGCCAA CTCCATCTCC GAGGCTCTTA CCCCCCACCC TTGCACGACT GTCGGCCAGG      840

AGATCTGCGA GGGTGATGGG TGCGGCGGAA CTTACTCCGA TAACAGATAT GGCGGCACTT      900

GCGATCCCGA TGGCTGCGAC TGGAACCCAT ACCGCCTGGG CAACACCAGC TTCTACGGCC      960

CTGGCTCAAG CTTTACCCTC GATACCACCA AGAAATTGAC CGTTGTCACC CAGTCCGAGA     1020

CGTCGGGTGC CATCAACCGA TACTATGTCC AGAATGGCGT CACTTTCCAG CAGCCCAACG     1080

CCGAGCTTGG TAGTTACTCT GGCAACGAGC TCAACGATGA TTACTGCACA GCTGAGGAGG     1140

CAGAATTCGG CGGATCCTCT TTCTCAGACA AGGGCGGCCT GACTCAGTTC AAGAAGGCTA     1200

CCTCTGGCGG CATGGTTCTG GTCATGAGTC TGTGGGATGA TGTGAGTTTG ATGGACAAAC     1260

ATGCGCGTTG ACAAAGAGTC AAGCAGCTGA CTGAGATGTT ACAGTACTAC GCCAACATGC     1320

TGTGGCTGGA CTCCACCTAC CCGACAAACG AGACCTCCTC CACACCCGGT GCCGTGCGCG     1380

GAAGCTGCTC CACCAGCTCC GGTGTCCCTG CTCAGGTCGA ATCTCAGTCT CCCAACGCCA     1440

AGGTCACCTT CTCCAACATC AAGTTCGGAC CCATTGGCAG CACCGGCAAC CCTAGCGGCG     1500

GCAACCCTCC CGGCGGAAAC CCGCCTGGCA CCACCACCAC CCGCCGCCCA GCCACTACCA     1560

CTGGAAGCTC TCCCGGACCT ACCCAGTCTC ACTACGGCCA GTGCGGCGGT ATTGGCTACA     1620

GCGGCCCCAC GGTCTGCGCC AGCGGCACAA CTTGCCAGGT CCTGAACCCT TACTACTCTC     1680

AGTGCCTGTA AAGCTCCGTG CGAAAGCCTG ACGCACCGGT AGATTCTTGG TGAGCCCGTA     1740

TCATGACGGC GGCGGGAGCT ACATGGCCCC GGGTGATTTA TTTTTTTTGT ATCTACTTCT     1800

GACCCTTTTC AAATATACGG                                                1820
```

(2) INFORMATION FOR SEQ ID NO:18:

(i) SEQUENCE CHARACTERISTICS:
        (A) LENGTH: 2218 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:18:

```
GAATTCTCAC GGTGAATGTA GGCCTTTTGT AGGGTAGGAA TTGTCACTCA AGCACCCCCA       60

ACCTCCATTA CGCCTCCCCC ATAGAGTTCC CAATCAGTGA GTCATGGCAC TGTTCTCAAA      120

TAGATTGGGG AGAAGTTGAC TTCCGCCCAG AGCTGAAGGT CGCACAACCG CATGATATAG      180

GGTCGGCAAC GGCAAAAAAG CACGTGGCTC ACCGAAAAGC AAGATGTTTG CGATCTAACA      240

TCCAGGAACC TGGATACATC CATCATCACG CACGACCACT TGATCTGCT GGTAAACTCG       300

TATTCGCCCT AAACCGAAGT GCGTGGTAAA TCTACACGTG GGCCCCTTTC GGTATACTGC      360

GTGTGTCTTC TCTAGGTGGC ATTCTTTTCC CTTCCTCTAG TGTTGAATTG TTTGTGTTGG      420

AGTCCGAGCT GTAACTACCT CTGAATCTCT GGAGAATGGT GGACTAACGA CTACCGTGCA      480

CCTGCATCAT GTATATAATA GTGATCCTGA GAAGGGGGGT TTGGAGCAAT GTGGGACTTT      540
```

```
GATGGTCATC AAACAAAGAA CGAAGACGCC TCTTTTGCAA AGTTTTGTTT CGGCTACGGT      600

GAAGAACTGG ATACTTGTTG TGTCTTCTGT GTATTTTTGT GGCAACAAGA GGCCAGAGAC      660

AATCTATTCA ACACCAAGC TTGCTCTTTT GAGCTACAAG AACCTGTGGG GTATATATCT       720

AGAGTTGTGA AGTCGGTAAT CCCGCTGTAT AGTAATACGA GTCGCATCTA AATACTCCGA      780

AGCTGCTGCG AACCCGGAGA ATCGAGATGT GCTGGAAAGC TTCTAGCGAG CGGCTAAATT      840

AGCATGAAAG GCTATGAGAA ATTCTGGAGA CGGCTTGTTG AATCATGGCG TTCCATTCTT     900

CGACAAGCAA AGCGTTCCGT CGCAGTAGCA GGCACTCATT CCCGAAAAAA CTCGGAGATT      960

CCTAAGTAGC GATGGAACCG GAATAATATA ATAGGCAATA CATTGAGTTG CCTCGACGGT     1020

TGCAATGCAG GGGTACTGAG CTTGGACATA ACTGTTCCGT ACCCCACCTC TTCTCAACCT     1080

TTGGCGTTTC CCTGATTCAG CGTACCCGTA CAAGTCGTAA TCACTATTAA CCCAGACTGA     1140

CCGGACGTGT TTTGCCCTTC ATTTGGAGAA ATAATGTCAT TGCGATGTGT AATTTGCCTG     1200

CTTGACCGAC TGGGGCTGTT CGAAGCCCGA ATGTAGGATT GTTATCCGAA CTCTGCTCGT     1260

AGAGGCATGT TGTGAATCTG TGTCGGGCAG GACACGCCTC GAAGGTTCAC GGCAAGGGAA     1320

ACCACCGATA GCAGTGTCTA GTAGCAACCT GTAAAGCCGC AATGCAGCAT CACTGGAAAA     1380

TACAAACCAA TGGCTAAAAG TACATAAGTT AATGCCTAAA GAAGTCATAT ACCAGCGGCT     1440

AATAATTGTA CAATCAAGTG GCTAAACGTA CCGTAATTTG CCAACGGCTT GTGGGGTTGC     1500

AGAAGCAACG GCAAAGCCCC ACTTCCCCAC GTTTGTTTCT TCACTCAGTC CAATCTCAGC     1560

TGGTGATCCC CCAATTGGGT CGCTTGTTTG TTCCGGTGAA GTGAAAGAAG ACAGAGGTAA     1620

GAATGTCTGA CTCGGAGCGT TTTGCATACA ACCAAGGGCA GTGATGGAAG ACAGTGAAAT     1680

GTTGACATTC AAGGAGTATT TAGCCAGGGA TGCTTGAGTG TATCGTGTAA GGAGGTTTGT     1740

CTGCCGATAC GACGAATACT GTATAGTCAC TTCTGATGAA GTGGTCCATA TTGAAATGTA     1800

AGTCGGCACT GAACAGGCAA AAGATTGAGT TGAAACTGCC TAAGATCTCG GGCCCTCGGG     1860

CCTTCGGCCT TTGGGTGTAC ATGTTTGTGC TCCGGGCAAA TGCAAAGTGT GGTAGGATCG     1920

AACACACTGC TGCCTTTACC AAGCAGCTGA GGGTATGTGA TAGGCAAATG TTCAGGGGCC     1980

ACTGCATGGT TTCGAATAGA AAGAGAAGCT TAGCCAAGAA CAATAGCCGA TAAAGATAGC     2040

CTCATTAAAC GGAATGAGCT AGTAGGCAAA GTCAGCGAAT GTGTATATAT AAAGGTTCGA     2100

GGTCCGTGCC TCCCTCATGC TCTCCCCATC TACTCATCAA CTCAGATCCT CCAGGAGACT     2160

TGTACACCAT CTTTTGAGGC ACAGAAACCC AATAGTCAAC CGCGGACTGC GCATCATG       2218

(2) INFORMATION FOR SEQ ID NO:19:

(i) SEQUENCE CHARACTERISTICS:
        (A) LENGTH: 1142 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:19:

GAATTCTCAC GGTGAATGTA GGCCTTTTGT AGGGTAGGAA TTGTCACTCA AGCACCCCCA       60

ACCTCCATTA CGCCTCCCCC ATAGAGTTCC CAATCAGTGA GTCATGGCAC TGTTCTCAAA      120

TAGATTGGGG AGAAGTTGAC TTCCGCCCAG AGCTGAAGGT CGCACAACCG CATGATATAG      180

GGTCGGCAAC GGCAAAAAAG CACGTGGCTC ACCGAAAAGC AAGATGTTTG CGATCTAACA      240

TCCAGGAACC TGGATACATC CATCATCACG CACGACCACT TTGATCTGCT GGTAAACTCG      300

TATTCGCCCT AAACCGAAGT GCGTGGTAAA TCTACACGTG GGCCCCTTTC GGTATACTGC      360
```

```
GTGTGTCTTC TCTAGGTGGC ATTCTTTTCC CTTCCTCTAG TGTTGAATTG TTTGTGTTGG      420

AGTCCGAGCT GTAACTACCT CTGAATCTCT GGAGAATGGT GGACTAACGA CTACCGTGCA      480

CCTGCATCAT GTATATAATA GTGATCCTGA AAGGGGGGT TTGGAGCAAT GTGGGACTTT       540

GATGGTCATC AAACAAAGAA CGAAGACGCC TCTTTTGCAA AGTTTTGTTT CGGCTACGGT      600

GAAGAACTGG ATACTTGTTG TGTCTTCTGT GTATTTTTGT GGCAACAAGA GGCCAGAGAC      660

AATCTATTCA ACACCAAGC TTGCTCTTTT GAGCTACAAG AACCTGTGGG GTATATATCT       720

AGTGGCCAGA ATGCCTAGGT CACCTCTAGA GAGTTGAAAC TGCCTAAGAT CTCGGGCCCT     780

CGGGCCTTCG GCCTTTGGGT GTACATGTTT GTGCTCCGGG CAAATGCAAA GTGTGGTAGG     840

ATCGAACACA CTGCTGCCTT TACCAAGCAG CTGAGGGTAT GTGATAGGCA AATGTTCAGG     900

GGCCACTGCA TGGTTTCGAA TAGAAAGAGA AGCTTAGCCA AGAACAATAG CCGATAAAGA    960

TAGCCTCATT AAACGGAATG AGCTAGTAGG CAAAGTCAGC GAATGTGTAT ATATAAAGGT    1020

TCGAGGTCCG TGCCTCCCTC ATGCTCTCCC CATCTACTCA TCAACTCAGA TCCTCCAGGA   1080

GACTTGTACA CCATCTTTTG AGGCACAGAA ACCCAATAGT CAACCGCGGA CTGCGCATCA   1140

TG                                                                                                                     1142

(2) INFORMATION FOR SEQ ID NO:20:

(i) SEQUENCE CHARACTERISTICS:
        (A) LENGTH: 2266 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:20:

GAATTCTCAC GGTGAATGTA GGCCTTTTGT AGGGTAGGAA TTGTCACTCA AGCACCCCCA        60

ACCTCCATTA CGCCTCCCCC ATAGAGTTCC CAATCAGTGA GTCATGGCAC TGTTCTCAAA      120

TAGATTGGGG AGAAGTTGAC TTCCGCCCAG AGCTGAAGGT CGCACAACCG CATGATATAG      180

GGTCGGCAAC GGCAAAAAAG CACGTGGCTC ACCGAAAAGC AAGATGTTTG CGATCTAACA      240

TCCAGGAACC TGGATACATC CATCATCACG CACGACCACT TTGATCTGCT GGTAAACTCG      300

TATTCGCCCT AAACCGAAGT GCGTGGTAAA TCTACACGTG GGCCCCTTTC GGTATACTGC      360

GTGTGTCTTC TCTAGGTGGC ATTCTTTTCC CTTCCTCTAG TGTTGAATTG TTTGTGTTGG      420

AGTCCGAGCT GTAACTACCT CTGAATCTCT GGAGAATGGT GGACTAACGA CTACCGTGCA      480

CCTGCATCAT GTATATAATA GTGATCCTGA AAGGGGGG TTTGGAGCAAT GTGGGACTTT      540

GATGGTCATC AAACAAAGAA CGAAGACGCC TCTTTTGCAA AGTTTTGTTT CGGCTACGGT      600

GAAGAACTGG ATACTTGTTG TGTCTTCTGT GTATTTTTGT GGCAACAAGA GGCCAGAGAC      660

AATCTATTCA ACACCAAGC TTGCTCTTTT GAGCTACAAG AACCTGTGGG GTATATATCT       720

AGTGGCCAGA ATGCCTAGGT CACCTCTAAA GGTACCCTGC AGCTCGAGCT AGAGTTGTGA     780

AGTCGGTAAT CCCGCTGTAT AGTAATACGA GTCGCATCTA AATACTCCGA AGCTGCTGCG     840

AACCCGGAGA ATCGAGATGT GCTGGAAAGC TTCTAGCGAG CGGCTAAATT AGCATGAAAG     900

GCTATGAGAA ATTCTGGAGA CGGCTTGTTG AATCATGGCG TTCCATTCTT CGACAAGCAA     960

AGCGTTCCGT CGCAGTAGCA GGCACTCATT CCCGAAAAAA CTCGGAGATT CCTAAGTAGC    1020

GATGGAACCG GAATAATATA ATAGGCAATA CATTGAGTTG CCTCGACGGT TGCAATGCAG   1080

GGGTACTGAG CTTGGACATA ACTGTTCCGT ACCCCACCTC TTCTCAACCT TTGGCGTTTC    1140
```

```
CCTGATTCAG CGTACCCGTA CAAGTCGTAA TCACTATTAA CCCAGACTGA CCGGACGTGT    1200

TTTGCCCTTC ATTTGGAGAA ATAATGTCAT TGCGATGTGT AATTTGCCTG CTTGACCGAC    1260

TGGGGCTGTT CGAAGCCCGA ATGTAGGATT GTTATCCGAA CTCTGCTCGT AGAGGCATGT    1320

TGTGAATCTG TGTCGGGCAG GACACGCCTC GAAGGTTCAC GGCAAGGGAA ACCACCGATA    1380

GCAGTGTCTA GTAGCAACCT GTAAAGCCGC AATGCAGCAT CACTGGAAAA TACAAACCAA    1440

TGGCTAAAAG TACATAAGTT AATGCCTAAA GAAGTCATAT ACCAGCGGCT AATAATTGTA    1500

CAATCAAGTG GCTAAACGTA CCGTAATTTG CCAACGCGTT TCTAGATTGC AGAAGCACGG    1560

CAAAGCCCAC TTACCCACGT TTGTTTCTTC ACTCAGTCCA ATCTCAGCTG GTGATCCCCC    1620

AATTGGGTCG CTTGTTTGTT CCGGTGAAGT GAAAGAAGAC AGAGGTAAGA ATGTCTGACT    1680

CGGAGCGTTT TGCATACAAC CAAGGGCAGT GATGGAAGAC AGTGAAATGT TGACATTCAA    1740

GGAGTATTTA GCCAGGGATG CTTGAGTGTA TCGTGTAAGG AGGTTTGTCT GCCGATACGA    1800

CGAATACTGT ATAGTCACTT CTGATGAAGT GGTCCATATT GAAATGTAAG TCGGCACTGA    1860

ACAGGCAAAA GATTGAGTTG AAACTGCCTA AGATCTCGGG CCCTCGGGCC TTCGGCCTTT    1920

GGGTGTACAT GTTTGTGCTC CGGGCAAATG CAAAGTGTGG TAGGATCGAA CACACTGCTG    1980

CCTTTACCAA GCAGCTGAGG GTATGTGATA GGCAAATGTT CAGGGGCCAC TGCATGGTTT    2040

CGAATAGAAA GAGAAGCTTA GCCAAGAACA ATAGCCGATA AGATAGCCT CATTAAACGG     2100

AATGAGCTAG TAGGCAAAGT CAGCGAATGT GTATATATAA AGGTTCGAGG TCCGTGCCTC    2160

CCTCATGCTC TCCCCATCTA CTCATCAACT CAGATCCTCC AGGAGACTTG TACACCATCT    2220

TTTGAGGCAC AGAAACCCAA TAGTCAACCG CGGACTGCGC ATCATG                   2266

(2) INFORMATION FOR SEQ ID NO:21:

(i) SEQUENCE CHARACTERISTICS:
             (A) LENGTH: 1781 base pairs
             (B) TYPE: nucleic acid
             (C) STRANDEDNESS: both
             (D) TOPOLOGY: both (ii) MOLECULE TYPE: cDNA (xi) SEQUENCE DESCRIPTION: SEQ ID NO:21:

CAATTCTCAC GGTGAATGTA GGCCTTTTGT AGGGTAGGAA TTGTCACTCA AGCACCCCCA      60

ACCTCCATTA CGCCTCCCCC ATAGAGTTCC CAATCAGTGA GTCATGGCAC TGTTCTCAAA    120

TAGATTGGGG AGAAGTTGAC TTCCGCCCAG AGCTGAAGGT CGCACAACCG CATGATATAG    180

GGTCGGCAAC GGCAAAAAAG CACGTGGCTC ACCGAAAAGC AAGATGTTTG CGATCTAACA    240

TCCAGGAACC TGGATACATC CATCATCACG CACGACCACT TTGATCTGCT GGTAAACTCG    300

TATTCGCCCT AAACCGAAGT GCGTGGTAAA TCTACACGTG GGCCCCTTTC GGTATACTGC    360

GTGTGTCTTC TCTAGGTGGC ATTCTTTTCC CTTCCTCTAG TGTTGAATTG TTTGTGTTGG    420

AGTCCGAGCT GTAACTACCT CTGAATCTCT GGAGAATGGT GGACTAACGA CTACCGTGCA    480

CCTGCATCAT GTATATAATA GTGATCCTGA GAAGGGGGGT TTGGAGCAAT GTGGGACTTT    540

GATGGTCATC AAACAAAGAA CGAAGACGCC TCTTTTGCAA AGTTTTGTTT CGGCTACGGT    600

GAAGAACTGG ATACTTGTTG TGTCTTCTGT GTATTTTTGT GGCAACAAGA GGCCAGAGAC    660

AATCTATTCA AACACCAAGC TTGCTCTTTT GAGCTACAAG AACCTTCTAA ATATATATCT    720

AGTGGCCAGA ATGCCTAGGT CACCTCTAAA TGTGTAATTT GCCTGCTTGA CCGACTGGGG    780

CTGTTCGAAG CCCGAATGTA GGATTGTTAT CCGAACTCTG CTCGTAGAGG CATGTTGTGA    840

ATCTGTGTCG GCAGGACAC GCCTCGAAGG TTCACGGCAA GGGAAACCAC CGATAGCAGT     900
```

-continued

```
GTCTAGTAGC AACCTGTAAA GCCGCAATGC AGCATCACTG GAAAATACAA ACCAATGGCT      960

AAAAGTACAT AAGTTAATGC CTAAAGAAGT CATATACCAG CGGCTAATAA TTGTACAATC     1020

AAGTGGCTAA ACGTACCGTA ATTTGCCAAC GCGTTTCTAG ATTGCAGAAG CACGGCAAAG     1080

CCCACTTACC CACGTTTGTT TCTTCACTCA GTCCAATCTC AGCTGGTGAT CCCCCAATTG     1140

GGTCGCTTGT TTGTTCCGGT GAAGTGAAAG AAGACAGAGG TAAGAATGTC TGACTCGGAG     1200

CGTTTTGCAT ACAACCAAGG GCAGTGATGG AAGACAGTGA AATGTTGACA TTCAAGGAGT     1260

ATTTAGCCAG GGATGCTTGA GTGTATCGTG TAAGGAGGTT TGTCTGCCGA TACGACGAAT     1320

ACTGTATAGT CACTTCTGAT GAAGTGGTCC ATATTGAAAT GTAAGTCGGC ACTGAACAGG     1380

CAAAAGATTG AGTTGAAACT GCCTAAGATC TCGGGCCCTC GGGCCTTCGG CCTTTGGGTG     1440

TACATGTTTG TGCTCCGGGC AAATGCAAAG TGTGGTAGGA TCGAACACAC TGCTGCCTTT     1500

ACCAAGCAGC TGAGGGTATG TGATAGGCAA ATGTTCAGGG GCCACTGCAT GGTTTCGAAT     1560

AGAAAGAGAA GCTTAGCCAA GAACAATAGC CGATAAAGAT AGCCTCATTA AACGGAATGA     1620

GCTAGTAGGC AAAGTCAGCG AATGTGTATA TATAAAGGTT CGAGGTCCGT GCCTCCCTCA     1680

TGCTCTCCCC ATCTACTCAT CAACTCAGAT CCTCCAGGAG ACTTGTACAC CATCTTTTGA     1740

GGCACAGAAA CCCAATAGTC AACCGCGGAC TGCGCATCAT G                        1781
```

(2) INFORMATION FOR SEQ ID NO:22:

(i) SEQUENCE CHARACTERISTICS:
        (A) LENGTH: 1781 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:22:

```
CAATTCTCAC GGTGAATGTA GGCCTTTTGT AGGGTAGGAA TTGTCACTCA AGCACCCCCA       60

ACCTCCATTA CGCCTCCCCC ATAGAGTTCC CAATCAGTGA GTCATGGCAC TGTTCTCAAA      120

TAGATTGGGG AGAAGTTGAC TTCCGCCCAG AGCTGAAGGT CGCACAACCG CATGATATAG      180

GGTCGGCAAC GGCAAAAAAG CACGTGGCTC ACCGAAAAGC AAGATGTTTG CGATCTAACA      240

TCCAGGAACC TGGATACATC CATCATCACG CACGACCACT TTGATCTGCT GGTAAACTCG      300

TATTCGCCCT AAACCGAAGT GCGTGGTAAA TCTACACGTG GGCCCCTTTC GGTATACTGC      360

GTGTGTCTTC TCTAGGTGGC ATTCTTTTCC CTTCCTCTAG TGTTGAATTG TTTGTGTTGG      420

AGTCCGAGCT GTAACTACCT CTGAATCTCT GGAGAATGGT GGACTAACGA CTACCGTGCA      480

CCTGCATCAT GTATATAATA GTGATCCTGA GAAGGGGGGT TTGGAGCAAT GTGGGACTTT      540

GATGGTCATC AAACAAAGAA CGAAGACGCC TCTTTTGCAA AGTTTTGTTT CGGCTACGGT      600

GAAGAACTGG ATACTTGTTG TGTCTTCTGT GTATTTTTGT GGCAACAAGA GGCCAGAGAC      660

AATCTATTCA AACACCAAGC TTGCTCTTTT GAGCTACAAG AACCTTCTAA ATATATATCT      720

AGTGGCCAGA ATGCCTAGGT CACCTCTAAA TGTGTAATTT GCCTGCTTGA CCGATCTAAA      780

CTGTTCGAAG CCCGAATGTA GGATTGTTAT CCGAACTCTG CTCGTAGAGG CATGTTGTGA      840

ATCTGTGTCG GGCAGGACAC GCCTCGAAGG TTCACGGCAA GGGAAACCAC CGATAGCAGT      900

GTCTAGTAGC AACCTGTAAA GCCGCAATGC AGCATCACTG GAAAATACAA ACCAATGGCT      960

AAAAGTACAT AAGTTAATGC CTAAAGAAGT CATATACCAG CGGCTAATAA TTGTACAATC     1020

AAGTGGCTAA ACGTACCGTA ATTTGCCAAC GCGTTTCTAG ATTGCAGAAG CACGGCAAAG     1080
```

```
CCCACTTACC CACGTTTGTT TCTTCACTCA GTCCAATCTC AGCTGGTGAT CCCCCAATTG    1140

GGTCGCTTGT TTGTTCCGGT GAAGTGAAAG AAGACAGAGG TAAGAATGTC TGACTCGGAG    1200

CGTTTTGCAT ACAACCAAGG GCAGTGATGG AAGACAGTGA AATGTTGACA TTCAAGGAGT    1260

ATTTAGCCAG GGATGCTTGA GTGTATCGTG TAAGGAGGTT TGTCTGCCGA TACGACGAAT    1320

ACTGTATAGT CACTTCTGAT GAAGTGGTCC ATATTGAAAT GTAAGTCGGC ACTGAACAGG    1380

CAAAAGATTG AGTTGAAACT GCCTAAGATC TCGGGCCCTC GGGCCTTCGG CCTTTGGGTG    1440

TACATGTTTG TGCTCCGGGC AAATGCAAAG TGTGGTAGGA TCGAACACAC TGCTGCCTTT    1500

ACCAAGCAGC TGAGGGTATG TGATAGGCAA ATGTTCAGGG GCCACTGCAT GGTTTCGAAT    1560

AGAAAGAGAA GCTTAGCCAA GAACAATAGC CGATAAAGAT AGCCTCATTA AACGAATGA     1620

GCTAGTAGGC AAAGTCAGCG AATGTGTATA TATAAAGGTT CGAGGTCCGT GCCTCCCTCA    1680

TGCTCTCCCC ATCTACTCAT CAACTCAGAT CCTCCAGGAG ACTTGTACAC CATCTTTTGA    1740

GGCACAGAAA CCCAATAGTC AACCGCGGAC TGCGCATCAT G                        1781
```

(2) INFORMATION FOR SEQ ID NO:23:

(i) SEQUENCE CHARACTERISTICS:
        (A) LENGTH: 745 base pairs
        (B) TYPE: nucleic acid
        (C) STRANDEDNESS: single
        (D) TOPOLOGY: linear (xi) SEQUENCE DESCRIPTION: SEQ ID NO:23:

```
GGACCTACCC AGTCTCACTA CGGCCAGTGC GGCGGTATTG GCTACAGCGG CCCCACGGTC     60

TGCGCCAGCG GCACAACTTG CCAGGTCCTG AACCCTTACT ACTCTCAGTG CCTGTAAAGC    120

TCCGTGCGAA AGCCTGACGC ACCGGTAGAT TCTTGGTGAG CCCGTATCAT GACGGCGGCG    180

GGAGCTACAT GGCCCCGGGT GATTTATTTT TTTTGTATCT ACTTCTGACC CTTTTCAAAT    240

ATACGGTCAA CTCATCTTTC ACTGGAGATG CGGCCTGCTT GGTATTGCGA TGTTGTCAGC    300

TTGGCAAATT GTGGCTTTCG AAAACACAAA ACGATTCCTT AGTAGCCATG CATTTTAAGA    360

TAACGGAATA GAAGAAAGAG GAAATTAAAA AAAAAAAAAA AACAAACATC CCGTTCATAA    420

CCCGTAGAAT CGCCGCTCTT CGTGTATCCC AGTACCACGT CAAAGGTATT CATGATCGTT    480

CAATGTTGAT ATTGTTCCGC CAGTATGGCT CCACCCCCAT CTCCGCGAAT CTCCTCTTCT    540

CGAACGCGGT AGTGGCTGCT GCCAATTGGT AATGACCATA GGGAGACAAA CAGCATAATA    600

GCAACAGTGG AAATTAGTGG CGCAATAATT GAGAACACAG TGAGACCATA GCTGGCGGCC    660

TGGAAAGCAC TGTTGGAGAC CAACTTGTCC GTTGCGAGGC CAACTTGCAT TGCTGTCAAG    720

ACGATGACAA CGTAGCCGAG GACCC                                         745
```

(2) INFORMATION FOR SEQ ID NO:24:

(i) SEQUENCE CHARACTERISTICS:
        (A) LENGTH: 1627 base pairs
        (B) TYPE: nucleic acid
        (C) STRANDEDNESS: single
        (D) TOPOLOGY: linear (xi) SEQUENCE DESCRIPTION: SEQ ID NO:24:

```
GGCGGTATTG GCTACAGCGG CCCCACGGTC TGCGCCAGCG GCACAACTTG CCAGGTCCTG     60

AACCCTTACT ACTCTCAGTG CCTGTAAAGC TCCGTGCGAA AGCCTGACGC ACCGGTAGAT    120

TCTTGGTGAG CCCGTATCAT GACGGCGGCG GGAGCTACAT GGCCCCGGGT GATTTATTTT    180

TTTTGTATCT ACTTCTGACC CTTTTCAAAT ATACGGTCAA CTCATCTTTC ACTGGAGATG    240
```

| | |
|---|---|
| CGGCCTGCTT GGTATTGCGA TGTTGTCAGC TTGGCAAATT GTGGCTTTCG AAAACACAAA | 300 |
| ACGATTCCTT AGTAGCCATG CATCGGGATC CTTTAAGATA ACGGAATAGA AGAAAGAGGA | 360 |
| AATTAAAAAA AAAAAAAAAA CAAACATCCC GTTCATAACC CGTAGAATCG CCGCTCTTCG | 420 |
| TGTATCCCAG TACCACGGCA AAGGTATTTC ATGATCGTTC AATGTTGATA TTGTTCCCGC | 480 |
| CAGTATGGCT GCACCCCCAT CTCCGCGAAT CTCCTCTTCT CGAACGCGGT AGTGGCGCGC | 540 |
| CAATTGGTAA TGACCATAGG GAGACAAACA GCATAATAGC AACAGTGGAA ATTAGTGGCG | 600 |
| CAATAATTGA GAACACAGTG AGACCATAGC TGGCGGCCTG GAAAGCACTG TTGGAGACCA | 660 |
| ACTTGTCCGT TGCGAGGCCA ACTTGCATTG CTGTCAAGAC GATGACAACG TAGCCGAGGA | 720 |
| CCGTCACAAG GGACGCAAAG TTGTCGCGGA TGAGGTCTCC GTAGATGGCA TAGCCGGCAA | 780 |
| TCCGAGAGTA GCCTCTCAAC AGGTGGCCTT TTCGAAACCG GTAAACCTTG TTCAGACGTC | 840 |
| CTAGCCGCAG CTCACCGTAC CAGTATCGAG GATTGACGGC AGAATAGCAG TGGCTCTCCA | 900 |
| GGATTTGACT GGACAAAATC TTCCAGTATT CCCAGGTCAC AGTGTCTGGC AGAAGTCCCT | 960 |
| TCTCGCGTGC ANTCGAAAGT CGCTATAGTG CGCAATGAGA GCACAGTAGG AGAATAGGAA | 1020 |
| CCCGCGAGCA CATTGTTCAA TCTCCACATG AATTGGATGA CTGCTGGGCA GAATGTGCTG | 1080 |
| CCTCCAAAAT CCTGCGTCCA ACAGATACTC TGGCAGGGGC TTCAGATGAA TGCCTCTGGG | 1140 |
| CCCCCAGATA AGATGCAGCT CTGGATTCTC GGTTACNATG ATATCGCGAG AGAGCACGAG | 1200 |
| TTGGTGATGG AGGGACAGGA GGCATAGGTC GCGCAGGCCC ATAACCAGTC TTGCACAGCA | 1260 |
| TTGATCTTAC CTCACGAGGA GCTCCTGATG CAGAAACTCC TCCATGTTGC TGATTGGGTT | 1320 |
| GAGAATTTCA TCGCTCCTGG ATCGTATGGT TGCTGGCAAG ACCCTGCTTA ACCGTGCCGT | 1380 |
| GTCATGGTCA TCTCTGGTGG CTTCGTCGCT GGCCTGTCTT TGCAATTCGA CAGCAAATGG | 1440 |
| TGGAGATCTC TCTATCGTGA CAGTCATGGT AGCGATAGCT AGGTGTCGTT GCACGCACAT | 1500 |
| AGGCCGAAAT GCGAAGTGGA AAGAATTTCC CGGNTGCGGA ATGAAGTCTC GTCATTTTGT | 1560 |
| ACTCGTACTC GACACCTCCA CCGAAGTGTT AATAATGGAT CCACGATGCC AAAAAGCTTG | 1620 |
| TGCATGC | 1627 |

(2) INFORMATION FOR SEQ ID NO:25:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (xi) SEQUENCE DESCRIPTION: SEQ ID NO:25:

| | |
|---|---|
| GGACTGGCAT CATGGCGCCC TCAGTTACAC TGCCGTTGAC CACGGCCATC CTGGCCATTG | 60 |
| CCCGGCTCGT CGCCGCCCAG CAACCGGGTA C | 91 |

(2) INFORMATION FOR SEQ ID NO:26:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 18..95

(xi) SEQUENCE DESCRIPTION: SEQ ID NO:26:

```
AACCGCGGAC TGGCATC ATG GCG CCC TCA GTT ACA CTG CCG TTG ACC ACG                50
                    Met Ala Pro Ser Val Thr Leu Pro Leu Thr Thr
                     1               5                  10

GCC ATC CTG GCC ATT GCC CGG CTC GTC GCC GCC CAG CAA CCG GGT                    95
Ala Ile Leu Ala Ile Ala Arg Leu Val Ala Ala Gln Gln Pro Gly
        15                  20                  25

AC                                                                             97
```

(2) INFORMATION FOR SEQ ID NO:27:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:27:

```
Met Ala Pro Ser Val Thr Leu Pro Leu Thr Thr Ala Ile Leu Ala Ile
 1               5                  10                  15

Ala Arg Leu Val Ala Ala Gln Gln Pro Gly
                20                  25
```

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:28:

```
ACT ACG TAG TCG ACT                                                            15
```

(2) INFORMATION FOR SEQ ID NO:29:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:29:

```
CTAGTGGCCA GAATGCCTAG GTCACCTCTA GAGGTACCCT GCAGCTCGAG                         50
```

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:30:

```
CTAGCTCGAG CTGCAGGGTA CCTCTAGAGG TGACCTAGGC ATTCTGGCCA                         50
```

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO:31:

GGACTGCGCA TCATGCAG                                         18

(2) INFORMATION FOR SEQ ID NO:32:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:32:

GATCCTGCAT GATGCGCAGT CCGC                                  24

(2) INFORMATION FOR SEQ ID NO:33:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:33:

AATTCGTCGA CG                                               12

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:34:

TAATAATAAC CGGCGGTATT GG                                    22
```